United States Patent [19]
Dietz

[11] Patent Number: 6,048,965
[45] Date of Patent: Apr. 11, 2000

[54] MAMMALIAN REGULATOR OF NONSENSE-MEDIATED RNA DECAY

[75] Inventor: Harry C. Dietz, Towson, Md.

[73] Assignee: The Johns Hopkins University School of Medicine, Baltimore, Md.

[21] Appl. No.: 09/270,984

[22] Filed: Mar. 17, 1999

Related U.S. Application Data

[62] Division of application No. 08/724,354, Oct. 1, 1996
[60] Provisional application No. 60/016,482, Apr. 29, 1996.

[51] Int. Cl.$^7$ .................................................. C07K 14/47
[52] U.S. Cl. ............................................................ 530/350
[58] Field of Search ............................................. 530/350

[56] References Cited

U.S. PATENT DOCUMENTS 5,585,479  12/1996  Hoke et al. ............................ 536/24.5

OTHER PUBLICATIONS

Adams et al. (1995) Initial assessment of human gene diversity and expression paterns based upon 83 million nucleotides of cDNA sequences. Nature 37 (suppl.) 3–17 Sep. 1995.

Khan et al. (1992) Single pass sequencing and physical and genetic mapping of human brain cDNA's. Nature Genetics 2:180–185 Nov. 1992.

Leeds, et al., Gene products that promote mRNA turnover in saccharomyces, Molec. Cell Biol., vol. 12, No. 5, pp. 2165–2177 (1992).

Czaplinski, et al., Purification and characterization of the Upf1 protein: A factor involved in translation and mRNA degradation, RNA, Oct. 1995, vol. 1, pp. 610–633.

He et al., Identification of a novel component of the nonsense–mediated mRNA decay pathway by use of an interacting protein screen, Genes and Development, Feb. 1995, vol. 9, pp. 437–454.

Michienzi, et al., U1 smll nuclear RNA chimeric ribozymes with substrate specificity for the Rev pre–mRNA of human immunodeficiency virus, Proc. Natl. Sci. USA, 93:7219, Jul. 1996.

Bertrant, et al., Can Hammerhead ribozymes be efficient tools to inactive gene function?, Nucleic Acids Research, 22(3):293, 1994.

Perlick, et al., American Society of Human Genetic Meeting, San Francisco, Nov. 1, 1996.

Montgomery, et al., American Society of Human Genetic Meeting, San Francisco, Oct. 31, 1996.

Perlick et al. (Oct. 1996) Mammalian orthologues of a yeast regulator of nonsense transcript stability. Proc. Natl. Acad. Sci. USA 93:10928–10932.

*Primary Examiner*—Robert A. Schwartzman
*Attorney, Agent, or Firm*—Gray Cary Ware & Freidenrich LLP; Lisa A. Haile

[57] ABSTRACT

All eukaryotes that have been studied to date possess the ability to detect and degrade transcripts that contain a premature signal for the termination of translation. This process of nonsense-mediated RNA decay (NMRD) has been most comprehensively studied in the yeast, *Saccharomyces cerevisiae* where at least three trans-acting factors (Upf1p through Upf3p) are required. The present invention provides cDNAs encoding human and murine RENT1 (regulator of nonsense transcripts). rent1 is the first identified mammalian protein that contains all of the putative functional elements in Upf1p including zinc finger-like motifs and NTPase domains as well as all motifs common to members of helicase superfamily I. Moreover, expression of a chimeric protein, containing the central region of RENT1 flanked by the extreme N- and C-termini of Upf1p, complements the Up1p-deficient phenotype in yeast.

4 Claims, 14 Drawing Sheets

```
Rent1    1-  MSVEAYGPSSQTLTFLDTEEAELLGADTQGSEFEFTDFLPSQTQTPPGGPGGGPGGGAG
Sis1p(y)      (38)|•| ||     ||    ••   •   •   |||| |||||  |
Grp10(b)         (52)                                         
                                                        Z
Rent1        GPGGAGAGAAAGQLDAQVGPEGILQNGAVDDSVAKTSQLLAELNFEEDEEDTYYTKDLPI
Sis1p(y)     | |||   •|(102)     •|  ||   (260)||•|••|  || ||||  |(274)
Grp10(b)           |(126)
```

FIG. 1A

```
                                    N      S
Rent1   918- KLVNTINPGARFMTTAMYDAREAIIPGSVYDRSSQGRPSSMYFQTHDQIGMISAGPSHVA
                  (217)|  •|| ||•   |    (231)
                                    T
             AMNIPIPFNLVMPPPMPPPPGYFGQANGPAAGRGTPKGKTGRGGRQKNRFGLPGPSQTNLPN
Ews(h/m)     (546)||     ||  ||||    ||       |||•    |||| |||(624)
                                              (583-612)
                                    V
Rent1   1038- SQASQDVASQFFSQGALTQGYISMSQPSQMSQPGLSQPELSQDSYLGDEFKSQIDVALSQ
                                    S
             DSTYQGERAYQHGGVTGLSQY•  -1118
```

FIG. 1C

```
Rent1     121- HACSYCGIHDPACVVYCNTSKKWFCNGRGNTSGSHIVNHLVRAKCKEVTLHKDGPLGETV
               ••|•||||• •||• ||• |||||| • ||•|||||||| • • |•|| |• ||•|‧|
Upf1p(y)   60- NSCAYCGIDSAKCVIKCNSCKKWFCNTKNGTSSSHIVNHLVLSHHNVVSLHPDSDLGDTV
                 1

Rent1          LECYNCGCRNVFLLGFIPAKADSVVVLLCRQPCASQSSLKDINWDSSQWQPLIQDRCFLS
               ||||||||•|||||||••||•••|||||||| ||| |• ||| |||||||•|| •||
Upf1p(y)       LECYNCGRKNVFLLGFVSAKSEAVVVLLCRIPCA-Q--TKNANWDTDQWQPLIEDRQLLS
                 2

Rent1     241- WLVKIPSEQEQLRARQITAQQINKLEELWKENPSATLEDLEKPGVDEEPQHVLLRYEDAY
               |•• |•|•|•|| ||• ||•||| |•| ||••|• •| •||||•|||
Upf1p(y)  178- WVAEQPTEEEKLKARLITPSQISKLEAKWRSNKDATINDIDAPEEQEAIPPLLLRYQDAY F
Rent1          QYQNIFGPLVKLEADYDKKLKESQTQDNITVRWDLGLNKKRIAYFTLPKTDSDMRLMQGD
               •|| •|||•|||||||||•|||||• ••|•| | |•||••••| ||| •|•••• ||
Upf1p(y)       EYQRSYGPLIKLEADYDKQLKESQALEHISVSWSLALNNRHLASFTLSTFESELKVAIGD Rent1     361- EICLRYKGDLAPLWKGIGHVIKVPDNYGDEIAIELRS-SVGAPVEVTHNFQVDFVWKSTS
                  |• |•| | |••••|••• | •••||•• •| ••| | •|•||•||
Upf1p(y)  298- EMILWYSGMQHPDWEGRGYIVRLPNSFQDTFTLELKPKSTPPPTHLTTGFTAEFIWKGTS V               G
Rent1          FDRMQSALKTFAVDETSVSGYIYHKLLGHEVEDVIIKCQLPKRFTAQALPDLNHSQVYAV
               •|||| ||| ||•| |•|||•| |•||||•| |• • ||| |• •••|| || ||
Upf1p(y)       YDRMQDALKKFAIDKKSISGYLYYKILGHQVVDISFDVPLPKEFSIPNFAQLNSSQSNAV G
Rent1     480- KTVLQRPLSLIQGPPGTGKTYTSATIYIHLARQDNGPYLYCAPSNIAYDQLTEKIHQTGL
               ||||||||||||||||||||||||||||||||•• ••• •|||||||•|•|• |••• ||
Upf1p(y)  418- SHVLQRPLSLIQGPPGTGKTVTSATIVYHLSKIHKDRILVCAPSNVAVDHLAAKLRDGL A
Rent1          KVVRLCPKSREAIDSPVSFLALHNQIRNMDSMPELQKLQQLKDETGELSSADEKRYRALK
               ||||| •|||| ••|•|| ||||| • •• ||••| •|||| |||||••|| ||• |
Upf1p(y)       KVVRLTAKSREDVESSVSNLALHNLV-GRGAKGELKNLLKLKDEVGELSASDTKRFVKLV
                                                        4

Rent1     600- RTAERELLMNADVICCTCVGAGDPRLAKMQFRSILIDESTQATEPECMVPVVLGAKQLIL
               | •| |•| |•||||||||||| || •||••||||||||||•••|•| ||||•|‧||
Upf1p(y)  537- RFTEAEILNKADVVCCTCVGAGDKRLDT-KFRTVLIDESTQASEPECLIPIVKGAKQVIL
                         5

Rent1          VGDHCQLGPVVMCKKAAKAGLSQSLFERLVVLGIRPIRLQVQYRMHPALSAFPSNIEYEG
               |||| ||||• •||| •|||| ||| |||||||||• || ||||•|||||•| || |||•||||
Upf1p(y)       VGDHQQLGPVILERKAADAGLKQSLFERLISLGHVPIRLEVQYRMNPYLSEFPSNMFYEG Rent1          SLQNGVTAADRVKKGFDFQWPQPDKPMFFYVTQGQEEIASSGTSYLNRTEAANVEKITTK
               |||||||  •|    |||   • ||  |•|•|||•••|||•||| || | |•| ||
Upf1p(y)       SLQNGVTIEQRTVPNSKFPWPIRGIPMMFWANYGREEISANGTSFLNRIEAMNCERIITK Rent1          LLKAGAKPDQIGIITPYEGQRSYLVQYMQFSGSLHTKLYQEVEIASVDAFQGREKDFIIL
               | •| ||•|||||||||||||•••|||| •||• || ||•|||||||||•|||
Upf1p(y)       LFRDGVKPEQIGVITPYEGQRAYILQYMQMNGSLDKDLYIKVEVASVDAFQGREKDYIIL SY   A
Rent1     840- SCVRANEHQGIGFLNDPRRLNVALTRARIGVIIVGNPKALSKQPLWNHLLIFYKEQKVLV
               ||||||||•|•|||| ||||||||||||•||•|•|||||| |••|•|• ||||||| ••|• ||
Upf1p(y)  776- SCVRANEQQAIGFLRDPRRLNVGLTRAKYGLVILGNPRSLARNTLWNHLLIHFREKGCLV Rent1          EGPLNNLRESLMQFSKPR   -917
               || |•||• •|• •|•
Upf1p(y)       EGTLDNLQLCTVQLVRPQ   -853
```

FIG. IB

```
ATGGCATACTGAGTGGCCCTTGTTGCCAGCCAGCATTGACTCTTTAATCCTTTTGCTCAGTAGAGGAGCACGGGAT
TCAGTAGCATAGACCTCAGGAGTGGGGCCTCTGGGTGCCCTTGGTGGCCTGCACTGGTGATACTGTGTTCTCTCTA
GGTTGGACCAGAGGGCATCTTGCAAAATGGGGCTGTGGATGACAGTGTGGCCAAGACCAGCCAGCTGCTAGCTGAG
CTGAACTTCGAGGAAGATGAAGAGGACACATACTACACTAAGGACCTCCCAGTCCACGCCTGCAGGTATGCTGCAG
GGCTCCAGGACCAAGAGGTGGCCTGCTTCAGAGTACCGGTTCCTTGTTCAGAACCCAGAGCACAGTACCTAACACC
CCAGATTCATAGGGTTCTTGTGGGTCCCCTGCCATAGCCACTCAAGCAAGGACCCCTGAAGGAGCCAAGGCAGGGC
ATGGATCCTGACTAAATCAGCTCCATCAGGGCCACATGAGGGCACTGGAGGCTTAAAGAGTTGGAATGTCCTTGTT
GTGGAATACCCAGCTCAGCTAACTTCACACCCACCCACCCACACACACACCCAGCAAGGCCAGAGCTTGTCTTTAC
TAGGGTTTTGTAGCCATCTGCCGCCCTCTACAGGGCTGTTTTGGCCTCTCCTCTCCACACCTATTGCTTTCCGTTA
TAATGGCTCTCTCCTGGTTGACAAGTGTTTTCTTTTTCTTTTTTTTTTTTTTAAAGATTTATTTATTTATTATA
TGTAAGTACACTGTAGCTGTCTTCAGACACACCAGAAGAGGGAGTCAGATCTCGTGATCAGATGGTTGTGAGCCAC
CATGTGGTTGCTGGGATTTGAACTCCTGACCTTCGGAAGAGCAGTTGGGTGCTTACCCACTGAGCCATCTCACC
AGCCCGACAAGTGTTTTCGAGGATAAAACCAGAGCTACAGGCAGGCTGATCTGGGAGCCCTAGTCGTCCTTCCAC
CAGGAATAGACGAGGAGCCCAGTGAGAGCGTTTTCTGGTTTGACACCTCATGGCCCAGCCTGCCGGTGCACAAC
AGAGCTATGGAGACCCAGTGATTCAGGGGCCTCCCTTAGCCTGGGTTGGGCCTGAGCATTCTCTGGTTGCAGAGTA
CCTGCCTTCTGGAGTCAGGTGCTCCCACAACCTTGTTAGAAACTTGCAGGCTGAAGGGAAGGGGCCAGGATTGCCT
TGGGCCTGTGCCACTCAGGCATCTGTGTTGCCCTCACACTAACCAAACCTGAAAGCTGCAGGCCAGTACTGACTGT
TGATGTTTGGGCTTTTCCAGTTACTGTGGAATCCATGATCCTGCCTGCGTGGTTTACTGTAATACCAGCAAGAAGT
GGTTCTGCAATGGCCGAGGAAATACTTCTGGCAGGTAGCTGACAGCCATGCATGTGTGTTTAATCAGCAACACTAG
GGCTGCTGTGAGTTACGGTGTTGTTGGAGCAAAGCTGGAATGAGATGGTGCTGGTGAACCTGGGCTCCCCCTTTGA
CTGGTGTAACTTGAAACAGATGGTGGCGTGTGAACGCTTCGACATGTTTATCCTTGATTGATTCTCTGCCTCGCTC
ATTATGTGAGGAGTTTGGCTTAATTCTGTTCTCAGGCTGTGCCTGCCTCTCATGAAATGAGGCTGGCATGGCCTGC
CTGTCCTTGTTCCTGGAGGTTGAGGGCATCCAGCTGAGCCAGTTGACTTGATTGTCTCTGGAACCAATGGTTCAA
GATCCTAAGTCATTAGGAACAACTAGACTCATCCCTATATCATGCTGGCTCTCCATGCAAGTGTCAGGAAACACTG
TTGGAGAGAAACAACTGAGCCAGGTGTGCCTGTTTCCCACTGCCACCAGGGGTGTGGCTTGTTTCTGAGGACATTC
TGTAAAAAGAATGCCACAGAAGGTTGTAGGTACCAGGTCTACAGTGAGGCAGGGATTATCATCTTTAAAAGATCTT
AAAGTCACTTTCAGGGACCAAGACATCCCATTCTCAGAAGGAGGAGTAAGACCTACAAAGCTAAGAATGGCTGGAT
GGTCACTACAGTGGGGGTTTCATGGGATCATACAGAAAGACAACTAAGACAGTCAGGAAGAACTGGCAGAGCCTGT
GGGCCCTGAGGTGGCCAGCCAATGTGGGCCACTATTGGGGTAGGCCATGTCCTCATATGTGACGGGGAAGGGATGG
GAGCTATGGTCCTTAGGGCAGCTCCTTGCTATAGAGACCAGGAGGTGACCTGTTTGTTTAAATAGGCATGGAAAAA
GAGGACCTGGAAGGAGCCATTTTTTGCTGAGCATGGCTGCCAGAGGTTAAGTTAGCACCATGTGCTGGGGCTAGAG
AAAGAGGAAATGGAGGGGTTGTGTGAGTCAGTGAACAAGCGAGCGGGGCTGAGGCTCCCTGGGCACCTGTGCCCCT
GAGGTGTGACCATCTGGTCTGTGCTGACAGACCATGAGCAGTACTGGACATTTTGCATGGGGTAGCCGACCTGGAG
GTGCCGAGAAGCCAAGCTTGGGGTGTTAACTGCGATGGTTTCCTGGTCTCAGCCACATTGTGAATCACCTCGTGAG
GGCAAAATGCAAGGAAGTGACGCTGCACAAGGACGGGCCTCTGGGCGAGACCGTGCTGGAGTGCTACAACTGTGGC
TGCCGCAACGTCTTCCTGCTGGGCTTCATCCCTGCGAAGGCCGACTCTGTGGTGGTGCTGTTGTGCAGGTGAGCTG
CCTGCAGCAGGGCTGGACTGGAGAGGACAATGTCTGCTGGGACCAAGTTCTGTGTGTATTCTGGTCAAATTAGAAA
ATGAAGTCTGGCCTGATGTGGTAGTGTACACTTTTAACTTCAGCCCTGGGGAGGCAAAGGCAGAAGTTTCTCTGAG
TTCAAGGCCAGCCTGGTCTACTAAGAGACCCAAAGGCCAAGCCAGGGCTACCCAGTTAGAACCTGTCTGAAAAACTG
AAAGAAGGAAAGTGACAGGTCTGCTGTGAACTGAGGCCAGAGCTGGGCGTCAGATGCTGCTGCCTTCTGGCT
AGTTTGAGGCCTCCTGGGCCAGGTCCCAACCCTCTCTCCTGCCCCACACCTGCACAGGCAGCCCTGTGCCAGCCAG
AGCAGCCTGAAGGACATCAACTGGGACAGCTCACAGTGGCAGCCCTAATCCAGGACGGTGCTTTCTGTCATGGC
TGGTCAAGATTCCCTCTGAGCAGGAGCAGCTGCGAGCACGGCAGATCACGGCACAGCAGATCAACAAGCTGGAAGA
GCTCTGGAAGGTGAGCCACTCATAGACAAAAAGAAAAGTAACTGGCAAGCCTCACACTGGGCAGGAGATATTGGGG
GTGGGGGTGGGGACATGACCTAGGGCTCTGCAGGGGACATAGTGGATGGTCTGAGTAATTGGGTTAGGCTGTTATG
AGATTCCTACTCCAAGGAGCACCTGTCCTTATCCCTAATGACAAGTCAGGGTTCCAGATTAGGTTGGAGTTCTGTT
CTGGCTAGCTTTAGACTCTGACCTTGTTTTCCAAATGTGACTAGGGGTGTCAGTTGAGCACCCTCTAACCAGGAAT
CCCAAGTAGTATTGGATAGAAACCTTCTAAGCTTGTCCAGCTTAGTCTCTTTGCACTTGGGTGGTCAAGTTCCAGT
TATCTCAGTATGCCCAGGTTCTCTGTTCTCTGTCTCAGTGAGGCTCACAGAGGGCAGTTGGTCCCAGAGGGCAT
GTTGCTACAGGATATGAGAGAGGGACTTGGCTCACTGGGAGAATCATGAGACTCTGACAGCCGAATCTGGGGCTCC
AGATGGGCCTGAGTATTGTGCTGGGCCGTGGGGGTGCTGTTGCCAGGTTTATTGGGGTTAGAATGGTGTTGAGTAT
GCCAGGGCCATCAGAACAGTAGGCTCAGCGCAGGCCCCGGCACAGTGGCCACTCTCCACCTACGAGGGTTTGTGCT
GAGAGGCCTTGGCTTGCTTCTGAGCTCTTGATCACTGGCTGCCAGGACGAACACAGCACTATTCTTGGCCATAGGA
```

FIG. 4A

```
AAATCCTTCAGCCACTCTGGAGGACCTGGAGAAGCCAGGCGTAGACGAGGAGCCACAGCACGTGCTCCTGCGTTAC
GAGGATGCTTACCAGTACCAGAACATCTTCGGGCCACTGGTCAAGCTGGAGGCTGACTATGACAAGAAGTTGAAGG
AGTCACAGGTGATGTGGCACAACAGACCAGGCCTCTAGCAAAACATCTCCCGAGTCAGGGGCTCTTCCTGGCCTTG
AGCCTGGATGAAACCAGGCATGCAGATGAGAAAACCCTTGTGTCTGGTTCACAGCTTTGTCTGCAGCTCCAAGAAC
ATTTCTGGGATATGGGACCCATGCCACCAATTCCCCAAAGTGCCTTCCCTCCCTACAGAGCCTGGCGTGTGGGGTC
TCCTGAGGCTCTCTACAAAGCTTGCTGCTGGGACTGGCTTAGGCAGTGGGTGTTGGGGGGTCCTGGTTGCTTCTTT
CCCAGATGCTGGAGTTCCTGGCCGTGGATGCTGTGCTCTGCACCCCAAAGGCAGCACAGCACAGACATGGCCTTCC
TAGAGGCTCTGACCTGTGGGAAGCCCAGCCCGTGAATGAGTGTGGGGCTAACCCGGCCCATGTTTCTCATGTGTTC
AGACTCAAGATAACATCACGGTCAGGTGGGACCTGGGCCTTAACAAGAAGAGAATCGCCTTCTTCACTTTGCCCAA
GACTGACTCTGGTAATGAGGATTTAGTCATAATTTGGTTAAGAGGTGATTTTAAGTTTTAAAATATTTGTGACCAT
AAGTAGAATAAAATTCCTAGTCCCCATATCATGTCCCTTATGTGAACTCTGCATGGTGGAGGCCACGCCCTCTTG
AAAGTGCTAACTCTGCTACTCCTTCCTGCAAGACATGCGGCTCATGCAGGGTGATGAGATCTGTCTGCGGTACAAA
GGGGATCTGGCGCCCCTGTGGAAGGGGATTGGCCACGTCATCAAGGTTCCTGATAGTATCCTTTGTCATATCTGCT
AGGAGGATGGGTTCTGTAACAGGACCCTGGCTGTCCCCAGGGCTTTAATATGTACAACTTCTTCCTCTTAATATA
CAATTTCTTCTCTCTTTCCACTTTGTGAGACATACACACCGTGACATGGTAGTGAGTGCGCGTGCGAGCATGCACA
TGTGTGAGTGAAACAGCCTGGAATCTGTCTGCAGCAGTTCCTTTGCCTGATAGGCAAGGAGAGCTGGTCTAGTGAT
GAAGTCAGGGGCTCTGTAGAAAGGTGACTTTGAACAGGAAACTGACTTAACTCAGTTGCCAGATTATGGTGATGAGA
TTGCTATTGAGCTCCGCAGCAGCGTGGGTGCCCCTGTGGAAGTGACCCACAACTTCCAAGTGGATTTTGTGTGGAA
GTCAACCTCTTTTGATAGGTTTGTGAGGGCATACCCTTGGGGCCACCTCCACCTTTGGTACCTGTGGCTCGTGT
GGGTTTTACACTGGCTGTTTTTATAGGATGCAGAGTGCACTGAAGACCTTCGCTGTGGACGAGACCTCTGTGTCAG
GGTATATTTACCACAAGCTGCTGGGCCACGAGGTGGAGGATGTGGTCATCAAGTGCCAGCTGCCAAAGCGCTTCAC
AGCTCAGGGGCTCCCTGACCTCAACCACTCTCAGGTGCCATTAGGCCCCTAGGGCCAGGGTCTGTAGGGGCTGTGC
CTTTGCAGCTTTGCTGATGCTCCGTCCTTGCAGGTGTATGCTGTGAAGACCGTGCTGCAGAGACCACTCAGCCTCA
TCCAGGGCCCTCCAGGCACAGGCAAGACTGTGACATCAGCCACTATTGTCTACCACCTTGCTCGGCAGGGCAATGG
GTAGGTAGTAGCAAGAGCCTTGTGGGTGGGAGGTAGTAATGTCTTGTGTGGCCTTGTGGTCTGTTATAGCTCTGCC
GGGGCCACACAGAAAATATATACAGCGTTACAATACAGGCACCTTTTGTGTTCTACAACCCTCTGGCCTGCCTCAT
GTGGATGACAGGGTGAGGTCACCGTTGAGCTGATGGTGGCTAGGCAGGTGACAGGAGGCTTTGCTTGTTTTGCCTT
GGCTGTGCAGCTTTTCCCTGGGCCTTGCTGAGCTGCTCTGGGTGATGCTGACAGCCTATTCCACTCTCTGCAGGCC
TGTACTGGTTTGTGCTCCAAGTAACATCGCTGTGGACCAGCTCACAGAGAAGATCCACCAGACAGGACTGAAGGTC
GTACGCCTCTGTGCCAAGAGCCGTGAGGCCATTGACTCCCAGTGTCCTTCCTGGCTTTGCACAACCAGATCAGGA
ACATGGACAGGTGAGTATCTCCAGCTTCGGGCTCAGTACAGGCTGCGCCCTGCTGCTGGCGCTGACTCCCACCACA
TTTTCTGTAGCATGCCTGAGCTGCAGAAGCTGCAGCAGCTAAAGGATGAGACAGGCAGGCGAGCTGTCATCTGCAGATGA
GAAGCGGTACCGGGCGCTTAAGCGCACAGCGTGAGAGAGAACTTCTCATGGTGAGCTCAGTGCCAGCCCAGGAGCCT
TTGGGCTGTTCCTTGTGCAGAGGGATCTGGAGAGACTTGTCTGTTCGAGTCAGAAGCCTGGTAGCATGTCTGTAC
CTTTGCTTTTGAAGACTTGGAGGGACCTCATCTTCCTGATCTGTGCCATAGTCAGGAACATAGCTGCCACTCCTGT
CAGTCTCCAGTCTAACAAACCAGTCCATCAAAGCTGGAGTCTCAGCCTTGGGGTAGTACCACCAGCTCAGTACTGT
CCCAGAGATTATTGGCAGACACAGCTGTGTCAATGCTGGGGAGTGTGCTCCAGAAGGCTGTACCATTTGAAAGTTG
ACGCTCATGGTCCCTGGGATGTTCACACTTGGGCTGCAGGAGAAGTGGCTAGTTTACTTGTTGGGGAATTGTCTGT
GGAGAGCCAGTCTGGGGCAACACAGTAAGACCCTGTCAGAACAACTTGTGCGGGCGCACTTCAAGAGTGCTGGGTG
GGTGTAGAACAGGGTATTCCAGGTCCCACCCTAAGCCATCTAGCTGTGGTGAGGTAGGCACATGTGCCCTGATGTC
TGTGCCTTCCCCAGAATGCAGATGTCATATGCTGCACATGTGTGGGTGCTGGTGACCCGAGGCTGGCCAAGATGCA
GTTCCGTTCCATCCTCATTGACGAGAGCACCCAGGCCACTGAGCCTGAGTGCATGGTGCCTGTAGTCCTTGGGGCC
AAGCAGGTGGGTACCTGTCACTCATGTGGCCCTTGATAGTGGTGCTGGGTGACACAAGACCTGCTAGAGGTCTTTG
AAGGGGGCTGAGTCCCATGTGTTCCACAGGCCCGCGCCTCCTGGGGTGTTGGCAGCCTGTACTGAGCAGCTCCCCC
TACCCCCCTGGGGTACTCGTTCTGTTGCTTTTAGATGGTGGAGGTGACCCCTGTCCCTGTGGTAGGCACTTAGGAA
CATGGAGGGGTTAACTTGAGGGACTTCTTGCTGCAGCTAATCCTCGTCGGTGACCACTGCCAGCTGGGCCCAGTGG
TGATGTGCAAGAAGGCAGCCAAGGCCGGACTGTCACAATCGCTCTTCGAGCGCTTGGTGGTGCTGGGCATCCGGCC
CATCCGCCTGCAGGTGCAATACCGCATGCACCCTGCACTCAGCGCCTTTCCGTCCAACATCTTCTACGAGGGCTCA
TTGCAGAATGGCGTCACTGCAGGTAACAGTTGCAGCACTGTGAAGGGCATAGGGAAGGGCCATGAGGACGCAACCC
AACTGTTATACCCTATGCCCTTCATGGTGCTGCTCACCCCAGCTTCTCAGACACAGTGCTGCTGGAGTGTGTGGTG
GCTCACACAGTGGTCGTCATACCTTTCACCATGGCCAGGTCATGCACTGGCTCTGCTCCCATGGCTGTTGCTTTATG
CTGAACAGTCCCAGGCTAGGCACCCCATGCTTAGAAATGAACCAACCACCCCGACAACAGGAATTCCCAGCCTTTT
CCTTGTGATGGTGGTTGGCTGAGATGTCACCCTATCACAAGTTTAAGTGAGACCAGGCAGGTAGATTATGAGAGCT
TGTCTTCTGAGGTCAGCAGCTGATGACACCTCTTACCTGCAGCAATTTGAGGCTCTGTGAACAGGGAATTTAAGGA
CACTAGGGTCACCTTTGAATGTAGTTCTGGCCCTGTCCTAAGAGTATTTATGGCAGTGACCTCTTCAGGGTCTTTG
CACTGTATCTGTTGGTACAACCTAGAGGATCTGGAGCAGTAGACAGAGTGACACTGTGGTGTCAAGTGAGCCATAA
GTATACTGTCACACACCCTTGAAAGCTATTTGCTTTCATGGGAGGTTGGTACAGAAACCAACTGGGCCTTACTGTC
CTCCACGAAGCCTGAGTGAAGTGGAATGAAAGGTTGCTATCTGACTTGCTTTGCAACATAAATGTGTTTTTCACCA
```

FIG. 4B

```
AACTGTTAAAACATCTAGGCATGGCTCTCAGCTTTAATCCCAGGACTTGTGAAGCAGACAGGCAGGCTCTCTGGGA
GGTCAGGGCCATAGTGAAACCCTCTCTCAAACACACAAACACGGCTTCAGCACAGTGGCTTAGGCATGGATTTGAA
TGTCTGCCTTTGATGAGCTGTGACGGGGAAGGAGCCTGCTCAGAGCTGCTGTGTCTATGTGGCCTCCCATGTGGAT
CCAGGCAGCCATATTTGGGGACACCACCTCTCTGCTGGCTAGGTCCTGCCATGATCTTCTCTTTCCCTATGTGATTG
TCCGAGTGTGGGAGGCTCTTGGGTGTTTCCTGGGCTCTGCTGCACTTGGTCACCACTCAGCACAGGAAGTGTCCTC
GTGTACTCAGTAGGCAGCCATGTCTTGAATAGTGTTGACCCAGGCCCTTGGCTGCCCACAGTGTGGTTGTACTTGA
TTGAGCCCCTGAGCTTCTCAGTGGGTGACACCTTCTGTCTTTCCTTATCAGCGGATCGTGTCAAAAAAGGCTTTGA
CTTCCAGTGGCCACAACCTGACAAGCCTATGTTCTTCTACGTGACGCAGGGCCAGGAGGAGATTGCCAGCTCTGGC
ACATCCTACCTCAACAGGTGTGCAGCTGCGTCTCTGGTATGGAGCCATTCTCACTCACCCTCGGCTCCAACCCGAG
ACCCACAGCATCTTACTCCTTGGGTTGCTCTGCTTGTTAACAGCATGTGAGGGAAGACGCAAACAGGCTCTTGTTT
CTCCTGGGGCCTCAAAATGACAGGGGCGGGCAACTATCATGTGGCCTCCTGTAACCCCTTTGGTTACTGGAGGTCT
GCCAGGCTGGGGAACCTGTGAGGAGCCTTTTCACTGACAGCCAGATGTTCTCAGGACGGAGGCAGCCAATGTGGAG
AAGATAACTACGAAGCTGTTGAAGGCAGGTGCAAAGCCTGACCAGATCGGCATCATCACCCCCTACGAGGGCCAGC
GCTCTTACTTGGTGCAGTACATGCAGTTCAGCGGCTCCCTGCACACAAAGCTCTACCAGGTACCCATACCCAGCA
GTTAGGAGAGAGCGCATGAGCACACGTCATGACACACAGGTCAGCCTTGGGCTACTGACCTGGCTGGAGGCAAAAG
TAGAAAGAGTGTGGTGCTGTGTCAGCACTTCAGTGACATGACCAGGTGGGTCTTCATGAATTTGAGGTGGTCAGCC
TTGATTGAGAGCTTCAAGGCAGCCAGGGCTGTTCAGTAAGGCTTTGTCTCAAAGAAAGAGCAGCCCACGGCTAGAC
AGGAAGGGGCAGGACAGCTGGGCCCACCTGAGGGGCATGGTACTTGTGACAGATGCAGAGCTGTGGTTGGTTATAC
CATGGAGCCTACTCAGCATTTGCTTCATTGGGCCTGTGGTATCTCTATTATTGGGGACTCTTGTAGCATCTGGCTA
TAATGATGCAGCTAAAGGAAGAGACAGGAGAACGAGGGGCCGGGATATGGCTGACAGGACACTTGTCTCATTCAGG
AAGTGGAGATTGCCAGTGTGGACGCCTTCCAGGGCCGGGAGAAGGACTTCATCATTCTGTCCTGCGTGCGCGCCAA
TGAACATCAGGGCATTGGGTTCCTAAACGACCCCGGCGTCTGAATGTGGCTCTCACCAGAGCAAGGTAGGCCGCT
GCCCATCACTACCATCCACCCTCCAGCCAAAACAAGAAGCCCCCCCCCCTGTGATTCATTTTACTCATATCTGTCC
TGGGAGTACATGTGCATGCTGGCACCCCATCTTGAGAACTGGGCACTATGGCCTACCTGCTGCCTTACTGCTTCAA
GAACTCAACTACAAGATCCTATAGGACAGATTTAGCTCATGATCAAGAGAGGCCATTTAGAGAGCTGCGAATCAC
ACCCAGAGCTCTCACTGCTGCTTAAGTGCTACCTCATGTCTTAGCATCCTGCTCTTCACATTCAAGGTGCTAACCC
TAGACAGTGGAGTTCAGTAGGTGTGGCCATGGGCTCAGCATTTTGATTGCCCTGCAGATATGGCGTGATCATTGTG
GGTAACCCAAAGGCCCTGTCGAAGCAGCCCCTGTGGAATCACCTGCTGAGCTACTACAAGGAACAGAAGGCGCTAG
TGGAAGGGCCGCTCAACAACCTACGTGAGAGCCTCATGCAGTTCAGCAAGCCTCGCAAACTTGTCAACACTGTCAA
CCCGGTGGGCCTAGGGGCTGGCCTGGGACCTGGGAAAGCTGGGAGCTCTTAGCCTCTGCTGCTGTTGACTGACACA
TTCCTCACTCTTATGCCACCCTGCAGGGTGCCCGCTTCATGACTACTGCCATGTACGATGCCCGTGAGGCCATCAT
CCCCGGGTCTGTCTATGACCGCAGCAGCCAGGGTGAGTCTTCCTGGCCAGAACCCATGTGTTTATCTTCCCACGTC
CCACTCCGAACCTGTTGCCCCATGGGTGGCCTCCGTCTGGAACTTGTCCAGTAGCTTCTGTAGCTTCTCCAACCAG
GTCCCCAAGAGCTGTTCTGGCCTCAGCTAGTGGTTTGGGCCATGATCCCTTTAGAACTGCTAAGGCCACCTGTCTG
CCTGAGTGCTGCTGCCCTTGTATCCTGCAACAAACCGTGTCTACCTCAGCTAGGCTGGCCTCTGCTTTCTGGAAG
CTTCCAAGTTTGTCTAGAAAGTTCCATCGTGGCCAGATCTCACCAACCCTTCTGCCATTTCTTACCCTCTACCAGC
ACTCTGCATGTCAAGACACACTCGACCCTCCGACTTGTCTGGCTGGCCCAGCAGCTAGTTCATGGCAGCCAGTGTC
CACTGGAGCCCTGCATCTGACTCAAATGTTTTGCAGGCCGGCCCTCGAACATGTACTTCCAGACCCATGACCAGAT
CAGTATGATCAGCGCAGGCCCCAGCCACGTGGCTGCCATGAACATCCCTATTCCCTTCAACTTGGTCATGCCTCCC
ATGCCGCCACCTGGCTACTTCGGACAGGCCAACGGGCCGGCAGCTGGTAAGCGGTTTTATCTCTACTGCCCAGGCT
CTCCTCCTAGCTTTAGGTAGACCTTGCCATATTTCACTGCTGTCTTTCAGGTCGGGGCACCCCAAAAACCAAGACT
GGCCGTGGGGGCCGCCAGAAGAACCGCTTTGGGCTTCCTGGGCCCAGCCAGACCACCCTTCCCAACAGCCAGGCCA
GCCAGGACGTGGCCTCCCAGCCCTTTTCACAGGGTGCCCTCACACAGGGTTACGTGTCCATGAGCCAGCCCTCTCA
GATGAGCCAGCCTGGCCTCTCCCAGCCAGAACTGTCCCAGGTGGGCTGCATCCTACAGCAGAGAAAGGGGGTGGA
GGGGTGAGGGGACACATGAGACCATGATGCTGCCTTTCTGAAGGGTGAATGAACTCTACTGCTATGGATCTGAACC
TGTCACCCTGCTACTCTGGCTGCAGTATGGGGTTTCTTCCCATCCTCGGGTCTGCGGACTGGGTGGCTGTGGGCTA
CTAGCTTTCCTGGCCATGTTCACACTACTTTTGCCTTTCAGGACAGCTACCTCGGTGATGAGTTTAAATCACAGAT
TGACGTGGCACTCTCACAAGACTCCACATACCAGGGAGAGCGGGCATACCAGCACGGCGGGGTCACCGGGCTGTCC
CAGTACTAGAAGGCAAGTGCCCTGGTGGGTTCAGCTCTCTGCACACGTGTGCAAACAGGGTCTTCCCAGACAGACT
GGGCAAGTAGATATGGTGTGTTGGCAGGTCCTGCCTCTACTGGCCCTGACACCTCTAACCCTGTCCCTGATCACAG
GTAGCGGAGGAAGAGCTAAGCTATGTGGCTTAGTCTATCAGCATCTTATTCTGGGTAATAAAAAATAAAATAAAT
GGATACCTGTTTTCCACTGCTAAAACTGAAGCACCACTGTGTGAGCAGCCGAGGAGAGGAGAGGAAAGAGGAGCGA
GAGCGAGCAGAGAGCGGCCAGGGAGGACGACAGAGCGGAGCGCCGAGGAGGCGGCCCCCCTGTGGCGGCGAGAG
GAGAGAGGCCCGCACCGCTGCGAGGCCGGCCCAGCCCGTGCCCGCCAGAGGGAGAGGCCTCGCCAGGACCGGCCC
CGCTGGTCTTTTTCTTTGTTTCTCGTGATTGAGGGGCTACGTTTTAGCAGGACGAACTTCGCGTTTCTGTGCCCAA
GCGGGCGGCCAGGAGCATCAGTGCGCGGTCCCAGCGCTAAGGGGTTTCATTTAAAGAAAATACGGTGTTTGGGGTT
TTTCTGGTTTTCCTTTTTTTTTTTCTTTTTTTTGGTTTTTTTTTGTTTGTTGGTTTTTTTTTTTTTTTTTTTT
TCTTTTTGGTTTTCCTTTCCTCCCCCCTACCCCCTTCAAAGATTCTTTCAAAGGAGTATGGGAAGTACTTGGATCG
GTTTGTCTCTAGAGACCTGACTGTTAAACCTGAGAGATGCGAGAAGCTTCCGGGAAAGGCAGCGCTGAGAAGCCTG
AGCCCCGCAGCCTGGGATCACCGCCTGCACCACAGCCGGAGGATTTGTTTTGGAGTTTGAGCTTCAGAGGCCACAG
GCGAATCGTGAGCACGGCCTGCGGGTTCTTCCCCATCGAGGGGTGGAGGCCTCATTGTTTGGGCGCCCTGCCCCGG
ACCCCACCTCCCCGCGGAGCCACCCAACCCTACCCAGGAAACCTGGCCAACGAAATGGAATTTAATTTTTAGCAA
```

FIG. 4C

Exon positions:

murine RNT1 genomic sequence

Exons
154-293
1313-1402
2561-2728
3098-3278
4027-4188
4639-4723
4897-4996
5306-5414
5499-5658
5734-5852
6154-6318
6395-6509
7083-7698
8944-9062
9328-9483
9956-10100
10471-10644
10743-10826
11287-11448
11529-11744
11974-12090 murine amino acid sequence: SEQ ID NO. 2

FIG. 4D amino acid sequences for page 17:

```
PEGILQNGAVDDSVAKTSQLLAEK    (80-103)
RAKCKE      (162-167)
GVDEEPQHV       (184-192)
VIIKCQ      (453-458)
QIRNMDSMP       (564-572)
VKKGFD      (731-736)
RESLMQFSK       (907-915)
GARFMTTAMYDAREAIIPGSVY      (926-947)
SQDSTYQGERAYQHGGVTGLSQ      (1096-1117)
```

FIG. 4E

MAMMALIAN REGULATOR OF NONSENSE-MEDIATED RNA DECAY

This application is a divisional of U.S. application Ser. No. 08/724,354 filed Oct. 1, 1996, now pending, which claims the benefit of priority of U.S. Provisional Application Ser. No. 60/016,482 filed Apr. 29, 1996.

The present invention was made with United States Government support by National Institutes of Health (NIH) grants AR41135 and HG00971. The United States Government may have certain rights associated with this invention.

FIELD OF THE INVENTION

This invention relates generally to compositions and methods for inhibiting nonsense-mediated RNA decay in a cell.

BACKGROUND OF THE INVENTION

DESCRIPTION OF RELATED ART

The following is a general description of art relevant to the present invention. None is admitted to be prior art to the invention.

All organisms possess the ability to detect and degrade RNA transcripts that contain a premature translation stop codon. Such RNA transcripts are termed "nonsense" transcripts, and the cellular process of degrading these transcripts is termed nonsense-mediated RNA decay (NMRD). Although NMRD has been studied extensively in yeast, mammalian factors that participate in NMRD have not been described previously. In yeast, the protein Upf1, encoded by the UPF1 gene, is thought to be involved in NMRD (Leeds et al., 1992, Csaplinski et al., 1995). Upf1 shares a high degree of sequence homology with Sen1 of S. cerevisiae, which mediates tRNA splicing, and Mov-10, which is a mouse protein of unknown function. Two additional factors in yeast. Upf2 and Upf3, also are essential for NMRD.

Several factors suggest that NMRD differs substantially between yeast and mammals. For example, while translation is thought to be involved in NMRD in yeast, several observations suggest that translation does not play a similar role in mammalian cells (Peltz et al., 1994). First, for many genes and mutations, the reduction in the level of nonsense transcripts in the cytoplasm is coupled with a similar reduction in the level of nonsense transcripts in the nucleus of the cell. Examples of transcripts that are reduced in level in both the cytoplasm and nucleus, despite normal rates of transcription. include transcripts encoding β-globin, DHFR, TPI, MUP, and avian sarcoma virus src. A second indication that mammalian NMRD may differ from yeast NMRD is the suggestion that NMRD occurs in the nucleus, rather than cytoplasm, of mammalian cells (Maquat, 1995). The factors that suggest that NMRD occurs in the nucleus of mammalian cells include the observations that: (i) NMRD is dependent upon intron sequences; (ii) most transcripts derived from intronless minigenes are immune to NMRD; (iii) once nonsense transcripts reach the cytoplasm and are bound by polysomes, they display a normal degree of stability; and (iv) nonsense codons influence pre-mRNA processing. A particularly compelling observation is that nonsense mutations can alter the ability of a cell's RNA splicing machinery to recognize exons; this process occurs within the nucleus, and is not dependent upon ribosomes (Dietz et al., 1993a; Dietz and Kendzior, 1994).

NMRD has a distinct physiologic role in intracellular processing, that is, to reduce the presence of abnormal proteins within cells. In the absence of NMRD, premature termination codons (PTCs) that result from nonsense mutations can lead to the production of proteins which are truncated versions of wild-type proteins. PTCs resulting from frameshifts, gene rearrangements, or the retention of introns can, in the absence of normal functioning NMRD, produce aberrant proteins which differ in sequence from the wild-type protein. Such deviant proteins are implicated in disease states. It is anticipated that mammalian organisms containing mutations in RENT1 are likely to suffer from syndromes associated with the excessive build up of these abnormal proteins such as Marfan Syndrome, accelerated aging or various cancers. Thus, RENT1 plays an important role in the control of NMRD and consequently for the prevention of disease states due to the expression of mutant proteins.

SUMMARY OF THE INVENTION

Applicant has isolated and characterized a human complementary DNA which encodes a protein designated rent1, that regulates the stability of transcripts containing nonsense mutations. Applicant has shown that the expression of dominant negative forms of rent1 (i.e. mutant proteins that interfere with the function of normal protein) produce stabilization and accumulation of nonsense transcripts. Applicant has also shown that expression of antisense regulatory molecules that inhibit expression of rent1 result in the stabilization of nonsense transcripts. Applicant has demonstrated that rent1 is expressed in all human tissues tested, as would be predicted for an essential component of the ubiquitous NMRD pathway.

In addition to cloning and sequencing the human RENT1 cDNA, Applicant has also cloned and sequenced in their entirety the murine Rent1 cDNA and genomic sequences. Applicant has shown that rent1 is highly homologous to yeast Upf1p, a known effector of nonsense transcript degradation. Applicant has shown that expression of a protein composed largely of the human protein sequence restores NMRD in yeast deficient for NMRD functions. Applicant has cloned the mouse gene encoding rent1 and has shown that the human and mouse proteins are nearly identical. Applicant has concluded that rent1 is the first mammalian regulator of nonsense transcript stability to be identified.

Applicant has shown that the NMRD pathway can influence the severity of diseases caused by premature termination codons in other genes. Modification of the efficiency of NMRD through manipulation of rent1 or proteins of related function is proposed as a novel therapeutic strategy. Inhibition of rent1 expression or function is used to stabilize nonsense transcripts that encode proteins that retain some of their intended function. Alternatively, augmentation of the level of expression of rent1 or its function and increase in efficiency of NMRD is used to more efficiently and completely degrade nonsense transcripts that encode deleterious proteins such as those with harmful dominant negative or gain-of-function effects.

Modification of the efficiently of NMRD is also proposed as a means to identify new disease genes. If NMRD is experimentally impaired in a cell line harboring a premature termination codon in an unknown disease gene, then nonsense transcripts derived from that disease gene will be stabilized and accumulate within the cells. By identifying the transcript that is enriched upon inhibition of NMRD, the identification of the disease gene is greatly facilitated.

The invention provides substantially pure rent1 polypeptides, fragments thereof, nucleic acid sequences encoding rent1 or fragments thereof, methods of detecting modulators of rent1 or NMRD, methods of administering formulations capable of gene delivery and gene expression of RENT1nucleic acid, methods of hybridization for RENT1nucleic acid, and transgenic animals created using RENT1nucleic acid sequences.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

FIGS. 1A–1C show the alignment of the amino acid sequence of rent1 with homologous proteins. FIG. 1A, Amino terminus aligned with the specified regions of yeast (y) heat shock protein Sis1 and *B. napus* (b) RNA-binding protein GRP10. FIG. 1B, Body aligned with the specified region of *S. cerevisiae* Upf1p. FIG 1C, Carboxy terminus aligned with the specified regions of human or mouse (h/m) RNA-binding protein Ews. Identical and conserved residues are separated by vertical lines (|) and dots (.), respectively. Underlined regions serve putative nucleotide-binding (segments 1 and 2) and NTP-hydrolysis (segments 3 through 5) functions. Bold and underlined regions are highly conserved among members of helicase superfamily I. Crosses (†) occur above sites of demonstrated dominant-negative mutations in Upf1p. Italicized symbols above the human sequence indicate differences in the characterized region of murine sequence, corresponding to amino acid 78 to 1118 in the human protein and flanked by ≧ and ≦ symbols in the figure.

FIGS. 4A–4E show the murine RENT1 complete genomic and amino acid sequence.

DETAILED DESCRIPTION OF THE INVENTION

Figure 2:
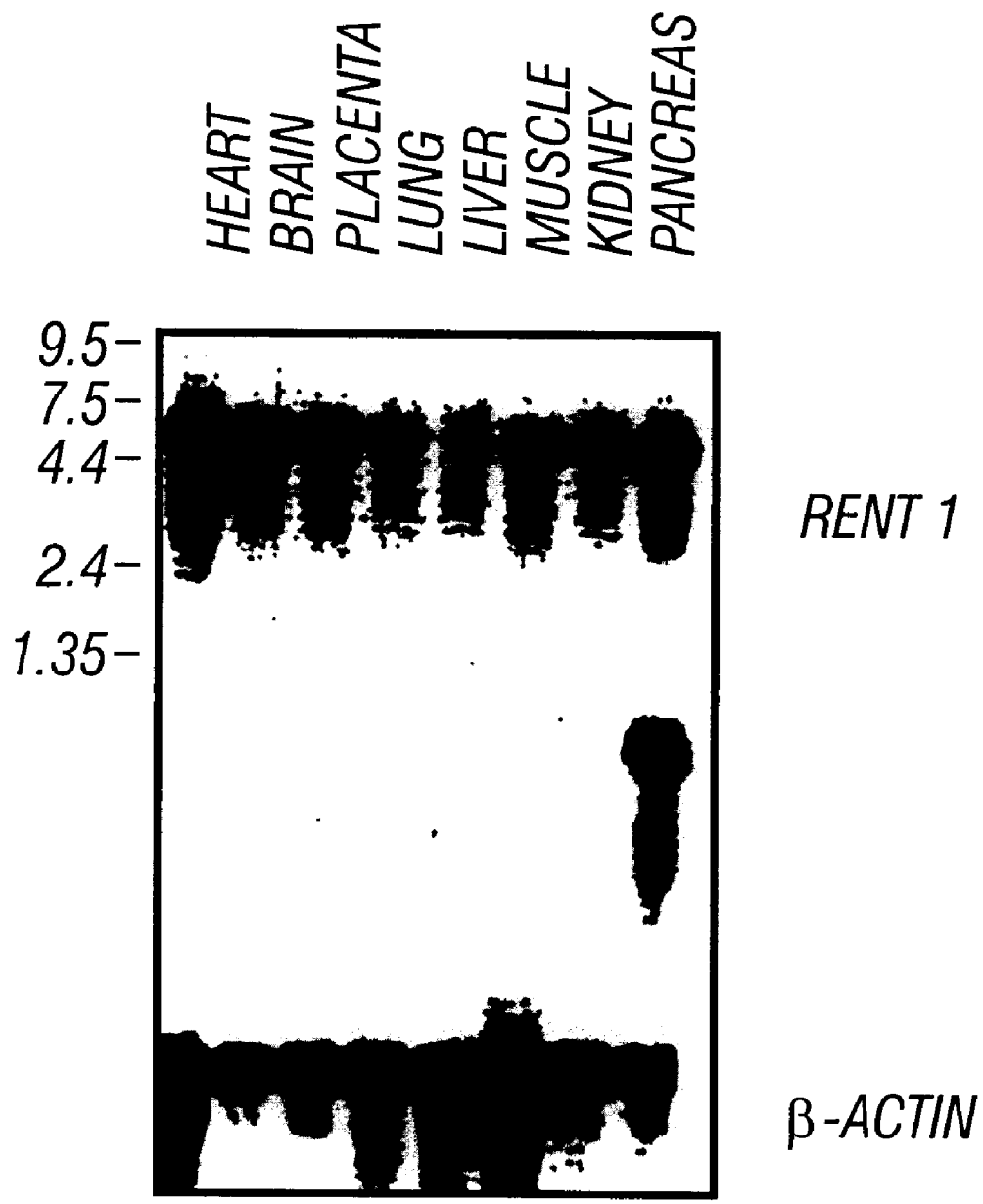
FIG. 2 shows a Northern blot analysis of the expression of rent1 in human tissues. Poly(A) RNA shows a predominant transcript size of approximately 5.4 kb in all of the indicated adult tissues. A less intense signal is seen at approximately 3.7 kb in all lanes, with an additional and significantly smaller hybridizing transcript unique to the pancreas. Additional tissues tested (spleen, thymus, prostate, testis, ovary, small intestine, colon, and peripheral blood leukocyte) all showed predominant ~5.4 kb and less intense 3.7 kb bands, except in testes where equally intense signals were observed.

Before the present nucleic and amino acid sequences, compositions, formulations and methods and uses thereof are described, it is to be understood that this invention is not limited to the particular compositions, formulations, sequences and methodologies described herein as such compositions, formulations, sequences and metlhodologies may vary. It is also to be understood that the terminology used herein is for the purpose of describing particular embodiments only, and that the terminology used herein is not intended to limit the scope of the present invention which will be limited only by the appended claims.

Description of the Preferred Embodiments

The invention provides substantially pure polynucleotides encoding the rent1 protein or fragments thereof. These polynucleotides include DNA, cDNA and RNA sequences which encode rent1. All polynucleotides encoding all or a portion of rent1 are also included herein, as long as they encode a polypeptide with rent1 activity as described herein or a functional fragment of a rent1 molecule. Such polynucleotides include naturally occurring, synthetic, and intentionally manipulated polynucleotides. For example, rent1 polynucleotide may be subjected to site-directed mutagenesis. The polynucleotide sequence for rent1 also includes antisense, nonsense, or missense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of rent1 polypeptide or a part thereof encoded by the nucleotide sequence is functionally unchanged.

The invention also provides isolated nucleic acid molecules that encode the rent1 polypeptides described above, as well as fragments thereof. These nucleic acids can contain naturally occurring nucleotide sequences or sequences that differ from those of the naturally occurring nucleic acids that encode rent1, but encode the same amino acids, due to the degeneracy of the genetic code. The nucleic acids of the invention can contain DNA or RNA nucleotides, or combinations or modifications thereof.

The term "isolated nucleic acid" as used herein means a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

The nucleic acid molecules of the invention can be used as templates in standard methods for production of RENT1 gene products (e.g., RENT1 RNAs and rent1 polypeptides; see below). In addition, the nucleic acid molecules that encode rent1 polypeptides (and fragments thereof) and related nucleic acids, such as (1) nucleic acids containing sequences that are complementary to, or that hybridize to, nucleic acids encoding rent1 polypeptides, or fragments thereof (e.g., fragments containing at least 9, 12, 15, 20, or 25 nucleotides); and (2) nucleic acids containing sequences that hybridize to sequences that are complementary to nucleic acids encoding rent1 polypeptides, or fragments thereof (e.g., fragments containing at least 9, 12, 15, 20, or 25 nucleotides); can be used in methods focused on their hybridization properties. For example, as is described in further detail below, such nucleic acid molecules can be used in the following methods: PCR methods for synthesizing RENT1 nucleic acids, methods for detecting the presence of RENT1 nucleic acid in a sample, screening methods for identifying nucleic acids encoding new RENT1 family members, and therapeutic methods. The term sample, as used herein, comprises fluid, blood, serum, plasma, cells, tissue, swabs, or secretions or other clinical samples as are commonly familiar to those of ordinary skill in the clinical arts.

The term "substantially pure" is used herein to describe a molecule, such as a polypeptide (e.g., a rent1 polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. One skilled in the art can purify rent1 polypeptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

Also included in the invention are polypeptides having sequences that are "conservative variations" of the sequence of a rent1 polypeptide. A "conservative variation" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine), or by one or more non-conservative substitutions, deletions, or insertions, provided that the polypeptide retains at least one rent1-specific activity or a rent1-specific epitope. For example, one or more amino acids can be deleted from a rent1 polypeptide, resulting in modification of the structure of the polypeptide, without significantly altering its biological activity. For example, amino- or carboxyl-terminal amino acids that are not required for rent1 biological activity, can be removed. Such modifications can result in the development of smaller active rent1 polypeptides.

The term "rent1" is used in accordance with the following definition: the terms rent1 and RENT1 (regulator of nonsense transcripts) refer to the gene and protein, respectively, from either the murine or human species as in FIG. 1 (SEQ ID NOS:1, 2, 3 or 4).

A "test composition", as used herein, is any composition such as a gene, a nucleic acid sequence, a polypeptide, peptide fragment or composition created through the use of a combinatorial library or other combinatorial process that can be assayed for its ability to function in a given capacity (e.g., as a rent1 co-factor, or rent1 interactor or rent1 modulator of nonsense mediated RNA decay (NMRD) using the rent1 pathway) or compound which mimics the activity of the rent1 polypeptide (e.g., peptidomimetics). Often, such a test composition, nucleic acid sequence or polypeptide is, because of its sequence or structure, suspected of being able to function in a given capacity. Nonetheless, randomly chosen "test" nucleic acid sequences, polypeptides or fragements thereof and compositions also can be used, and art-known techniques, such as expression of polypeptides from nucleic acid libraries, or PCR combinatorial generated polypeptides can be used to this end. A "co-factor" is any composition (e.g., a polypeptide, polypeptide derivative, or peptidomimetic) that is capable of modulating rent1 and influencing NMRD. Included are compositions that naturally induce NMRD via rent1; also included are compositions that do not naturally induce NMRD (e.g., artificial compositions and natural compositions that serve other purposes). The term "agonist" as used herein means any composition that is capable of increasing RENT1 mediated NMRD. Such an agonist need not bind rent1 to increase NMRD or to modulate NMRD via rent1. The term "antagonist" as used herein means any composition that is capable of decreasing the ability of rent1 or to induce NMRD via the rent1 pathway. An antagonist need not directly bind, or compete with, rent1 to modulate NMRD via the rent1 pathway.

"Formulation" means a composition capable of gene delivers and gene expression, that is, capable of delivering a nucleotide sequence to, or directly into, a target cell whereupon the formulation containing the nucleotide sequence is incorporated on the cytoplasmic side of the outermost membrane of the target cell and capable of achieving gene expression so that detectable levels of gene expression of the delivered nucleotide sequence are expressed in the target cell. More preferably, after delivery into the cytoplasmic side of the cell membrane the composition is subsequently transported, without undergoing endosomal or lytic degradation, into the nucleus of the target cell in a functional state capable of achieving gene expression so that detectable levels of gene expression of the delivered nucleotide sequence are expressed in the target cell. Expression levels of the gene or nucleotide sequence inside the target cell are capable of providing gene expression for a duration of time and in an amount such that the nucleotide product therein is capable of providing a biologically beneficially effective amount of gene product or in such an amount as to provide a functionally beneficial biological effect on the target cell. As used herein, the term formulation can refer to, but is not limited by (either explicitly or implicitly) the following examples: (1) liposome or liposome formulations or liposomal compositions either cationic, anionic or neutral in net character and net charge; (2) DNA, nucleic acid or a nucleic acid expression vector ionically complexed with a polycation/s and a ligand/s such that after attachment of the [DNA+Polycation+Ligand] composition to a cell surface receptor on a target cell via the ligand, the [DNA+Polycation+Ligand] composition is capable of being endocytosed into the target cell and the DNA is subsequently decoupled from the ligand and polycation and delivered to the cell nucleus in a functional condition for subsequent expression. Various alterations in the composition can be envisioned by those of ordinary skill in the art such as including peptide sequences which (a) prevent the composition from endosomal lysis after incorporation into the target cell by allowing the composition to leave the lysosomal vesicle, or (b) which act as a nuclear targeting agent, chaperoning the nucleic acid through the pores of the nuclear envelope and into the nucleus of the cell. Similar formulations, which have been previously described, are the asialoglycoprotein-polylysine conjugation (Wu and Wu, *J. Biol. Chem.* 263:14621, 1988; Wu et al., *J. Biol. Chem.* 264:16985, 1989); (3) naked nucleic acid; (4) compacted nucleic acid or a compacted formulation; or (5) plasmid or naked DNA which can be microinjected (Wolff et al., *Science* 247:1465, 1990); (6) nucleic acid in a viral or retroviral vector compositions; and (7) colloidal dispersions (Felglner et al., *Proc. Natl. Acad. Sci. USA* 48:7413, 1987; Ono et al., *Neuroscience Lett* 117:259, 1990; Brigham et al., *Am. J. Med. Sci.* 298:278, 1989; Staubinger and Papahadjopoulos, *Meth. Enz.* 101:512, 1983). One of ordinary skill in the art will recognize that other compositions for the delivery of nucleotide sequences to target cells may be envisioned.

"Gene delivery" means transportation or transfer of a composition or formulation inside of or into contact with a target cell so that the composition or formulation is capable of being taken up by means of a cytotic process (i.e., pinocytosis, endocytosis, NMRD, macrocytosis etc.) into the interior or cytoplasmic side of the outermost cell membrane of the target cell where it can subsequently be transported into the nucleus of the cell in such functional condition that it is capable of achieving detectable gene expression for a period of time and in such an amount to produce a detectable biologically beneficial effect.

"Gene expression" means the process, after delivery into a target cell, by which a nucleotide sequence undergoes successful transcription and translation such that detectable levels of the delivered nucleotide sequence are expressed in an amount and over a time period so that a functional biological effect is achieved. As used herein, gene expression can refer to, but is not restricted by (either explicitly or implicitly) the following examples. A RENT1 nucleic acid sequence is delivered and expressed in targeted cells such that the targeted cells increase, decrease, or are inhibited in the production of rent1 protein or RENT1 RNA, thus: either enhancing NMRD, inhibiting NMRD, or modulating NMRD, and subsequently leading to a beneficially detectable biological effect or outcome. "Expressible genetic construct" means a construct which has the RENT1 gene positioned for expression. "Operably linked" means that a gene and a regulatory sequence(s) are connected to permit expression of the RENT1 gene when the appropriate molecules (e.g., transcriptional activato proteins) are bound to the regulatory sequence(s). "Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familar to those in the art which can produce an organism carrying an introduced transgene or one in which an endogenous gene has been rendered non-functional or knocked out.

"Promoter" means the minimal nucleotide sequence sufficient to direct transcription. Also included in the invention are those promoter elements that are sufficient to render promoter-dependent gene expression controllable for cell-type specific, tissue specific, or inducible by external signals or agents; such elements may be located in the 5' or 3' regions of the native gene. "Detectably-labeled" means any means for marking and identifying the presence of a molecule, e.g., an oligonucleotide probe or primer, an antibody or fragment thereof, a protein or fragment thereof, a gene or fragment thereof, or a cDNA molecule. Methods for detectably-labeling are well known in the art and include, without limitation, radioactive labeling (e.g., with an isotope such as $^{32}P$ or $^{35}S$) and nonradioactive labeling (e.g., chemiluminescent labeling, e.g., fluorescent labeling).

"Purified antibody" means antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., a rent1 specific antibody. A purified antibody may be obtained, for example, by affinity chromatography using recombinantly-produced protein or conserved motif peptides and standard techniques. The invention can employ not only intact monoclonal or polyclonal antibodies, but also an immunologically-active antibody fragment, such as a Fab' or (Fab')2 fragment, or a genetically engineered Fv fragment (Ladner et al., U.S. Pat. No. 4,946,788). "Specifically binds" means an antibody which recognizes and binds a specified protein but which does not substantially recognize and bind other molecules in a sample, e.g., a biological sample, which naturally includes protein.

"Therapeutically effective" as used herein, refers to an amount formulation that is of sufficient quantity to ameliorate the state of the patient so treated. "Ameliorate" refers to a lessening of the detrimental effect of the disease state or disorder in the patient receiving the therapy. The subject of the invention is preferably a human, however, it can be envisioned that any animal can be treated in the method of the instant invention. The term "modulate" means enhance, inhibit, alter, or modify the expression of RENT1 mRNA, nucleic acid, polypeptide or protein.

The invention also provides a method for determining whether a test agent or composition modulates NMRD in a cell. The method can be performed by (i) providing a cell that has RENT1; (ii) contacting the cell with a test agent or composition in the absence of the test agent or composition, activates the RENT1 in the cell; and (iii) detecting a change in the NMRD of the cell. In practicing the invention, the cell can be contacted with the test agent or composition either simultaneously or sequentially. An increase in NMRD indicates that the test agent or composition is an agonist of RENT1 while a decrease in NMRD indicates that the test agent or composition is an antagonist of rent1. If desired, the above-described method for identifying modulators of NMRD can be used to identify compositions, co-factors or other compositions within the NMRD pathway comprising RENT1 for use in this aspect of the invention. Any agent or composition can be used as a test agent or composition in practicing the invention; a preferred test agent or compositions include polypeptides and small organic agent or compositions. Although sequence or structural homology can provide a basis for suspecting that a test agent or composition can modulate NMRD via RENT1 in a cell, randomly chosen test agent or compositions also are suitable for use in the invention. Art-known methods for randomly generating an agent or compositions (e.g., expression of polypeptides from nucleic acid libraries) can be used to produce suitable test agent or compositions. Those skilled in the art will recognize alternative techniques can be used in lieu of the particular techniques described herein.

The invention also provides a method for detecting novel co-factors or inhibitors which bind RENT1 which comprises contacting a sample comprising RENT1 with test compositions and measuring the change in NMRD after application of the test composition. The rent1 protein of the instant invention is useful in a screening method for identifying novel test compounds or novel test compositions which affect NMRD via rent1. Thus, in another embodiment, the invention provides a method for screening test compositions comprising incubating components, which include the test composition, and rent1 under conditions sufficient to allow the components to interact, then subsequently measuring the effect the test composition has on NMRD in a test cell. The observed effect on NMRD between rent1 and a composition may be either agonistic or antagonistic. Preferably, the polypeptide encoding the rent1 is the polypeptide or functional fragment thereof of SEQ ID NO:2 or 4 or a synthetic peptide which has the biological activity of the rent1 protein.

The invention also includes fragments of rent1 polypeptides, that retain at least one rent1-specific activity or epitope. For example, a rent1 polypeptide fragment containing, e.g., at least 8–10 amino acids can be used as an immunogen in the production of rent1-specific antibodies. Such fragments can easily be identified by comparing the sequence of RENT1 by reference to FIG. 1. In addition to their use as peptide immunogens, rent1 fragments can be used in immunoassays, such as ELISAs, to detect the presence of rent1-specific antibodies in samples.

The rent1 polypeptides of the invention can be obtained using any of several standard methods. For example, rent1 polypeptides can be produced in a standard recombinant expression systems (see below), chemically synthesized (this approach may be limited to small rent1 peptide fragments), or purified from tissues in which they are naturally expressed (see, e.g., Ausubel, et al., supra).

The invention also provides isolated nucleic acid molecules that encode the rent1 polypeptides described above, as well as fragments thereof. These nucleic acids can contain naturally occurring nucleotide sequences, or sequences that differ from those of the naturally occurring nucleic acids that encode rent1s, but encode the same amino acids, due to the degeneracy of the genetic code or amino acids which are conservative variations. The nucleic acids of the invention can contain DNA or RNA nucleotides, or combinations or modifications thereof.

All organisms that have been studied to date possess the ability to detect and degrade RNA transcripts that contain a premature signal for the termination of translation. The process of nonsense-mediated RNA decay (NMRD) has been most comprehensively studied in the yeast *Saccharomyces cerevisiae*. Essential components of the yeast pathway include at least 3 trans-acting actors (UPF1-3). The human homologue of yeast UPF1, is RNT1 (regulator of nonsense transcripts). The invention includes methods for identifying nucleic acid molecules that encode members of mammalian rent1 homologues. In these methods, a sample, e.g., a nucleic acid library, such as a cDNA library, that contains a nucleic acid encoding a rent1 polypeptide is screened with a RENT1-specific probe, e.g. a RENT1-specific nucleic acid probe. RENT1-specific nucleic acid probes are nucleic acid molecules (e.g., molecules containing DNA or RNA nucleotides, or combinations or modifications thereof) that specifically hybridize to nucleic acids encoding rent1 polypeptides, or to complementary sequences thereof.

Because RENT1 is closely related to the UPF family in yeast, the term "RENT1-specific probe," in the context of this invention, refers to probes that bind to nucleic acids encoding rent1 polypeptides, or to complementary sequences thereof, to a detectably greater extent than to nucleic acids encoding UPF sequences, or to complementary sequences thereof. The term "RENT1-specific probe" thus includes probes that can bind to nucleic acids encoding rent1 polypeptides (or to complementary sequences thereof), but not to nucleic acids encoding UPF sequences (or to complementary sequences thereof, to an appreciable extent.

The invention facilitates production of RENT1-specific nucleic acid probes. Methods for obtaining such probes can be designed based on the amino acid sequence alignments shown in FIG. 1. The probes, which can contain at least 9, e.g., at least 12, 15, 25, 35, 50, 100, or 150 nucleotides, can be produced using any of several standard methods (see, e.g., Ausubel, et al., supra). For example, preferably, the probes are generated using PCR amplification methods, such as those described below. In these methods, primers are designed that correspond to RENT1 sequences, which can include rent1-specific amino acids, and the resulting PCR product is used as a probe to screen a nucleic acid library, such as a cDNA library.

As is known in the art, PCR primers are typically designed to contain at least 15 nucleotides, for example 15–30 nucleotides. The design of RENT1-specific primers containing 21 nucleotides, which encode rent1 peptides containing 7 amino acids, are described as follows. Preferably, most or all of the nucleotides in such a probe encode rent1-conserved amino acids, including rent1-specific amino acids. For example, primers containing sequences encoding peptides containing at least 40% rent1-conserved amino acids can be used. Such a primer, containing 21 nucleotides, can include sequences encoding at least 3/7, 4/7, 5/7, 6/7, or 7/7 rent1-conserved amino acids. As can be determined by analysis of FIG. 1, in the case of a 21 nucleotide primer, encoding 7 amino acids, up to 5 amino acids can be rent1-specific. Thus, the primer can contain sequences encoding at least one rent1-specific amino acid, for example, up to 5 rent1-specific amino acids. Once rent1-specific amino acid sequences are selected as templates against which primer sequences are to be designed, the primers can be synthesized using, e.g., standard chemical methods. As is described above, due to the degeneracy of the genetic code, such primers should be designed to include appropriate degenerate sequences, as can readily be determined by one skilled in the art.

Based on the guidelines presented above, examples of rent1-conserved amino acid peptides that can be used as templates for the design of RENT1-specific primers are as follows. Additional examples can be found by analysis of sequence alignments of rent1 polypeptides. Primers can be designed, for example, based on 5–10 amino acid regions of the rent1 peptide, depending on the lengths of the primers desired. For example, primers can be designed to correspond to 7 consecutive amino acids of any of the segments shown below.

1. QVDFVQKSTSFDRMQSALKTFAV (SEQ ID NO: 5) (corresponding to amino acids 411–434 of human rent1)
2. LSLIOGPPGTGKTVTSATIVYHLARQDN (SEQ ID NO: 6) (corresponding to amino acids 487–515 of human rent1)
3. HIVNHLVRAKCKEVTLHKDGP(SEQ ID NO: 7) (corresponding to amino acids 488–511 of human rent1)
4. AGQLDAQVGPEGILQNGAVDDSVAKT (SEQ ID NO: 8; corresponding to amino acids 72–97 of human rent1 amino terminus)
5. ILIDESTQATEPECMVPVVLGAKQLILVGD (SEQ ID NO: 9; corresponding to amino acids 634–663 of human rent1)
6. SMSQPSQMSQPGLSQPELSQ (SEQ ID NO: 10; corresponding to amino acids 1061–1075 of human rent1 - carboxy terminus)

As is described above, RENT1-specific primers, for example primers based on the rent1-specific peptides shown above, or portions thereof, can be used in PCR reactions to generate RENT1-specific probes, which can be used in standard screening methods to identify nucleic acids encoding rent1 family members (see, e.g., Ausubel, et al., supra).

In addition to RENT1-specific nucleic acid probes, rent1-specific polypeptide probes, such as rent1-specific antibodies, can be used to screen samples, e.g., expression libraries, for nucleic acids encoding novel rent1 polypeptides, or portions thereof. For example, an antibody that specifically binds to a rent1-specific peptide can be used in this method. Methods for carrying out such screening are well known in the art (see, e.g., Ausubel, et al., sulpra).

The sequences of a pair of nucleic acid molecules (or two regions within a single nucleic acid molecule) are said to be "complementary" to each other if base pairing interactions can occur between each nucleotide of one of the members of the pair and each nucleotide of the other member of the pair. A pair of nucleic acid molecules (or two regions within a single nucleic acid molecule) are said to "hybridize" to each other if they form a duplex by base pairing interactions between them. As is known in the art, hybridization between nucleic acid pairs does not require complete complementarity between the hybridizing regions, but only that there is a sufficient level of base pairing to maintain the duplex under the hybridization conditions used.

Hybridization reactions are typically carried out under low to moderate stringency conditions, in which specific and some non-specific interactions can occur. After hybridization, washing can be carried out under moderate or high stringency conditions to eliminate non-specific binding. As is known in the art, optimal washing conditions can be determined empirically, e.g., by gradually increasing the stringency. Condition parameters that can be changed to affect stringency include, e.g., temperature and salt concentration. In general, the lower the salt concentration and the higher the temperature, the higher the stringency. For example, washing can be initiated at a low temperature (e.g., room temperature) using a solution containing an equivalent or lower salt concentration as the hybridization solution. Subsequent washing can be carried out using progressively warmer solutions having the same salt solution. Alternatively, the salt concentration can be lowered and the temperature maintained in the washing step or the salt concentration can be lowered and the temperature increased. Additional parameters can be altered to affect stringency, including, e.g., the use of a destabilizing agent, such as formamide.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1%/ SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The nucleic acid molecules of the invention can be obtained by any of several standard methods. For example, the molecules can be produced using standard recombinant, enzymatic (e.g., PCR or reverse transcription (RT)/PCR methods), and chemical (e.g., phosphoramidite-based synthesis) methods. In addition, they can be isolated from samples, such as nucleic acid libraries and tissue samples, using standard hybridization methods. For example, as described above, using standard methods, genomic or cDNA libraries can be hybridized with nucleic acid probes corresponding to RENT1 nucleic acid sequences to detect the presence of a homologous nucleotide sequence in the library (see, e.g., Ausubel, et al., supra). These methods are described in more detail above. Also as described above, nucleic acids encoding polypeptides containing at least one rent1 epitope, such as a rent1-specific epitope, can also be identified by screening a cDNA expression library, such as a library contained in lambda gt 11, with a rent1-specific antibody as a probe. Such antibodies can be either polyclonal or monoclonal and are produced using standard methods (see, e.g., Harlow and Lane, *Antibodies: A Laboratory Manual*, Cold Spring Harbor Laboratory Press, Cold Spring Harbor, N.Y., 1988).

rent1-specific antibodies and nucleic acids can be used as probes in methods to detect the presence of a rent1 polypeptide (using an antibody) or nucleic acid (using a nucleic acid probe) in a sample or specific cell type. In these methods, a rent1-specific antibody or nucleic acid probe is contacted with a sample from a patient suspected of having a rent1-associated disorder, and specific binding of the antibody or nucleic acid probe to the sample detected. The level of rent1 polypeptide or nucleic acid present in the suspect sample can be compared with the level in a control sample, e.g., an equivalent sample from an unaffected individual, to determine whether the patient has a rent1-associated disorder. rent1 polypeptides, or fragments thereof, can also be used as probes in diagnostic methods, for example, to detect the presence of rent1-specific antibodies in samples. Additionally, rent1-specific antibodies could be used to detect novel cofactors which have formed a complex with rent1 or fragment thereof.

The RENT1-specific nucleic acid probes can be labeled with a compound that facilitates detection of binding to the RENT1 nucleic acid in the sample. For example, the probe can contain biotinylated nucleotides, to which detectably labeled avidin conjugates (e.g., horse-radish peroxidase-conjugated avidin) can blind. Radiolabeled nucleic acid probes can also be used. These probes can be used in nucleic acid hybridization assays to detect altered levels of RENT1s in a sample. For example, in situ hybridization, RNASE protection, and Northern Blot methods can be used. Other standard nucleic acid detection methods that can be used in the invention are known to those of skill in the art (see, e.g., Ausubel, et al., supra). In addition, when the diagnostic molecule is a nucleic acid, it can be amplified prior to binding with a RENT1-specific probe. Preferably, PCR is used, but other nucleic acid amplification methods, such as the ligase chain reaction (LCR), ligated activated transcription (LAT), and nucleic acid sequence-based amplification (NASBA) methods can be used.

Additionally, RENT1-specific nucleic acid probes could be used to detect unique polypeptide expression clones from nucleic acid libraries such as expression libraries for fragments of the RENT1 nucleic acid sequence or homologues of the RENT1 nucleic acid sequence. RENT1-specific nucleic acid probes could be used to detect expression clones used to randomly generate compounds (e.g., expression of polypeptides from nucleic acid libraries) that can be used to produce suitable test compounds of the instant invention. A cDNA expression library can be screened indirectly for rent1 peptides having at least one epitope, using antibodies specific for rent1 as described herein. Such antibodies can be either polyclonally or monoclonally derived and used to detect expression product indicative of the presence of RENT1 cDNA.

Specifically disclosed herein is a complete cDNA sequence containing the entire human RENT1 coding sequence and a complete cDNA sequence containing murine RENT1. Although divergence is seen at the extreme N- and C-termini, the large central regions of Upf1p and RENT1 (residues 60–853 and 121–917, respectively) show 58% identity and 80% conservation. Moreover, rent1 is the first identified mammalian protein that contains all of the putative functional elements found in Upf1p including the cysteine-rich zinc finger-like domains that may participate in nucleotide binding, the domains with putative NTPase activity, and the motifs common to members of helicase superfamily I.

The N-terminus of RENT1 contains a region composed entity of proline, glycine, and alanine (PGA) residues not found in Upf1p. While the function of this region is unknown, PGA-rich stretches have been found to act as direct transcriptional repressors. Alternatively, the helix-disturbing properties imposed by the high PG content may confer a favorable conformation to the molecule. If one excludes the PGA-rich region, certain similarities are evident between the N-termini of RENT1 and Upf1p. Both are relatively rich in serines and threonines (19 vs. 24%, respectively) and acidic residues (D or E; 22 vs. 1 8%, respectively), features commonly seen in nucleotide-binding proteins with transactivation or transcriptional regulation properties. Both C-termini are rich in serines and glutamines (21 vs. 18%, respectively) but the occurrence of the majority of these residues as SQ dipeptides (n=14) is unique to rent1. Many RNA recognition motif (RRM)-containing proteins have glutamine rich regions that are postulated to regulate multiple aspects of RNA processing. BLAST analysis of the divergent N- and C- terminal sequences of RENT1 reveals homology to multiple proteins that interact with RNA and regulate its processing. These include the Sis1 heat shock protein of yeast (p=5.6e-07), the Gr10 RNA-binding protein of B. napies (p=1.2e-04), and the human or mouse EWS RNA-binding protein (p=8.9e-03) (18–20).

The polynucleotide encoding RENT1 includes the niucleotide sequence in FIG. 1 (SEQ ID NO:1) as well as nucleic acid sequences complementary to that sequence. A complementary sequence may include an antisense nucleotide. When the sequence is RNA, the deoxynucleotides A, G, C, and T of FIG. 1 are replaced by ribonucleotides A, G, C, and U, respectively. Also included in the invention are fragments of the above-described nucleic acid sequences that are at least 9 bases in length, which is sufficient to permit the fragment to selectively hybridize to DNA that encodes the protein of FIG. 1 (SEQ ID NO:2) under physiological conditions.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features. Therefore, given a partial DNA sequence of the gene of interest, one of skill in the art would be able to prepare probes for isolation of a full length cDNA clone, without undue experimentation (see for example, Ausubel, et al., *Current Protocols in Molecular Biology*, Units 6.3–6.4, Greene Publ., current edition; Maniatis, et al., *Molecular Cloning*, Cold Spring Harbor Laboratories, current edition).

The development of specific DNA sequences encoding RENT1 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

DNA sequences encoding RENT1 can be expressed in vitro, in vivo or ex vivo by DNA transfer into a suitable target cell. "Target cells" are cells in which a vector can be propagated and its DNA expressed or in which a formulation can be delivered into a cell for subsequent gene expression. The term also includes any progeny of the subject target cell. It is understood that all progeny may not be identical to the parental cell since there may be mutations that occur during replication. However, such progeny are understood to be included when the term "target cell" is used. Methods of stable transfer, meaning that the foreign DNA is continuously maintained in the host, are known in the art.

In the present invention, the RENT1 polynucleotide sequences may be inserted into a recombinant expression vector construct. The term "recombinant expression vector construct" refers to a plasmid, virus or other vehicle known in the art that has been manipulated by insertion or incorporation of RENT1 genetic sequences. Such expression vectors or constructs contain a promoter sequence which facilitates the efficient transcription of the inserted genetic sequence of the host. The expression vector or construct typically contains an origin of replication, a promoter, as well as specific genes which allow phenotypic selection of the transformed cells. Vectors or constructs suitable for use in the present invention include, but are not limited to the T7-based expression vector for expression in bacteria (Rosenberg, et al., *Gene,* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein I, or polyhedrin promoters). The term "dominant negative" refers to the phenotypic effect of an expression vector or construct which expresses a nucleic acid sequence encoding a form of a rent1 polypeptide which exerts a controlling or ruling influence that is deleterious compared to the normal form of the rent1 polypeptide. In a preffered embodiment the dominant negative phenotype is conveyed by the expression of mutant rent1 proteins that interfere with the function of the normal rent1 protein. Such an effect is like the effect of dominance of one allele of a pair of alleles encoding the homologous genes on a pair of homologous chromosomes so that the phenotypic effect of the one allele exerts a deleterious controlling influence over the other allele.

Polynucleotide sequences encoding RENT1 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a target cell are known in the art. Such vectors are used to incorporate DNA sequences of the invention.

Transformation of a target cell with recombinant DNA may be carried out by conventional techniques as are well known to those skilled in the art. Where the target is prokaryotic, such as *E. coli,* competent cells which are capable of DNA uptake can be prepared from cells harvested after their exponential growth phase and subsequently treated by the $CaCl_2$ method using procedures well known in the art. Alternatively, $MgCl_2$ or RbCl can be used. Transformation can also be performed after forming a protoplast of the target cell if desired.

When the target cell is a eukaryote, such methods of transfection of DNA as calcium phosphate co-precipitates, conventional mechanical procedures such as microinjection, electroporation, insertion of a plasmid encased in liposome or liposome formulations, or virus vectors may be used. Eukaryotic cells can also be co-transformed with DNA sequences encoding the rent1 of the invention, and a second foreign DNA molecule encoding a selectable phenotype, such as the herpes simplex thymidine kinase gene. Another method of transformation is to use a eukaryotic viral vector, such as simian virus 40 (SV40) or bovine papilloma virus, to transiently infect or transform eukaryotic cells and express the protein. (see for example, *Eukaryotic Viral Vectors,* Cold Spring Harbor Laboratory, Gluzman ed., 1982).

As is demonstrated in Example 6 herein, rent1 is expressed in all of the adult human tissued tested, but considerable variation in the tissue-specific level of expression exists. One of ordinary skill in the art can expand the survey of rent1 expression by the addition of samples from more tissues and by the assessment of expression at various developmental stages in the mouse. One of ordinary skill in the art can also correlate the level of rent1 expression with the deficiency of NMRD in various tissues and at various developmental stages. This can be accomplished by a combination of Northern blot and in situ hybridization analysis using a mouse strain ($gus^{mps}$) that harbors a PTC in exon 10 (of 12) of the ubiquitously expressed gene encoding β-glucuronidase (Sands & Birkenmeier, 1993). β-glucuronidase mRNA levels are decreased by −200 fold in $gus^{mps}/gus^{mps}$ mice. In $gus^{mps}/+$mice it is possible to determine the relative contribution of the wild-type and mutant alleles to the total pool of β-glucuronidase mRNA using a quantitative RT-PCR/ASO hybridization protocol (Dietz, et al., 1993b). Five developmental stages can be targeted: day 10.5 pc [Witschi stage (WS) 25], day 16.5 pc (WS 35), birth (WS 36), day 7 (child), and day 30 (adult). Relative abundance of wild-type and mutant β-glucuronidase mRNA (as a marker of NMRD efficiency) can be determined for entire early fetuses. The tissue-specific pattern can be assessed at all later developmental stages. These results can be correlated with the expression level of rent1 using in situ hybridization (early fetus) or Northern analysis (late fetus and onward). Additionally, one of ordinary skill in the art can generate a monospecific antibody to N-terminal epitopes within rent1 using the teachings herein. The skilled artisan can create fusion proteins in bacteria (with epitopes of rent1 coupled with GST or MBP tags from Pharmacia or NEB vectors, respectively ). The resulting peptides can be used in the generation of peptide antisera and affinity purification. Specific antibodies, can then be used for Western analysis and immunohistochemistry to determine if rent1 protein expression parallels transcript expression.

It is hypothesized that mammalian NMRD has both a nuclear and cytoplasmic component. Using the teachings herein, determination of sub-cellular localization of rent1 can be established. A pHA-RNT1 expression vector encoding a fusion protein between an HA-tag and RENT1 can be transiently transfected into Cos-7 cells using the DEAE-dextran method. Immunohistochemical analysis can be carried out 48 hours post-transfection. After fixation in 3.5% paraformaldehyde and permeablization in 0.1% Nonidet P-40, cells can be incubated in a 1:100 dilution of primary antibody (anti-HA 12 CA5. Boehringer Mannheim) followed by incubation in a 1:200 dilution of secondary antibody (antimouse IgG fluorescein conjugate. BM), For the last 10 minutes of secondary incubation 1 $\mu l$ of DAPI (1 mg/ml) can be added to mark the nucleus. Staining can be visualized by fluorescence microscopy. Mock transfected (pHA without insert) and un-transfected cells can be carried through all phases of experimentation as negative controls.

Isolation and purification of microbial expressed rent1 polypeptide, or fragments, or conservative variants thereof, provided by the invention, may be carried out by conventional means including preparative chromatography and immunological separations involving monoclonal or polyclonal antibodies.

The rent1 polypeptides of the invention can also be used to produce antibodies which are immunoreactive or bind to epitopes of rent1 polypeptides. Antibody which consists essentially of pooled monoclonal antibodies with different epitopic specificities, as well as distinct monoclonal antibody preparations are provided. Monoclonal antibodies are made from antigen containing fragments of the rent1 protein by methods well known in the art (Kohler, et al., *Nature,* 256:495, 1975; *Current Protocols in Molecular Biology, Ausubel,* et al., ed., 1989).

The term "antibody" as used in this invention includes intact molecules as well as fragments thereof, such as Fab, Fab', $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual, Cold Spring Harbor Laboratory, New York (current edition)*, incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the rent1 polypeptide of the invention can be prepared using an intact polypeptide or fragments containing small peptides of interest as the immunizing antigen. The polypeptide or peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, goat, sheep or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, current edition, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The present invention identifies a nucleotide sequence that can be expressed in an altered manner as compared to expression in a normal cell, therefore it is possible to design appropriate therapeutic or diagnostic techniques directed to this sequence. Thus, where a disorder is associated with the altered expression of RENT1, nucleic acid sequences that modulates rent1 expression at the transcriptional or translational level can be used. Such a modulation can be either inhibitory or stimulatory. This approach can utilize, for example, antisense, missense or nonsense, nucleic acid and ribozymes to block translation of a specific RENT1 mRNA, either by masking that mRNA with an antisense nucleic acid or by cleaving it with a ribozyme. Such RENT1 disorders may include diseases in which a deleterious excess of nonsense alleles are stabilized in a cell, for example premature aging, or various cancers.

The RENT1 gene can be used in human gene therapy. Cells harboring genes containing nonsense alleles that encode partially functional truncated proteins can be transfected with a construct that reduces or eliminates expression or function of rent1. In the case of certain diseases such as cystic fibrosis, the resulting stabilization of the transcript, and increased expression of the truncated protein, may be sufficient to is reduce symptoms of disease.

Conversely, a construct that substantially increases the expression or function of rent1 in NMRD may further reduce the expression of partially functional truncated proteins. In the case of certain dominantly expressed disorders such as Marfan syndrome, the further reduction of these truncated protein may reduce or eliminate symptoms of disease.

The RENT1 gene and rent1 protein can be used in discovery of unknown human genes, with priori knowledge of the gene in question. In one manifestation of this invention, cells are isolated from an individual displaying a particular phenotype which is suspected of being caused by a gene or genes containing nonsense mutations. A subset of these cells is treated in a manner (such as transfecting the cells with a genetic construct) that reduces or eliminates the expression or function of rent1 in the cells. Levels of mRNA containing nonsense mutations in these cells will thus be increased to higher levels. Using standard techniques of differential display of mRNA, or genetic subtraction techniques commonly applied to cDNAs, the mRNA containing nonsense mutations can be enriched and then isolated by comparing the mRNA populations of the original cells with the mRNA populations in cells treated to eliminate or reduce rent1 activity.

Cells harboring nonsense alleles which encode partially functional truncated proteins can be transfected with constructs encoding dominant-negative forms of RENT1. If the mutant transcript were stabilized the cellular phenotype can be determined by RNA and protein quantification and biofunctional assays. In addition, subtractive hybridization methods can be used to enrich for transcripts that are unregulated after inhibition of NMRD without assuming any a priori knowledge regarding the disease gene in question since disruption of NMRD may rescue selected cellular phenotypes or manipulation of NMRD may identify novel disease genes. Furthermore, it may be possible to exploit the NMRD pathway for therapeutic purposes. Upon stabilization of nonsense transcripts by manipulation of NMRD, selected truncated protein products may retain enough of their intended function to rescue the disease phenotype. Alternatively, down regulation of NMRD in cultured patient cells that are expected to express some unknown disease gene can produce a dramatic increase in abundance of nonsense transcripts. If the phenotype is caused by a premature termination codon (PTC), then subtractive methods using RNA from unmanipulated and manipulated patient cells can greatly enrich transcripts thus permiting identification of a disease gene. By comparing the gene products of a cell line to itself, one of ordinary skill in the art can eliminate most of the "noise" from the cell (i.e., represented in non-disease mRNAs that occur when such techniques are used to compare a patient cell line to that from a control individual) thus permitting identification of specific genes and alleles. One of ordinary skill in the art can apply such a subtractive technique to identify genes and mutant alleles that are involved in complex multigenic disorders or rare phenotypes.

Antisense nucleic acids are DNA or RNA molecules that are complementary to at least a portion of a specific mRNA molecule (Weintraub, *Scientific American*, 262:40, 1990). In the cell, antisense nucleic acids hybridize to a corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target rent1 -producing cell. The use of antisense methods to inhibit the in vitro translation of genes is well known in the art (Marcus-Sakura, *Anal.Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.*, 260:3030, 1988). A major advantage of this approach is that, because they are sequence-specific, only mRNAs with particular sequences are inactivated.

Specifically, in the instant application, applicants are utilizing selected features of naturally occurring regulatory complementary RNAs (cRNAs) that have been identified in prokaryotes. All have large stable stem-loop structures that flank the molecule, with a high G-C content of the 3' hairpin and all are expressed at high levels. The structural features are believed to confer extreme stability to the molecule. All of these features are also seen in the snRNAs, essential components of the mammalian spliceosome complex that are abundant and stable in the nucleus of all mammalian cells. U1 snRNA has been chosen as the framework for the construction of chimeric antisense cRNAs because U1 is enriched in the nucleus, is widely dispersed in the nucleoplasm, and is abundantly expressed. An antisense targeting core has been substituted for the Sm protein binding site between the two hairpins.

Figure 3A:
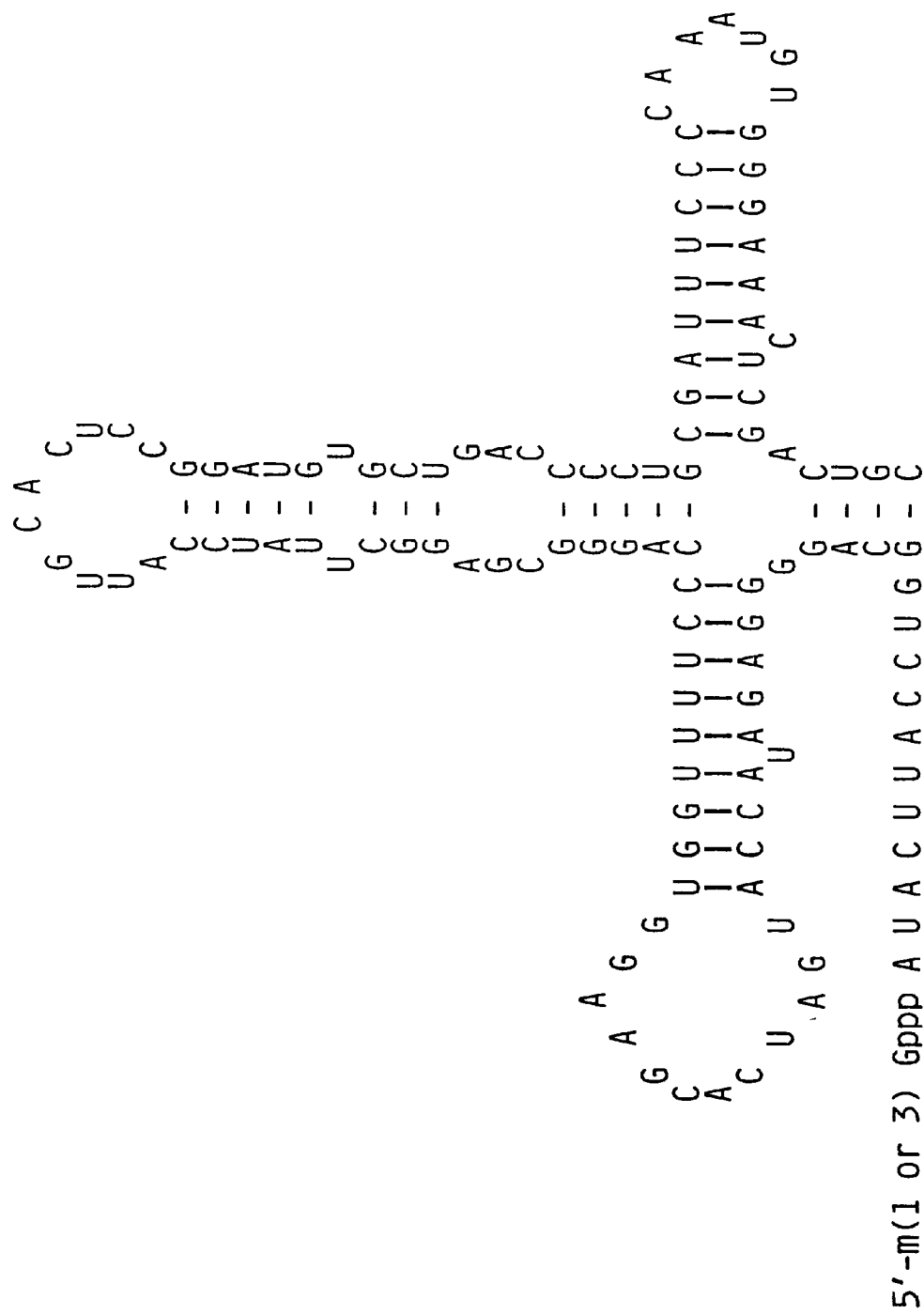
FIGS. 3A and 3B show an antisense targeting construct. The sequence (flanked by dashed lines) substituted for the Sm protein binding site (box) of native U1 snRNA is shown. This sequence is complementary to coding nucleotides 523–566 of RENT1 cDNA. The hammerhead ribozyme loop is aligned to a GUC triplet in the target, which serves as a consensus site for ribozyme cleavage (arrow). This construct will permit the process of transfecting and stably selecting cell lines which harbor known nonsense transcripts to test the efficiency of NMRD inhibition employing this strategy.
Figure 3B:
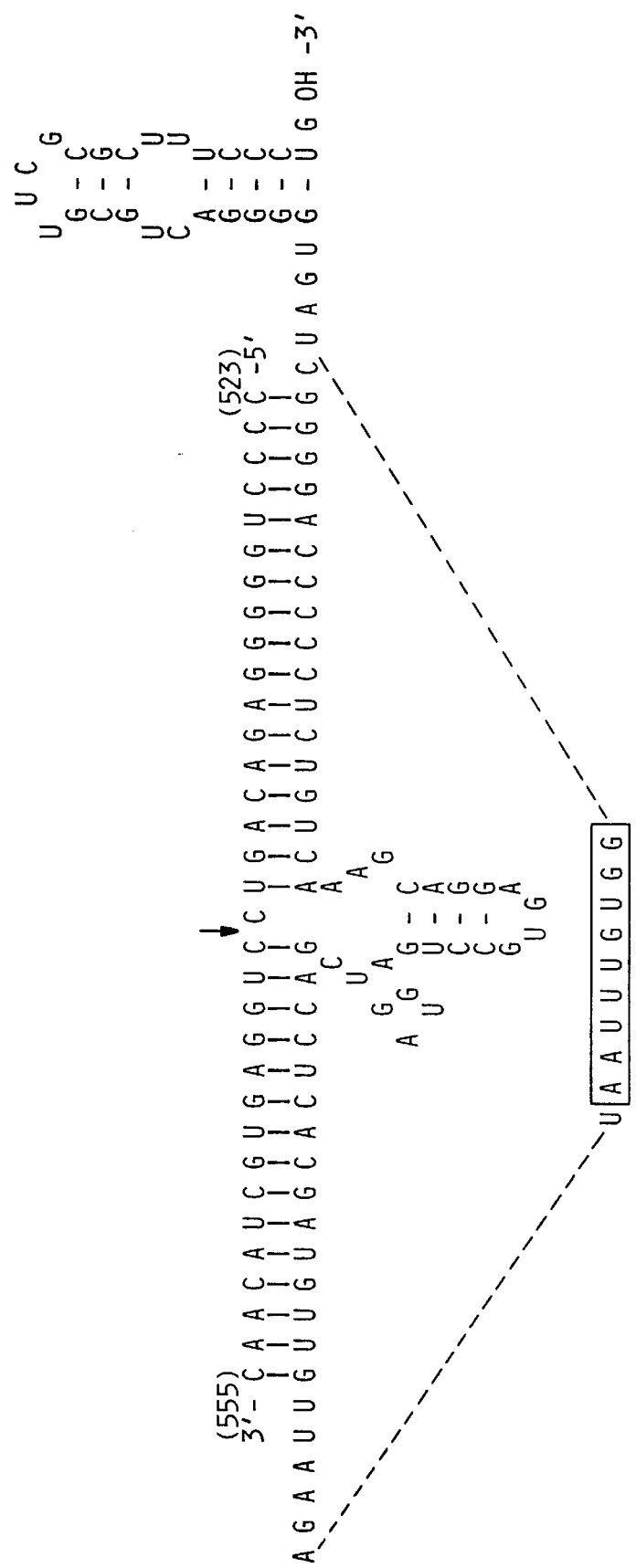

This core contains a 30–35 basepair sequence that is directly complementary to the target message, interrupted in its center by an autocatalytic hammerhead ribozyme loop. Duplex formation is expected to align the ribozyme with the GUC or GUA consensus sites for ribozyme cleavage. When the core contained sequence complementary to fibrillin-1 mRNA, expression of the chimeric cRNA, under the transcriptional control of the potent and constitutively active U1 promoter, resulted in the complete absence of fibrillin-1 protein and message in stably transfected cells. No abnormalities were seen upon a survey of other proteins and transcripts, attesting to the specificity of antisense inhibition. An expression construct to target RENT1 transcripts, employing antisense is shown in FIG. 3.

The present invention also provides gene delivery and gene expression for disorders mediated by rent1 protein. Such gene delivery and gene expression achieves its beneficial effect by altering the levels of RENT1 mRNA in a cell. This may entail delivery and expression of RENT1 antisense to target cells or the delivery and expression of heterologous RENT1 nucleic acid to target cells to modulate the function of NMRD. Delivery and expression of RENT1 nucleic acid can be achieved by a variety of means known to those in the art. A preferred means is using a recombinant expression vector such as a chimeric virus or a colloidal dispersion system. Especially preferred for therapeutic delivery of antisense sequences is the use of formulations containing liposome or liposome formulations or liposomal-like agents capable of being targeted to particular cells or receptors. Various viral vectors which can be utilized for gene therapy as taught herein include adenovirus, herpes virus, vaccinia, or, preferably, an RNA virus such as a retrovirus.

Another targeted delivery system for RENT1 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposome or liposome formulations. The preferred colloidal system of this invention is a liposome or liposomal formation.

Liposome or liposome formulations are artificial membrane vesicles or formulations containing liposomal compositions that can be complexed with other compositions. These formulations may have net cationic, anionic or neutral charge characteristics are useful characteristics with in vitro, in vivo and ex vivo delivery methods.

It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). Additionally, non-membrane bound liposomal formulations can be used for delivery and expression of nucleic acids (Felgner et al., *Proc. Natl. Acad. Sci. USA* 84:7413, 1987). In addition to mammalian cells, liposome or liposome formulations have been used for delivery of polynucleotides in plant, yeast and bacterial cells. For a liposome or liposome formulation to be an efficient gene transfer vehicle, the following characteristics should be present: (1) encapsulation of the genes of interest at high efficiency while not compromising their biological activity: (2) preferential and substantial binding to a target cell in comparison to non-target cells; (3) delivery of the aqueous contents of the vesicle or of the nucleic acid of the formulation to the target cell cytoplasm at high efficiency without degradation and in a functional state capable of permitting gene expression at such levels as to achieve a detectable biological effect; and (4) accurate and effective expression of genetic information which has been delivered (Mannino, et al., *Biotechniques*, 6:682, 1988).

A well-characterized "on/off" switch for use in a recombinant expression vector is the antibiotic (tetracycline) regulated promoter system. Means for construction of such a system are well-known in the art; for review in this regard, those of skill in the art may wish to consult Furth, et al, *Proc.Natl.Acad.Sci. USA*, 91:9302–9306, 1994 (tetracycline regulated control of gene expression in transgenic mice);

In addition, a transgenic animal model can be developed which is especially predictive of the impact on NMRD system in which RENT1 activity his been increased or decreased according to the method of the invention. Protocols useful in producing such rent1 transgenic animals are described below. The protocol generally follows conventional techniques for introduction of expressible transgenes into mammals. Those of ordinary skill in the art will be familiar with these applications and will be able to apply the techniques in the context of the present invention without undue experimentation.

For example, embryonic target cells at various developmental stages can be used to introduce transgenes. Different methods are used depending on the stage of development of the embryonic target cell. The zygote is the best target for microinjection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster, et al., *Proc. Natl. Acad. Sci. USA* 82:4438–4442, 1985). As a consequence, all cells of the transgenic non-human animal will carry the incorporated transgene. In general, this will also be reflected in the efficient transmission of the transgene to offspring of the founder since 50% of the germ cells will harbor the transgene. Microinjection of zygotes is a preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenisch, *Proc. Natl. Acad. Sci USA* 73:1260–1264, 1976). Efficient infection of the blastomeres is obtained by enzymatic treatment to remove the zona pellucida (Hogan, et al., *Manipulating the Mouse Embryo*, Cold Spring Harbor Laboratory Press, Cold Spring Harbor, N.Y., 1986). The viral vector system used to introduce the transgene is typically a replication-defective retrovirus carrying the transgene (Jahner, et al., *Proc. Natl. Acad. Sci. USA*, 82:6927–6931, 1985; Van der Putten, et al., *Proc. Natl. Acad. Sci USA* 82:6148–6152). Transfection is easily and efficiently obtained by culturing the blastomeres on a monolayer of virus-producing cells (Van der Putten, supra; Steward, et al., *EMBO J.* 6383–388,1987).

Alternatively, infection can be performed at a later stage. Virus or virus-producing cells can be injected into the blastocoele (Jahner, et al., *Nature,* 298:623–628, 1982). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, et al., supra, 1982).

A third type of target cell for introduction of heterologous RENT1 nucleic acid sequences is the embryonal stem cell (ES). ES cells are obtained from pre-implantation embryos cultured in vitro and fused with embryos (Evans, et al., *Nature,* 292:154–156, 1981; Bradley, et al., *Nature,* 309:255–258, 1984; Gossler, et al., *Proc. Natl. Acad. Sci USA,* 83:9065–9069, 1986; and Robertson, et al., *Nature,* 322:445–448, 1986). Transgenes can be efficiently introduced into the ES cells by DNA transfection or by retrovirus-mediated transduction. These transformed ES cells can thereafter be combined with blastocysts from a non-human animal. The ES cells will thereafter colonize the embryo and contribute to the germ line of the resulting chimeric animal (see for review, Jaenisch, *Science,* 240:1468–1474, 1988).

Construction of RENT1 transgenes can be performed by those of ordinary skill in the art using the teachings concerning the RENT1 nucleotide sequences herein. One of ordinary skill in the art can "knock out" the NMRD pathway in mice by targeted disruption of the murine Rnt1 gene. This can be accomplished by homologous recombination in murine embryonic stem (ES) cells using standard techniques. The clinical and cellular consequences of targeted disruption of Rnt1 can be investigated in multiple genetic backgrounds including inbred strains, strains with many undefined nonsense alleles, and strains of known mutant genotype to determine if: (a) targeted disruption of Rnt1 can effect a loss of NMRD function; (b) loss of NMRD function can have an phenotype consequences (i.e., the creation of knockout phenotypes), (c) loss of NMRD unmasks the effects of protein that can be expressed from "physiologic" somatically acquired or inherited nonsense alleles upon transcript stabilization.

Transgenic murine cells can be generated by using a vector for RENT1 gene targeting by homologous recombination. The vector contains a large genomic fragment of the murine RENT1 gene. Three exons can be deleted and substituted for by a Neomycin resistance expression cassette. A thymidine kinase gene can be inserted at the end of the long arm of homology to assist in the selection of bona fide-homologous recombinants. Transfection and stable selection of murine SW 129 cells will allow identification of a clonal colony of cells harboring one inactivated RENT1 allele. These cells can be injected into mouse blastocysts to create chimeras. Chimeras can be bred to yield animals heterozygous for the targeted allele. Finally, heterozygotes can be bred to create homozygotes. Mice with characterized phenotypes can be bred to mice deficient for NMRD. Differential display, SAGE, or other methods can allow identification of transcripts upregulated in the absence of NMRD. In this way, a mouse disease gene can be identified. It will then be possible to determine whether a human homologue of the mouse disease gene is responsible for similar human phenotypes. If necessary, the identical approach of homologous recombination-based targeting of endogenous genes can then be used in cultured human cells. This would require a second phase of transfection and selection, using a different selectable marker, to target both alleles. Only minor modifications in the methods used for murine cells, all previously employed for other purposes, will be necessary to permit one of ordinary skill in the art to completely inhibit RENT1 expression in cultured human cells. One example of such a method of transgenic construction is described below. However, this example is not meant to be limiting as other transgenic constructions can be used which are commonly known to those in the art.

Insertion of the 1.2 kb Pol II-neomycin resistance cassette into an early exon of the Rnt1 gene will disrupt the translational reading frame for RENT1 with the creation of an in-frame premature termination codon (PTC). Insertion of the PTC in an early exon will prevent translation of the body and C-terminus of RENT1 will result in a complete loss of function. An alternate strategy is to target the very first exon eliminating the start-site for translation, however this might impair transcription, precluding the ability to assess the stability of targeted Rnt1 transcripts as a potentially useful marker of the integrity of NMRD in lines of knockout mice. N-terminal epitopes can also be used to determine whether a truncated protein is expressed from stabilized transcripts from the knockout allele.

Construction of a Targeting Vector

Figure 10:
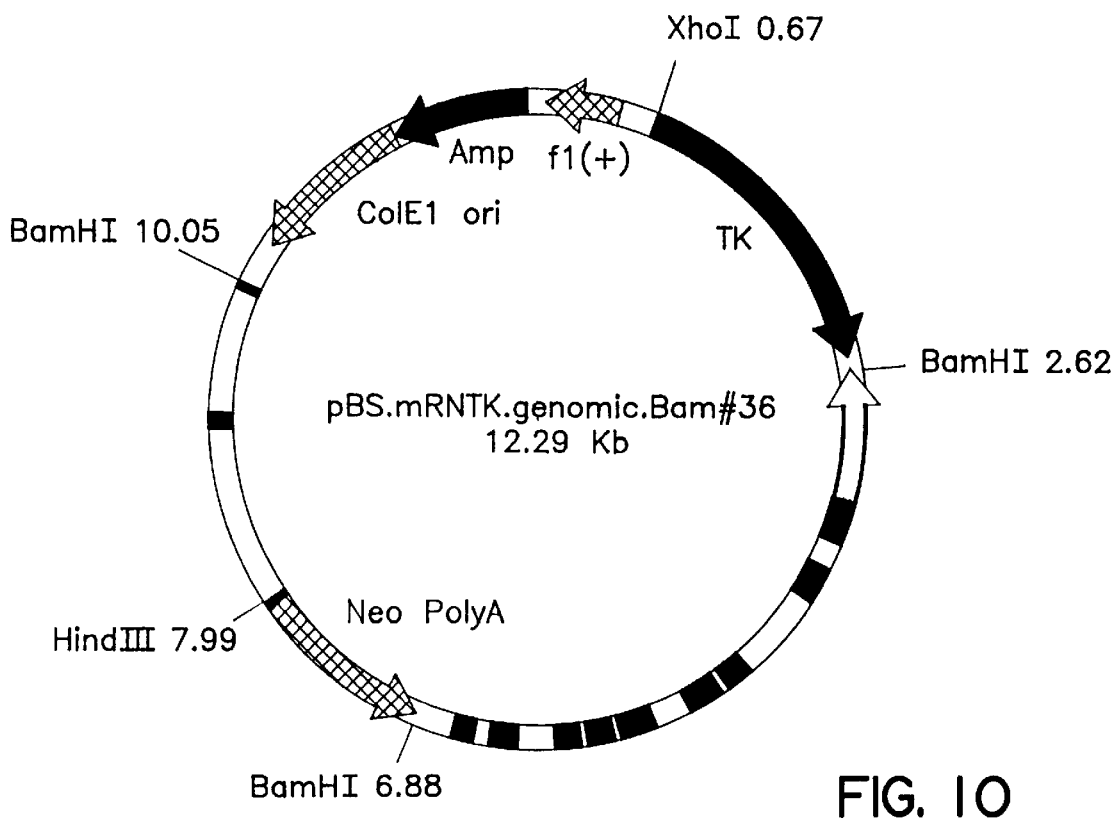
FIG. 10 shows the targeting vector for murine RENT1 designated pBS.mRENT1.TK.genomic.Bam#36.

A large fragment of murine RNT1 cDNA is cloned, (~20 kb) murine (129/Sv) genomic clone spanning from the second putative nucleotide binding motif to the first motif that confers NTPase activity, and characterized. A detailed restriction map of the clone and localizing intron-exon boundaries through a combination of the subcloning of relatively large (6–12 kb) restriction fragments into plasmid vector (pBlueprint II-SK) is determined, restriction analysis accompanied by Southern transfer and hybridization of radiolabeled oligonucleotide complementary to cDNA sequences, and direct sequencing of genomic subclones using cDNA primers can be done. Subsequently, a targeting vector is constructed using a (6–12 kb) genomic fragment which contains the exon of interest is subcloned into a suitable plasmid. Preferably, the exon is somewhat asymmetrically placed in the insert, with a minimum of ~2 kb of sequence at either end (Deng & Capecchi, 1992). Genomic sequences that immediately flank the insert at the 5' and 3' ends are retained for use as probes in Southern analysis to confirm homologous recombination at a later time. The 1.2 kb Pol II-neomycin resistance expression cassette (Wang, et al., 1995) is inserted into the exon of interest using a suitable restriction site. The PGKtk expression cassette is added distal to the long arm of homology to enrich for homologous recombinants by FIAU selection (Li, et al., 1992: Andrikopoulos, et al., 1995). The resultant construct is linearized and band-purified by $CsCl_2$ ultracentrifugation (Wang, et al., 1995). A targeting vector using RENT1 sequence is illustrated in FIG. 10.

Additionally, recent advances in the efficiency of targeted gene delivery in cultured somatic cells can be used by one of ordinary skill in the art. Briefly, promoterless cDNAs that encode antibiotic resistance factors are used in targeting vectors such that expression can be driven by the promoter of the targeted allele upon homologous recombination. Enrichment ratios (homologous recombinants vs. random insertions) of up to 5,000 to 10,000-fold can be achieved compared to conventional methods (Hanson & Sedivy, 1995), thus efficiently inactivating both alleles by sequential gene targeting using two targeting vectors that contain different selectable genes.

Generation of Targeted Mice

Pluripotent J1 ES cells derived from the inner cell mass of 129/Sv blastocysts are cultured under standard conditions (Li, et al., 1992). Approximately $1 \times 10^7$ cells are transfected with 10–20 μg of linearized construct by electroporation at 230 m$^v$, 500 μF using a Bio-Rad Gene Pulser and are replated on a feeder layer of γ-irradiated G418-resistant primary mouse embryonic fibroblasts in Delbecco's modified Eagle's media supplemented with 5% FBS, 0.1 mM non-essential aa, 0.1 mM βME and 1000 U/ml leukemia inhibitory factor (Li, et al., 1992). Selection with G418 and FIAU commences 24 hours after plating and is maintained for seven to ten days. An aliquot of each resistant colony (~90%) is frozen for later use and the remainder are replated and grown to confluence for DNA extraction. Identification of recombinant clones is accomplished by Southern analysis and facilitated by a single EcoR1 site in the Neo cassette and the probes that flank the homologous sequences are used for gene targeting as above. The 5'-flanking probe is used to detect a restriction fragment unique to the targeted allele. DNA from all positive clones are subsequently screened with the 3' probe to confirm bona fide homologous recombination (Wang, et al., 1995). Northern analysis are performed on RNA extracted from +/+ and +/– colonies. By observing the size and abundance of hybridizing species of Rnt1 RNA one of ordinary skill in the art can learn early valuable information regarding the influence of the haploinsufficiency state for Rnt1 upon the efficiency of NMRD. The cDNA probe used in Northern analysis does not span the site of Neo insertion, and should hybridize equally well to the intact and targeted alleles. In addition, the transcription rate and transcript stability can be determined using nuclear run-on analysis and Northern or RNase-protection analysis of RNA extracted at various intervals after the addition of actinomycin D (5 μg/ml) to inhibit new transcription (Urlaub, et al., 1989; Cheng & Maquat, 1993). These parameters can be determined on an allele-specific basis by observing differences in transcript size or by using fusion probes which contain both Rnt1 and Neo sequences.

Approximately 15 cells from each targeted ES cell clone are microinjected into each C57B1/6J blastocysts (~15) collected at 3.5 days post coitus. Chimeric offspring are identified by agouti (ES-derived) coat color. Male chimeras are bred with C57B1/6J females. Homozygotes for the targeted allele are be generated by the breeding of heterozygotes. The genotype of all mice are determined by Southern analysis or a PCR-based assay.

Characterization of Resultant Mice

The genetic complement of all initial mice are composed solely of the genomes of two well characterized inbred stains. Therefore, the murine genomes carry no deleterious recessive nonsense alleles other than the targeted Rnt1 allele. Litter size, sex ratio, and genotyping of all newborn mice are used to monitor embryonic lethality. Mice of all 3 genotypes (+/+, +/– and –/–) are examined carefully over time for any phenotypic differences including birth weight, growth, activity, and congenital or acquired anomalies. Non-viable mice undergo autopsy.

Molecular analysis of mice of all three genotypes are performed. First, the character and steady state level of Rnt1 transcripts are determined by Northern analysis and RNase protection. Second, the level and distribution of reactive protein are determined by Western analysis and immunohistochemistry. Experiments identical to can be performed to determine the allele-specific Rnt1 transcription rates and transcript stabilities. A simultaneous analysis is performed on total, nuclear, and cytoplasmic RNAs (Daar & Maquat, 1988). Finally, nonsense-transcript stability is upregulated in RENT1-deficient mice, fetal fibroblast cultures are established and transfected with a construct expressing wild-type RENT1 to determine whether reconstitution with RENT1 can rescue an abnormal phenotype.

Outcrossing of Homozygous null (–/–) Mice and Further Experimentation

To determine the phenotypic consequence of loss of NMRD function in different genetic backgrounds, the following breeding experiments can be performed:

(1) Murine mucopolysaccharidosis type VII (analogous to human Sly syndrome) is an autosomal recessive disorder caused by spontaneous mutation (gus$^{mps}$) in the β-glucuronidase gene. Heterozygous mice are commercially available through the Jackson Laboratory. The gene product is required for the degradation of glycosaminoglyares in lysosomes and homozygous mutant mice display developmental, skeletal, and heart abnormalities that cause a shortened life-span. The gus$^{mps}$ mutation has recently been characterized as a 1 bp deletion in exon 10 (of 12) that causes a PTC in the same exon (Sands & Birkenmeier, 199,). (β-glucuronidase mRNA levels are decreased by ~200-fold in gusmps/gusmps mice and no immunoreactive protein is detectable. In that β-glucuronidase is expressed in all tissues and throughout development, one of ordinary skill in the art can determine the developmental- and tissue-specific relative stability of transcripts derived from the gusmps allele in (gusmps/+, Rnt1+/+) mice. The results can be compared to the tissue-specific expression pattern of rent1 to determine whether the level of RENT1 is a limiting factor in the determination of tissue-specific NMRD efficiency. In addition, Gus$^{mps}$/+ mice are crossed with either Rnt1+/− or Rent1 −/− mice (depending upon the viability and fertility of homozygotes). Resulting (gus$^{mps}$/+, Rnt1+/−) mice are crossed to produce (gus$^{mps}$/+, Rnt1−/−), (gus$^{mps}$/gus$^{mps}$, Rnt1−/−) and (gus$^{mps}$/gus$^{mps}$, Rnt1+/+) mice as determined by tail DNA genotyping. This permits one of ordinary skill in the art to examine the influence of Rnt1-genotype upon the stability of transcripts derived from an unlinked nonsense allele. Molecular analyses are identical to those described above except that β-glucuronidase gene-specific sequences and probes are utilized (Birkenmeier, et al., 1989). Mice of all genotypes are analyzed, and the genotype-specific results can be compared. If β-glucuronidase transcripts are stabilized in the Rnt1−/− background, the phenotypic consequence to gus$^{mps}$/gus$^{mps}$ mice can be determined. The encoded protein can contain a contiguous stretch of ~190 wild-type amino acids (normally 648) and it is possible that the truncated protein can retain activity. This can be tested by Western analysis and histochemical stain for β-glucuronidase activity (Sands & Birkenmeler, 1993).

(2) Strain III mice lack 4-hydroxyphenylpyruvic acid dioxygenase (HPD) activity and contain a nonsense mutation (R111X) in exon 7 (of 14) of the Hpd gene (Endo, et al., 1991, 1995). Homozygous mice develop normally but have elevated blood levels of tyrosine and show massive urinary secretion of metabolites, equatable with human type III tyrosinemia. R111X/R111X-homozygous mice have abundant amounts of Hpd transcript, albeit abnormally small in size. The vast majority of the message has been shown to lack exon 7 due to exon skipping during pre-mRNA processing (Endo, et al., 1995). All of the cis-acting elements known to regulate splicing are unaltered, suggesting that the abnormal splicing phenotype is caused by the nonsense mutation. By breeding strain III mice with RENT1 knockout mice, one of ordinary skill in the art can determine whether rents and the NMRD pathway participate in abnormal splice-site selection in response to premature termination codons. This can be tested easily by Northern blot or RT-PCR analysis of Hpd mRNA extracted from the liver or kidneys of mice (Endo et al., 1995) harboring various combinations of heterozygous and homozygous genotypes of the Hpd and Rnt1 1 genes. The type III strain is available from the Central Institute for Experimental Animals in Kawasaki, Japan.

If homozygosity for the targeted allele is incompatible with embryonic development, but heterozygosity is not associated with a phenotype, it is possible to generate dominant-negative or relative loss-of-function alleles. The size and character of such mutations would be influenced by expression studies using mammalian cells. The process of generating subtle (e.g. missense) mutations in the genome of ES-cells is well described and quite effective (Stacey et al., 1994). Briefly, a targeting vector is first used to replace a defined region of the target gene in HPRT-deficient ES cells with an HPRT minigene. After selection for the HPRT+ phenotype, a second round of targeting is used to replace the HPRT minigene with a desired DNA fragment that harbors a site-specified mutation. Enrichment for homologous recombinants is achieved by selection for reversion to the HPRT phenotype. Mice heterozygous for a dominant-negative mutation or homozygous for a relative loss-of-function mutation may have sufficient impairment of NMRD to show a phenotype yet be viable. All potential mutations can be assessed in cultured cells for their relative impact on NMRD efficiency, and a select few can be used in transgenic experimentation.

Additionally, if homozygosity for the targeted RENT1 allele is incompatible with embryonic development, one of ordinary skill in the art can apply inducible gene targeting under the control of the CrelloxP recombination system of bacteriophage P1 (Sauer & Henderson, 1988). The Cre recombinase directs site-specific recombination between two short recognition sequences (loxP) without additional co-factors. Cre recognizes the loxP sites and nicks them on opposite strands, leaving behind a single loxP site after recombination. This process deletes or inverts the intervening ("floxed") DNA sequence when the loxP sites are placed in a head-to-tail or head-to-head orientation, respectively. In vivo gene inactivation can be restricted to a specific development stage or tissue by crossing a mouse strain harboring a floxed allele to a transgenic strain of activation (Gu et al., 1994; Kuhn et al., 1995). Alternatively, an inducible promoter can be used to drive Cre expression. First, an exon or region of Rnt1 would be flanked by two loxP sites using gene targeting methods described above. A resistance-conferring gene is included between the loxP sites but outside of the coding region for Rnt1 to allow for positive selection of recombinant clones. Resulting mice are bred to homozygosity for this targeted, albeit functionally intact, allele. Resulting homozygotes are bred to a transgenic strain that expresses Cre under the control of a promoter with desirable characteristics. By bypassing certain critical developmental stages or tissues, one of ordinary skill in the art can create a viable and useful model of NMRD deficiency despite the inherent essential nature of the gene product. The choice of the promoter for Cre expression can be an interferon-inducible promoter of the mouse Mx1 gene (Kuhn et al., 1995).

The present invention can also be used to for therapeutic purposes by modulating NMRD. Cells harboring stabilized nonsense alleles which encode partially functional truncated proteins can be transfected with constructs encoding dominant negative forms of rent1. The cellular phenotype can be determined by RNA and protein quantification and biofunctional assays. In addition, subtractive methods can be used to enrich for transcripts that are upregulated after inhibition of NMRD without assuming any a priori knowledge regarding a possible disease gene in question. The use of RENT1 can allow disruption of NMRD and rescue of selected cellular phenotypes or manipulation of NMRD for the identification of new disease genes. One such non-limiting example is described below, however, the skilled artisan using this example can create other such bioassays to explore disease genes using RENT1.

Two predominant pathogenetic mechanisms are generally inferred when an allele of a given disease gene is found to harbor a premature termination codon (PTC). Both relate to a presumed loss-of-function. Either the predicted truncated protein lacks C-terminal domains that are essential for intended function, or the NMRD pathway effectively eliminates expression from the mutant alleles by degrading much or all of the nonsense transcripts. These mechanisms are not mutually exclusive, and may act in combination. However, for certain proteins, selected C-terminally truncated forms retain sufficient activity to prevent or abrogate the disease phenotype. In such an instance, NMRD is the critical factor. This is probably the case for certain nonsense alleles of the cystic fibrosis transmembrane conduction regulator (CFTR). As little as the amino-terminal half of CFTR can form a functional regulated chloride channel (Sheppard et al., 1994). Selected truncated proteins (e.g. corresponding, to mutation D836X) had conductance properties indistinguishable from those of wild-type CFTR (Sheppard et al., 1994). However, in vivo, transcript levels are extremely low (e.g,. for mutations W1282X and W1316X), generally less than 5% of that observed from the wild-type allele (Hamosh et al., 1991, 1992). Stabilization of selected CFTR nonsense transcripts, through manipulation of rent1 and hence NMRD, may effect emergence or significant chloride channel function in CTFR affected cells.

To test such a hypothesis one of ordinary skill in the art can stably transfectant the respiratory epithelial cell line IB3-1 with vectors encoding, both wild-type and putative dominant-negative forms of rent1. IB3-1 harbors CFTR mutations ΔF508 and W1292X and demonstrates normal chloride conductance parameters upon reconstitution with wild-type CFTR (Fulmer et al., 1995; incorporated herein in its entirety including all figures and drawings). Using, dominant-negative forms of rent1 one of ordinary skill in the art can determine if such a treatment stabilizes W1282 transcripts. If so, one of ordinary skill in the art can use a well described biofunctional assay to assess whether any chance in cAMP-mediated chloride conductance is seen (Fulmer et al., 1995). Briefly, IB3-1 cells (untransfected, mock-transfected, expressing wild-type or dominant-negative rent1 ) can be loaded with $^{36}$Cl- (Fulmer et al., 1995). Cells can be washed extensively in ice-cold Ringer's solution prior to the addition of warm solution. CPT-cAMP (to 200 mM; Boehringer Mannheim) can be added, and the incubating solution exchanged at various time points thereafter. After the final time point, cells can be lysed in 0.1 N NaOH. Radioemissions from each time point of the retained samples counted and final values for each time point expressed as % total cellular counts at time 0 which were lost per minute. The efflux rates can be compared between experiments using the one-way analysis of variance (ANOVA) test and the Duncan multiple variable test (Fulmer et al., 1995). The results can be correlated with protein expression, assessed by Western analysis and immunohistochemistry. Product from the W128X allele can be distinguished from that from ΔF508 allele by virtue of its size and cell-surface localization.

If protein expression is upregulated, but chloride conductance does not change, then it is possible that the W1282X form of CFTR lacks critical domains needed for trafficking, processing, or chloride conductance. Other mutant cell lines can then be tested. If both protein expression and chloride conductance are upregulated by the expression of dominant-negative forms of rent1, then it can be evident that transcripts stabilized by manipulation of NMRD can be translated and that the resulting protein products can show residual function. Such a result could be important for the development of novel therapeutic strategies. For example, it may be possible to manipulate the expression of rent1 in vivo using genetic therapeutic or pharmacologic interventions. This would have a profound impact on the care of patients carrying W1282X (accounting for 60% of CF chromosomes in the Ashkenazi Jewish population; Shoshani et al., 1992), and perhaps for individuals harboring other nonsense mutations in CFTR or in other genes.

The present invention may ameliorate mutations in RENT1 genes. Because mutant rent1 polypeptides can correlate with increased accumulation of nonsense mRNAs, RENT1 nucleic acid can be useful in gene therapy. By using RENT1 constructs to enhance NMRD in cells afflicted with nonsense mutation accumulation, it is possible to treat disease states associated with stabilized transcripts of nonsense mutations. In preferred therapies, the RENT1 regulating gene product is preferentially expressed in those cells where enhanced NMRD is required. Alternatively, therapy is provided by administration of peptidomimetic or other compositions which mimic the biological activity of wild-type rent1 polypeptides or which modify a NMRD defect, caused by a defect in a mutant rent1 polypeptide thereby restoring wild-type biological activity to a mutant polypeptide.

The experimental manipulation of rent1 can be used in the novel therapeutic strategies and the identification of unknown disease genes. Many strategies to identify new disease genes or to monitor the cellular response to environmental or physiologic stress rely upon the detection of differences in gene-specific transcript expression between control and experimental samples. These include differential cDNA screening, subtractive hybridization strategies, and multiple RF-PCR-based methods (reviewed in Maser & Calvert, 1995). RNA isolated from an "affected" cell line or tissue is compared to that from an "unaffected" control. Loss of NMRD function in both yeast and C. elegans has been shown to have negligible, if any, effect on the abundance of transcripts that do not contain PTCs therefore suggesting that cell viability remains unaffected (Leeds et al., 1991; Pulak & Anderson, 1993).

PTCs are caused by nonsense mutations and frameshifts (aberrant splicing, deletions, insertions, complex rearrangements), therefore, nonsense alleles account for a large proportion of all human disease (Cooper & Krawczak, 1993). This fact, in conjunction with experimental manipulation of NMRD, can permit identification of selected disease genes. One of ordinary skill in the art can be determine such disease genes using a patient cell line which harbors known nonsense alleles. If NMRD is downregulated in one aliquot of cells from such a cell line then the only difference between a cell line transfected with RENT1 constructs and a culture of the same line which has been unmanipulated should be a greatly increased abundance of nonsense transcripts in the RENT1 treated cells. This enrichment for nonsense transcripts of putative disease (genes can then be detected by a number of methods including those described herein. One example of such a detection of disease alleles is described below. The example is meant to be illustrative and not restrictive in any manner either explicitly or implicitly. Other methods will be apparent to those of ordinary skill in the art.

A fibroblast cell line from a patient with gyrate atrophy who is homozygous for a 1 bp deletion at codon 318 in the OAT gene was obtained. This allele is associated with undetectable levels of OAT mRNA (Body et al., 1992). Cells from this line can be stably transfected with constructs expressing either wild-type or a dominant-negative form of rent1. RNA can be extracted from both cell lines and compared by representational difference analysis (RDA) (Hubank & Schatz, 1994). RDA is a preferred method of comparative analysis using the instant technology because it efficiently detects quantitative as well as absolute differences, and eliminates cDNA fragments common to both cell populations, leaving behind only the differences (Hubank & Schatz, 1994). The identity of resultant cDNA fragments can be determined by a combination of subcloning, sequencing, and database analysis. The RDA method can also be applied to heterozygous nonsense alleles using identical methods and appropriate fibroblast cell lines from patients with other diseases such as Marfan syndrome (Dietz et al., 1993b).

Stabilization of inefficiently spliced pre-mRNAs from normal alleles will not be obstructive to this process because of their low abundance. Additionally, the RDA analysis method can enrich for transcripts derived from recessive nonsense alleles that are unrelated to the phenotype of interest. The number can below and many can not be expressed in the tissue source for RNA isolation that was selected because of its relevance to the phenotype of interest (both OAT and fibrillin-1 are expressed abundantly in cultured fibroblasts). Such a method is preferred to define syndromes associated with mutations created by PTCs (e.g., the Stickler syndrome gene where all Stickler mutations create PTCs). This approach is preferred because of its unique applicability to detect rare sporadic or complex multigenic disorders. In complex multigenic disorders one of ordinary skill in the art can obtain a catalog of nonsense alleles in many patients with concordant phenotypes. Those nonsense alleles that are found to be common to multiple affected patients can be investigated further.

A preferred method of gene therapy is direct gene transfer, i.e., local application of a formulation containing the rent1 polypeptide-encoding nucleic acid into an afflicted site or other region. A variety of well known vectors are be used to deliver the RENT1 gene to targeted cells in a location like those cells affected in Stickler syndrome or Marfran syndrome, including but not limited to adenoviral vectors, adeno-associated vectors or formulations targeting endothelial cells. In addition, naked DNA, liposome formulations delivery methods, or other novel formulations developed to deliver the RENT1 gene to target cells are also preferred.

For any of the above approaches, the therapeutic rent1 polynucleotide construct can be applied to a location where enhanced NMRD is desirable (e.g., by injection), but the RENT1 formulation may also be applied to tissue in the vicinity of the needed NMRD modulation, to a blood vessel supplying the cells where modulated of NMRD is desirable or even applied systemically.

In a RENT1 gene delivery formulation of the instant invention, polynucleotide expression is directed from any suitable promoter (e.g., the human cytomegalovirus, simian virus 40, actin or adenovirus constitutive promoters; or the cytokine or metalloprotease promoters for activated synoviocyte specific expression). Furthermore, RENT1 polynucleotide production can be regulated by any desired mammalian regulatory element. For example, if desired, enhancers known to direct preferential gene expression in cells known in the art to be associated with NMRD may be used to direct RENT1 gene expression. Such enhancers include, without limitation, those enhancers which are characterized as tissue or cell specific in their expression.

Alternatively, if a RENT1-gene regulating (genornic clone is utilized as a therapeutic construct, expression is regulated by its cognate regulatory sequences or, if desired, by regulatory sequences derived from a heterologous source, e.g., any of the promoters or regulatory elements described above.

Gene therapy may also be accomplished by direct administration of the RENT1-regulating gene mRNA to a cell either in vitro, ex vivo, or in vivo. RENT1 mRNA may be produced and isolated by any standard technique, but is most readily produced by in vitro transcription using a cDNA under the control of a high efficiency promoter (e.g., the T7 promoter). Administration of RENT1 mRNA to accumulated cells is carried out by any of the methods for direct nucleic acid administration described herein.

In one embodiment, the production of the rent1 protein by a gene therapy approach described herein results in a cellular level of the rent1 polypeptide that is at least functionally equivalent to the normal, cellular level in a normal individual. Treatment by any gene therapy approach described herein may also be combined with more traditional therapies.

Another therapeutic approach included within the invention involves direct administration of recombinant rent1 protein by any conventional recombinant protein administration techniques at the site where pathogenic cells accumulate (for example, by injection), or administered systemically. The rent1 protein may also be targeted to specific cells or receptors by any of the methods described herein to target RENT1 nucleic acid formulations. The actual dosage of rent1 protein depends on a number of factors, including the size and health of an organism, but, generally, between 0.1 mg and 100 mg inclusive are administered per day to an adult in any pharmaceutically-acceptable carrier.

In one embodiment, the invention provides a method of treating a patient having or at risk of having early stage as a result of genetic deficiency, disease or clinical treatment wherein the condition has an etiology associated with a defective NMRD-regulating gene or polypeptide, deficient RENT1 or level thereof, the method comprising administering to the patient a therapeutically effective amount of a formulation or composition which modulates the expression of the RENT1 gene or polypeptide such that the state of the patient is ameliorated.

Therapeutic applications also include utilizing a selective survival technique taking advantage of those cells specifically expressing the wild-type protein, eg., rent1. Such treatment kills or inactivates the cell that contains a defective RENT1 gene, while leaving cells containing the wild type or normal RENT1 gene/polypeptide unharmed. Several approaches for selective killing include but are not limited to: 1) infection with a viral vector to induce expression of the endogenous, normal RENT1 gene,; 2) contact a cell having a mutant rent1 protein with an agent that specifically binds to the mutant and not the wild-type protein; and 3) contact a cell having a mutant rent1 protein with a first agent that protects the wild-type RENT1 and then a second agent that is toxic to a mutant rent1.

EXAMPLES

The following examples are intended to illustrate but not admitted to limit the invention in any manner, shape, or form (either explicitly or implicitly). While they are typical of those that might be used, other procedures, methodologies, or techniques known to those skilled in the art may be used alternatively.

Example 1

Cloning Human RNT1 cDNA Using Degenerate Primers

Multiple primers were fashioned using degenerate sequences that encode short peptide fragments common to Upf1, Sen1, and Mov10 (Table 1).

TABLE 1

Peptides Encoded by Degenerate Sequences of Primers Used to Clone Human RNT1

| Peptide | Amino Acids | SEQ ID NO |
|---------|-------------|-----------|
| PGTGKT  | 432–437 of Upf1 | 23 |
| CAPSN   | 458–462 of Upf1 | 24 |

The primers were then used in multiple combinations for RT-PCR of RNA extracted from cultured human fibroblasts. RNA extraction and RT-PCR were performed according to conventional methods. RT-PCR using the primers PGTGKT (SEQ ID NO:23) and CAPSN (SEQ ID NO:24) together produced a product comparable in size to Upf1. The sense and antisense primers encode the peptide sequences PGT-GKT (aa 432–437 in Upf1) and CAPSN (aa 458–462 in Upf1), respectively. Conceptual translation of the 30 codons contained within the RT-PCR product revealed that it shared 93% sequence conservation and 73% sequence identity with Upf1 of yeast, suggesting that the cloned gene encodes a mammalian regulator of NMRD.

Example 2

Cloning Human RNT1 cDNA Using Mammalian Expressed Sequence Tags Est's)

The yeast Upf1 sequence was submitted to the X-REF database genome cross-referencing effort (Bassett, et al., 1995). This service compares the query sequence from a model organism protein (yeast, C. elegans, etc.) With the conceptual translation of mammalian expressed sequence tags (EST) using the BLAST local alignment search algorithm (Altschul, et al., 1994). Submission resulted in the identification of a human expressed sequence tag (EST, GenBank F06433), derived from a normal human infant brain cDNA library, that encodes a protein with significant similarity to Upf1p (p=2.8e-44). The cDNA clone obtained from the Human Genome Center of Lawrence Livermore National Laboratory, contained an insert of approximately 1.5 kb. DNA sequencing of this insert revealed a contiguous open reading frame of approximately 1.4 kb, with a poly(A) tail and a 3' UTR of 100 bp. Full-length RENT1 cDNA clones were isolated from an adult human heart cDNA library, contained within the cloning vector pCMV SPORT (BRL), using the GENE TRAPPER cDNA positive selection system (Life Technologies). Screening was carried out according to the manufacturer's instructions with oligonucleotide 23-5-2a (5'-CTTTGACAGGATGCAGAGCGC-3') (SEQ ID NO:11) Two independent clones, each having an insert of approximately 3.7 kb, were identified. DNA sequencing of the clones reveals an open reading from of 3,354 bp, flanked by a 5' UTR of 231 bp, a 3' UTR of 103 bp, and a poly(A) tail. The use of BLAST to compare the sequence of this clone with the sequence of yeast Upf1 suggested that the isolated clone, RNT1, encoded a polypeptide similar in sequence to Upf1 (p=0.00). Sequencing was performed using a Perkin Elmer Applied Biosystems Division (ABd) 373a automated DNA sequencer following manufacturer's protocols. Direct sequencing predicts an ORF of 3354 bp with 231 bp of 5'UTR and 103 bp of 3'UTR, excluding the poly(A) tail. The putative initiating methionine is encoded by an ATG codon that falls within context (GGCACCATGA) (SEQ ID NO:12) that closely matches the Kozak consensus sequence GCC(A/G)CCATGG(SEQ ID NO:13) including the highly conserved purine at position -3 (Kozak, 1991). Moreover, this is the first ATG3' of an in-frame amber codon (23 codons upstream). The mammalian polypeptide was designated rent1.

Example 3

Cloning Murine RNT1 Genomic DNA and cDNA

Figure 11:
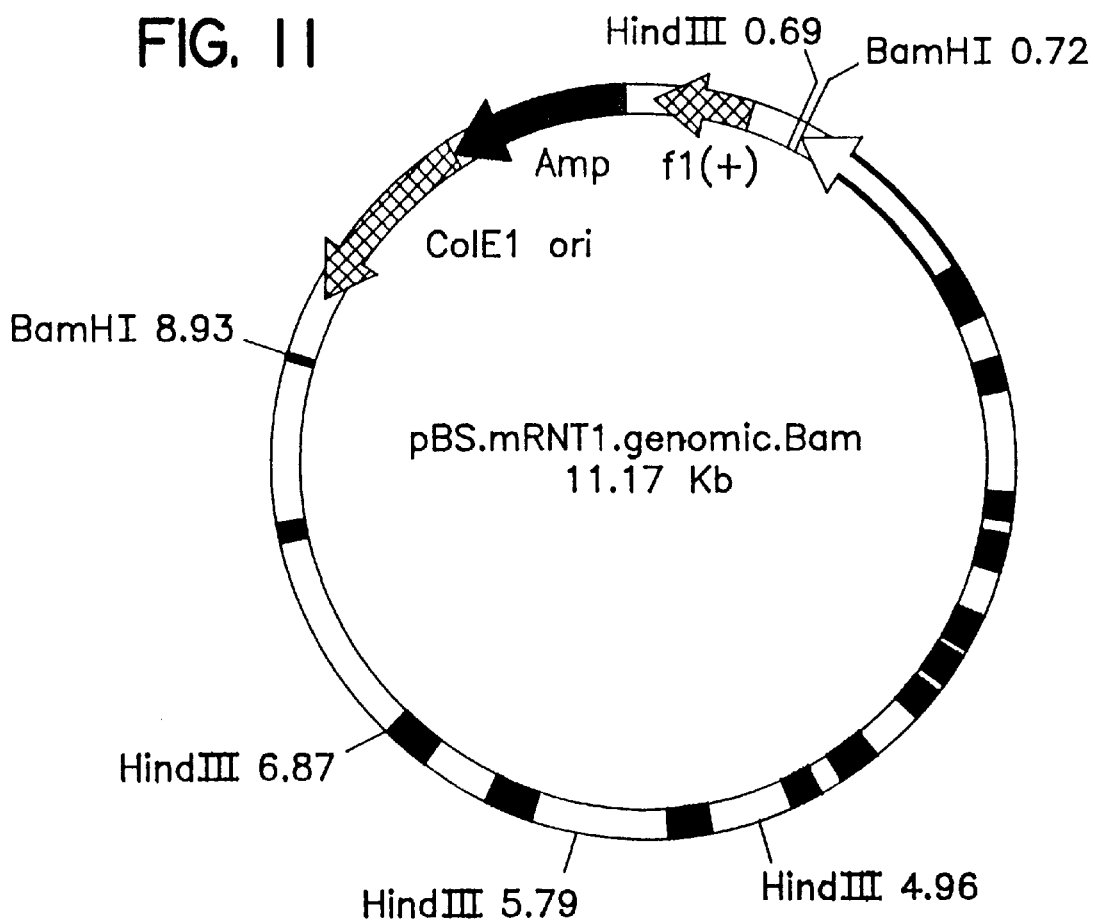
FIG. 11 shows the murine RENT1 genomic clone designated pBS.mRENT1.genomic.Bam.

A large (~5.5 kb) murine RENT1 genomic clone was identified after probing a 129/SV strain mouse genomic library (Stratagene) using a radiolabeled human cDNA fragment. An approximately 8.2 kb BamHI restriction fragment was subcloned into pBluescriptII/SK+ (Stratagene) and sequenced as described above. A 7 kb BamHI-NotI restriction fragment from the same genomic clone was subcloned and approximately 4.4 kb sequenced. Coding sequence was identified by aligning the conceptual translation of the human cDNA with that for the murine genomic clone using the MacVector 4.5.3 package of sequence analysis software (Kodak). The Rnt1 gene was also partially cloned from mouse liver. Degenerate PCR primers, encoding short peptide sequences which are identical between RENT1 and Upf1, were used for RT-PCR of mouse liver RNA. The primers LECYNCK (SEQ ID NO:28) and LEADYDK (SEQ ID NO:29) were used together, to retrieve an expected 414 bp RT-PCR product based on human and yeast sequences. Conceptual translation and homology analysis of 12.6 kb sequenced demonstrates that 1041 residues of the predicted murine protein, corresponding to residues 78 to 1118 in the human sequence, are encoded by 22 exons. Only 14 of 1041 residues differ between the characterized portions of the human and murine proteins suggesting that most residues in the mammalian rent1 proteins have a high degree of functional significance and are conserved in other mammalian regulators of NMRD. Alignment of the seven regions common to members of helicase superfamily I (21) for Upf1p, its homologues in human, mouse and S. pombe, along with Sen1 and Mov-10, reveal a conserved consensus that allows definition of this group of proteins as a distinct subset within the helicase superfamily. The entire genomic murine RENT1 sequence is present in FIG. 4 including the amino acid sequence. A murine RENT1 genomic clone is incorporated in the vector shown in FIG. 11. Additionally, a targeting vector using the murine RENT1 sequence for the creation of a knockout phenotype is shown in FIG. 10.

Example 3

Mapping the Rent1 Human and Murine Chromosomal Location

The Jackson Laboratory BSS interspecific backcross DNA panel was used to map the murine Rnt1 gene. This was accomplished by following the strain distribution pattern of a C57BL/6J-specific 1.6 kb Taq1 restriction fragment detected upon hybridization with a human RNT1 cDNA probe. The human probe detected a C57BL/6J-specific 1.6 kb TaqI restriction fragment, which was used to determine the map position of the murine gene. Rnt1 was found to map murine chromosome 8 between the micro satellite markers D8Mit5 and D8Mit78, a region synthetic with human chromosome 19p13.2-p13.11, Neurocan (Ncan) was the closest mapped murine gene (Raunch, et al., 1995) with zero crossovers in 83 mice. Subsequent typing of the NIGMS human/rodent somatic cell hybrid mapping panel (version 2, Coriell Cell Repositories) for human-specific HindIII restriction fragments unambiguously confirmed the human chromosome 19 localization for RNT1. Relevant data may be viewed on the World Wide Web at URL http://www.ncbi.nlm.nih.gov/XREFdb/. No apparent relevant mouse or human phenotypes are known to map to the specified regions of murine chromosome 8 or human chromosome 19, respectively. The murine hook (Hk) and quinky (Q) phenotypes map on mouse chromosome 8 with an offset from ten centromere of 26 and 38 cM, respectively. Both are characterized by tail deformities. Hook mice exhibit anal deformities while quinky mice show abnormal circling behavior.

Example 4

Sequence Analysis of Rent1

Direct sequencing predicted an ORF of 3,354 bp with 231 bp of 5' UTR and 103 bp of 3' UTR, excluding the poly(A) tail. The putative initiating methionine is encoded by an ATG that occurs within the context of a Kozak consensus sequence (12), 23 codons downstream of an in-frame translational terminator. Three tandem consensus polyadenylation signals (AATAAA) begin at positions 63, 70, and 76 of the 3' UTR, with initiation of the poly(A) tail at position 104. A comparison of the sequence of RENT1 with Upf1 indicates that, although the proteins differ at their amino and carboxyl termini, there is significant sequence homology within the central portions of the two proteins (amino acid 60–853 of Upf1 and amino acid 121–917 of rent1). Throughout their central portions, RENT1 and upf1 share 58% amino acid identity and 80% conservation. In addition, RENT1 and Upf1 share two zinc finger-like domains. These proteins also share motifs that a common to members of helicase superfamily I, including motifs that are thought to confer NTP-hydrolysis activity. Two of these motifs perfectly match the consensus sequences GXXXXGK(S/T) (SEQ ID NO:14) and DXXG (SEQ ID NP:15) (Dever et al., 1987). In addition, the sequence of RENT1 is identical to the sequence of Upf1 at the residues that, when altered, confer dominant-negative activity to Upf1 (Leeds et al., 1992). These similarities in the central portions of RENT1 and Upf1 suggest that RENT1 regulates NMRD in mammals. Although the central portion of RENT1 is similar to the central portion of Upf1, these proteins differ at both their amino and carboxyl termini.

To facilitate understanding the similarities and differences between RENT1 and Upf1, it is best to divide the protein sequence into 3 regions, A) N-terminus, B) body, and C) C-terminus. The bodies of the two proteins (aa 60–853 and 121–917 in Upf1 and rent1, respectively) show excellent alignment and a high degree of similarity. Throughout this region the two protein sequences show 58% residue identity and 80% conservation. Moreover, RENT1 is the first identified human protein sequence that contains all of the putative functional elements that are found in Upf1. These include the cysteine-rich zinc finger-like domains that serve a putative nucleotide-binding function and the motifs common to members of helicase superfamily 1 including those that are believed the confer NTP-hydrolysis activity. The first 2 NTP-hydrolysis motifs show a perfect match with the consensus GXXXXGK(S/T) (SEQ ID NO:14 and SEQ ID NO:25) and DXXG and are appropriately spaced (Dever, et al., 1987). The third sequence element, believed responsible for GTP-binding specificity, does not perfectly match the consensus NKXD. Although a consensus match is found in Upf1, the motif is not found at the predicted distance fro the second NTP-hydrolysis element, leaving in doubt its functional significance (Leeds, et al., 1992). RENT1 is a strong structural homologue of Upf1, and contains all of the known or putative functional elements found in the yeast protein. Current theory holds that coordinated nucleotide-binding, helicase, and NTPase activated may be essential for the proper interaction between nonsense transcripts and the factors that scan for premature termination codons and other relevant cis-acting elements (Czapliniski, et al., 1995).

The N- and C-terminal of RENT1 do not align with the corresponding regions of Upf1. The first notable difference is that the N-terminus of RENT1 is longer than that found in Upf1 (120 vs. 59 aa, respectively) and it contains a long (26 aa) stretch composed entirely of proline, glycine, and alanine residues that is not found in the yeast protein. While the functional significance of this region is unknown, PGA-rich stretches have been found to act as a direct transcriptional repressor (Catron, et al., 1995). It is also possible that helix-disturbing properties imposed by the high PG-content confers a favorable conformation to the molecule. If one excludes the PGA-rich region, certain similarities are evident between the N-terminal of RENT1 and Upf1. Both are relatively rich in serine and threonine (19 vs. 24% respectively) and acidic residues (D or E; 22 vs. 18% respectively). Such features are commonly seen in nucleotide-binding proteins with transactivation or transcriptional regulation properties (e.g. Calvert, et al., 1991; Seipel, et al., 1992). BLAST analysis of the isolated N-terminal sequence of RENT1 reveals homology to multiple homeobox/POU domain proteins that participate in transcriptional regulation. Homologous proteins that are known to interact with RNA include the Sis1 heat shock protein of veast and the Gr10 RNA-binding protein of B. napus (p=5.6e-07 and 1.2e-04, respectively). Of particular interest. Sis1 has been shown to localize to both the nucleus and cytoplasm, associated with 40S ribosomal subunits and smaller polysome, is required for the initiation of translation, and may mediate the association of protein complexes within the translation machinery (Luke, et al., 1991; Hong & Arndt, 1993).

The C-terminus of RENT1 is longer than that found in Upf1 (203 vs. 118 aa, respectively). Of note, both C-termini are rich in serine and glutamines (21 vs. 18%, respectively). The occurrence of the majority of these residues as SQ dipeptides (n=14) is a feature unique to the human protein. Many RNA recognition motif (RRM)-containing proteins have glutamine rich regions that are postulated to regulate multiple aspects of RNA processing (DeAngelo, et al., 1991). BLAST analysis of the isolated C-terminus of RENT1 demonstrated significant homology with the human or mouse EWS RNA-binding protein (p=8.9e-3). Interestingly, the N-termini of RENT1 and EWS both show a high frequency (60 vs. 90%, respectively) of Y, Q, S, T, G, A, and P residues. EWS has been proposed to participate in RNA synthesis and processing (Delattre, et al., 1992).

Like the N-terminus, the C-terminus of RENT1 (203 amino acid) is longer than the corresponding region of Upf1 (116 amino acid). Although divergence is seen at the extreme N- and C-termini, the large central regions of Upf1p and RENT1 (residues 60–853 and 121–917, respectively) show 58% identity and 80% conservation. Moreover, RENT1 is the first identified mammalian protein that contains all of the putative functional elements found in Upf1p including the cysteine-rich zinc finger-like domains that may participate in nucleotide binding, the domains with putative NTPase activity, and the motifs common to members of helicase superfamily I.

Example 5

Production of Dominant-negative Rent1

Dominant-negative versions of rent1 were produced by site-directed mutagenesis performed according to previously described methods (Dietz and Kendzior, 1994). The mutations used to produce dominant-negative versions of rent1 are similar to the mutations used to produce dominant-negative versions of Upf1 (Leeds et al., 1992). The RENT1 mutation in mammals which confers a dominant-negative phenotype on the protein parallels dominant negative Upf1 mutations in yeast.

Example 6

Expression of rent1

Conventional recombinant DNA techniques and gene expression methods can be used to express wild-type RENT1 or dominant-negative versions of RENT1 in a cell. A genetic construct for expressing the various versions of RENT1 is pβRNT1-NEO produced by modifying the vector pHβApr-1 (Gunning et al., 1987). pHβApr-1 contains the human β-actin promoter (~3 kb of 5' flanking sequence), 77 bp of β-actin 5' UTR contained in exon 1, and the entire β-actin intron 1 (including the splice donor and acceptor and the enhancer core sequence found therein), followed by a polylinker. To create pβRNT1-NEO, pHβApr-1 was modified by the addition of a neomycin resistance cassette. In addition, the RNT1 open reading frame, including a short region of the 5' UTR and the entire 3' UTR was subcloned into the polylinker of pHβApr-1. Expression of RENT1 from pβRNT1-NEO is driven by a cytomegalovirus (CMV) promoter. pβRNT1-NEO transcripts have a portion of the 5' UTR of β-actin at their 5' ends. This 5' tag is useful for distinguishing vector-derived transcripts from transcripts which are endogenous to the transfected cell. Northern analysis and RT-PCR can be used to distinguish the transcripts. Another set of constructs have the RNT1 open reading frame cloned in-frame with a sequence that encodes a hemagglutinin (HA) tag at the N-terminus of RENT1. The resulting rent1/HA fusion protein can be used in studies that employ immunohistochemical analysis such as those that required determining whether subcellular compartmental localization occurs in rent1 products.

Example 7

Analysis of Rent1 mRNA by Northern Blot

Prepared multiple human tissue Northern blots obtained from Clontech were probed with a 300 bp RENT1 cDNA fragment (encoding aa 644–745) or a b-actin cDNA probe (Clontech) according to manufacturer instructions. Northern blot analysis of poly(A) RNA shows a predominant transcript size of approximately 5.4 kb in all adult tissues tested. A less intense signal at approximately 3.7 kb is visible in all lanes, with an additional and significantly smaller hybridizing transcript unique to the pancreas. Additional tissues tested (spleen, thymus, prostate, testis, ovary, small intestine, colon, and peripheral blood leukocyte) all showed predominant ~5.4 1 b and less intense 3.7 kb bands, except in testes where equally intense signals were observed.

Example 8

Yeast Expression Vector Constructs for Rent1

Yeast constructs were prepared that express human rent1 protein. By modifying the allo suppression assay used to identify and clone the UPF genes (Leed, et al., 1991), one of ordinary skill in the art can determine whether expression of rent1 can complement the Upf1-deficient phenotype using a PLY38 yeast strain (MATa, ura3-52, his-38, SUF1-1, Upf1-2). This strain harbors a +1 frameshift mutation (his4–38) near the 5' end of the HIS4 transcript and also a SUF1-1 allele which encodes a glycine tRNA frameshift suppressor and allows low-level read through of the frameshift mutation. At both 30° C. and 37° C. PLY38 has a His+ phenotype, but upon reconstitution with wild-type Upf1 the cells are His- at 37° C. and fail to grow. Using a basic assay one of ordinary skill in the art can determine whether expression of rent1 in this genetic background can inhibit growth at 37° C. To optimize expression, the UPF1 and RNT1 ORFs were both subcloned into a 2-micron vector containing the MET25 promoter. MET25 promoter shows excellent performance in the expression of heterologous proteins in yeast, is not overly influenced by the respiratory status of the cell, and is inducible in the absence of methionine (Mumberg, et al., 1994). Expressing wild-type Upf1 in PLY38 at 37° C. using MET25 promoter, the growth phenotype was easily distinguishable from untransformed cells or transformed cells grown for 2 days in the presence of methionine.

Expression of heterologous genes in yeast is sensitive to the length and origin of the UTR sequences (reviewed in Romanos, et al., 1992). Yeast UTRs tend to be extremely short and RNA conformation in these regions, as dictated by the primary nucleotide sequence, may influence the trafficking and translation of transcripts. To address this issue, two additional yeast expression constructs were prepared. The first is a modification of pAD54LEu2 which drives expression of HA-tagged fusion proteins using the yeast alcohol dehydrogenase (ADH1) promoter and includes the yeast ADH 5'UTR, terminator, 3'UTR, and poly (A) signal. The URA3 was switched for the LEU2 selectable marker (enabling the vector for use in PLY38), and subcloned in the yeast and human ORFs for Upf1 and rent1 , respectively, downstream of and in-frame with the HA tag-encoding region. The RNT1 and UPF1 UTRs were not included in the constructs. These constructs are preferred because inhibition of expression by heterologous UTRs has been obviated, and one of ordinary still in the art can directly assay for expression of the fusion protein using anti-HA antibodies (Boehringer Mannheim). This vector can be used successfully for the expression of heterologous proteins in yeast. Additionally, the addition of an N-terminal epitope does not to inhibit the function of wild-type Upf1 (Cui, et al., 1995). These construct are designated pAD54-RNT1 or pAD54-UPF1.

Figure 5:
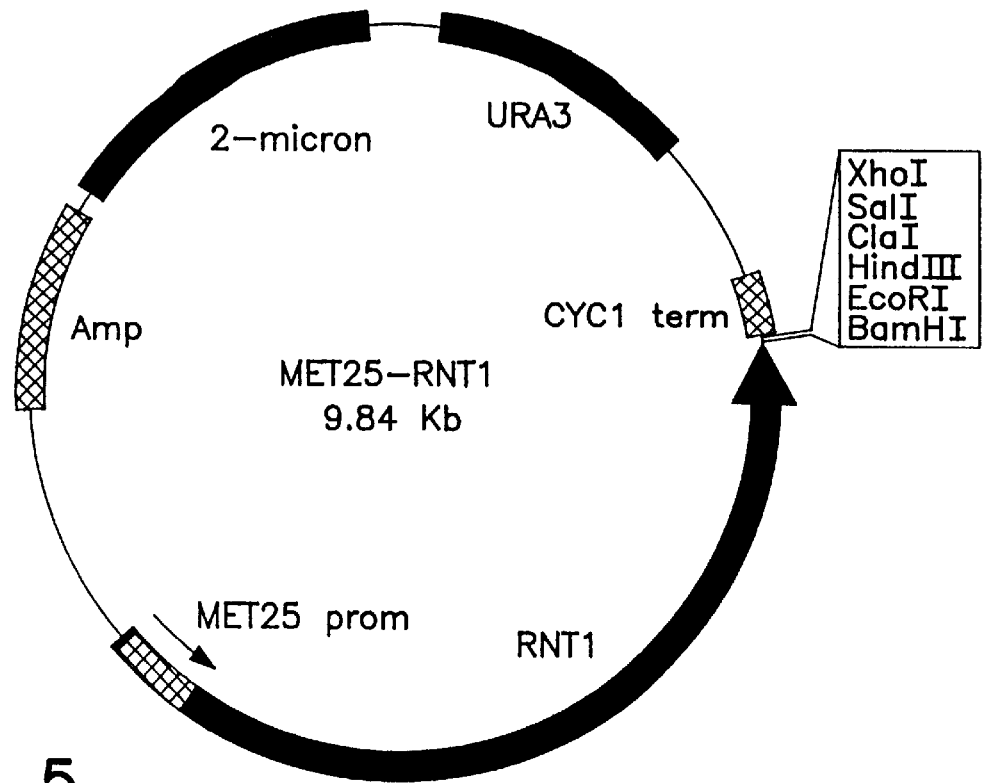
FIG. 5 shows the human RENT1 in a yeast recombinant expression vector construct MET25-RENT1.
Figure 6:
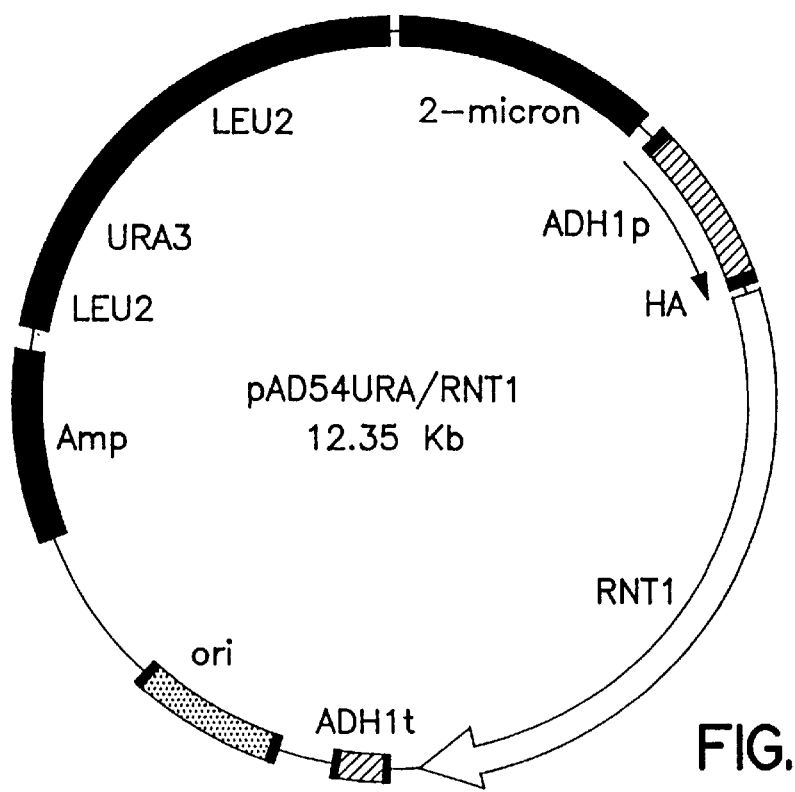
FIG. 6 shows the human RENT1 in a yeast recombinant expression vector construct pAD54URA-RENT1.

A second set of constructs designated pMET25-RNT1 or UPF make use of a vector that expresses wild-type Upf1 . To prevent possible interference by heterologous UTRs we substituted the ORF of RNT1 for that of UPF1, leaving in place the 5'UTR, initiating methionine, terminator, and 3'UTR of the UPF1 gene. A PLY38 strain (MATa, ura3-52, his4-38, SUF1-1, Upf1-2) harboring a +1 frameshift mutation (his4-38) near the 5' end of the HIS4 transcript was used to construct the RNT1 yeast expression vector. The strain also contains the SUF1-1 allele which encodes a glycine tRNA frameshift suppressor and allows low-level read through of the frameshift mutation. At both 30° C. and 37° C. this strain has a His+phenotype, but upon reconstitution with wild-type Upf1 the cells are His-at 37° C. and fail to grow. A test to determine whether rent1 can substitute for Upf1 in this capacity can be established using a previously described allosuppression assay (Leeds, et al., 1991: 1992). Briefly, PLY38 transformants containing pmt.-UPF1, pmt.-RNT1, or pmt. (without insert) can be selected on uracil-deficient media. Three independent transformants for each can be grown in liquid culture to OD600 between 0.4–0.6. Four μl aliquot of serial diluted cultures (undiluted, 1:100, 1:100, and 1:1000) can be plated on solid media lacking methane (for promoter induction), uracil, and histidine. Growth can be monitored at both 30 and 37° C. If pmt.-RNT1 fails to complement the Upf1-phenotype, then PLY38 transformants containing pAD54-UPF1, pAD54-RNT1, and pAD54 (under the control of the constitutive ADHI promoter) can be created and assayed as above. The advantage to this second set of vectors is that they encode an N-terminal HA tag. Additional yeast recombinant expression vector contstructs are shown in FIGS. 5 and 6 and are presented for illustrative purposes for one of ordinary skill in the art to demonstrate other vector constructs can be created using the teachings supplied herein.

If complementation in yeast is seen, this can allow us to interrogate the functional significance of specific residues of rent1 in an efficient and powerful yeast system. For example, yeast strains PLY154 (MATα, ura3-52, his4-38, upf1 Δ1, leu2-1, rpb1-1) is particularly useful to measure the decay rates of HIS4 transcripts. The temperature-sensitive rbp1-1 polymerase II allele allows rapid cessation of new transcription after a shift from 25 to 36° C. Quantitative Northern blotting can be performed on RNA isolated from aliqouts of cells that are removed at specified time intervals after the temperature shift (Parker, et al., 1991). This assay can be used to compare the relative strength of various putative dominant-negative and loss-of-function mutations in RNT1. First, PLY154 can be complemented with wild-type rent1. The resulting strain (PLY154R) can be transformed with constructs expressing putative dominant-negative forms of rent1. The decay rate of His4 transcripts can then be determined can be assayed in PLY154 without prior reconstitution of NMRD function with wild-type rent1. Alleles showing the most desirable functional characteristics can be targeted for use in mammalian cell culture experimentation. Also, if none of the mutations in Upf1 have similar effects upon the function of rent1, it can be necessary to screen for dominant-negative forms of rent1 and then transforming with a RENT1 expression construct that has undergone random mutagenesis (Leeds, et al., 1992). Transformants that are able to grow at 37° C. can harbor dominant-negative RNT1 alleles which can then be characterized and used in further experimentation.

Example 9

Human RENT1 Protein (AA 121–917) Restores NMRD in Yeast Deficient for UPF1P Activity To explore the functional properties of rent1, we determined whether its expression in yeast deficient for Upf1p activity could restore NMRD using a modification of the allosupression assay originally used to identify Upf1p. We utilized the PLY38 strain (MATa ura3-52 his4-38 SUF1-1 upf1-2) that harbors a +1 frameshift mutation in the HIS4 transcript and a tRNA frameshift suppressor with decreased efficiency at elevated temperatures. This strain grows in histidine-deficient media due to the combination of tRNA suppressor activity and the stability of his4-38 mRNA in the absence of Upf1p. Reconstitution with Upf1p activity decreases his4-38 message abundance and causes growth failure at high culture temperatures which are less permissive for suppressor tRNA function.

Transformation of yeast strain PLY38 with a RENT1 expression construct failed to complement the yeast Upf1p-deficient phenotype. The same result was obtained when the yeast ADH1 UTRs were placed flanking the entire RENT1 coding sequence (data not shown). To test whether the divergence at the extreme N- and C-termini conferred species-specific functional constraints, we prepared a construct (pMET-Chimera) encoding the Upf1p 5' UTR and N-terminus (aa 1–59), the body of the human protein (aa 121–917), and the Upf1p C-terminus (aa 854–971) and 3' UTR. A dramatic inhibition of growth was seen in pMET25-Chimera transformants at elevated temperatures indicating that the central portion of the human rent1 protein is capable of functioning in yeast and rescuing a mutant yeast phenotype that has a deficient Upf1p protein.

Example 9

Mammalian Expression Vector Constructs for Rent1

To express rent1 in mammalian cells, mammalian expression constructs were created. Each construct was made in multiple forms, either expressing wild-type RENT1 or one of two putative dominant-negate forms. The dominant-negative mutations were created by oligonucleotide-mediated site-directed mutagenesis (Dietz & Kendzior, 1994). The site and character of the mutations were chosen based upon previous work with Upf1 (Leeds, et al., 1992). Two mutations in UPF1, G556D, and R779C, conferred the strongest dominant-negative phenotype. Corresponding mutations were made in the ORF of human RNT1 (G619D and R843C).

The mammalian expression constructs designated pβRNT1-NEO is based upon a modification of the vector pHβApr-1 (Gunning, et al., 1987). The vector contains the human β-actin promoter (−3 kb of 5' flanking sequence), the 77 bp of β-actin 5' UTR contained in exon 1, and the entire β-actin intron 1 including the splice donor and acceptor and the enhancer core sequence found therein, followed by a polylinker. This vector supports extremely high expression levels in a large variety of mammalian cells (Gunning, et al., 1987). The vector was modified by the addition of a neomycin resistance cassette and subcloned with the RNT1 ORF, including a short region of 5'UTR and the entire 3' UTR, into the polylinker. Resultant transcripts are 5'-tagged with the β-actin 5' UTR enabling the discrimination of endogenous transcripts from vector-derived transcripts using either Northern analysis or RT-PCR-based methods. The pCMV-RNT1 constructs contain the RNT1 ORF (wild-type and multiple putative dominant-negative forms) driven by the CMV promoter. Immunohistochemical analysis of the fusion protein permits determination of subcellular compartmental localization of rent1. The final set of constructs, termed pHA-RNT1 , have the RNT1 ORF cloned in-frame with a sequence that encodes an N-terminal HA tag which are useful for transient transfection studies.

Figure 7:
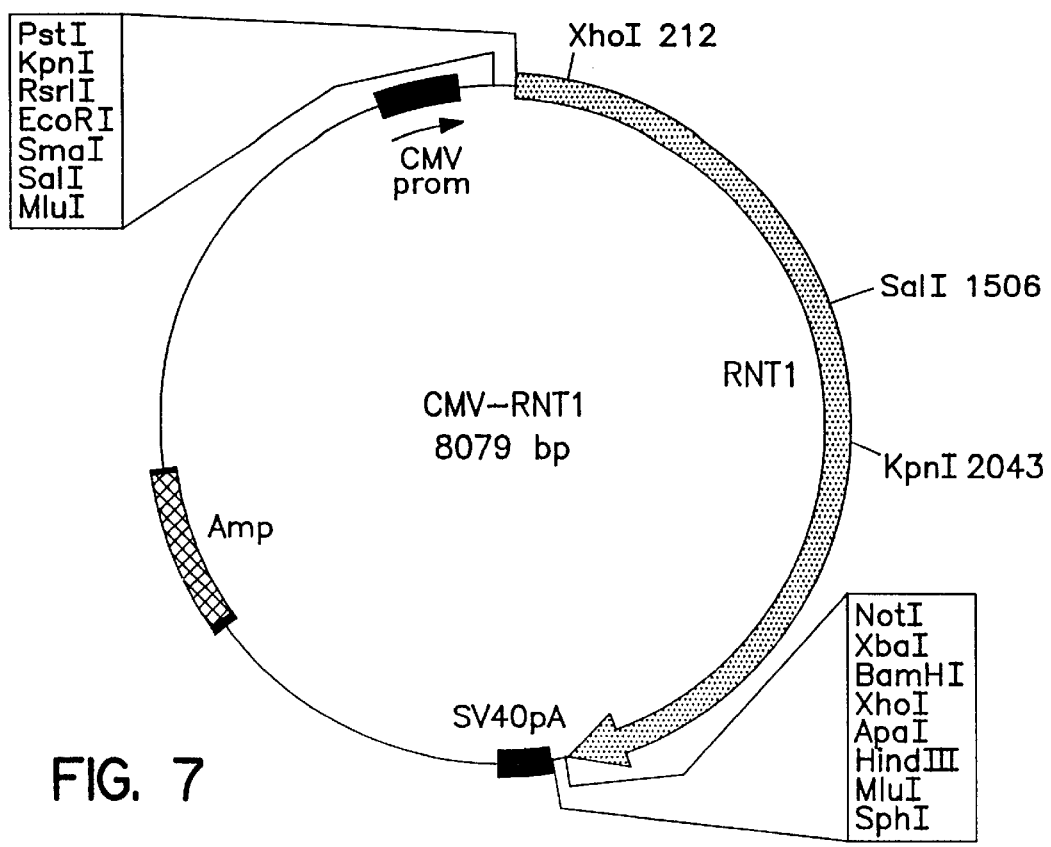
FIG. 7 shows the human RENT1 in a mammalian recombinant expression vector construct CMV-RENT1.
Figure 8:
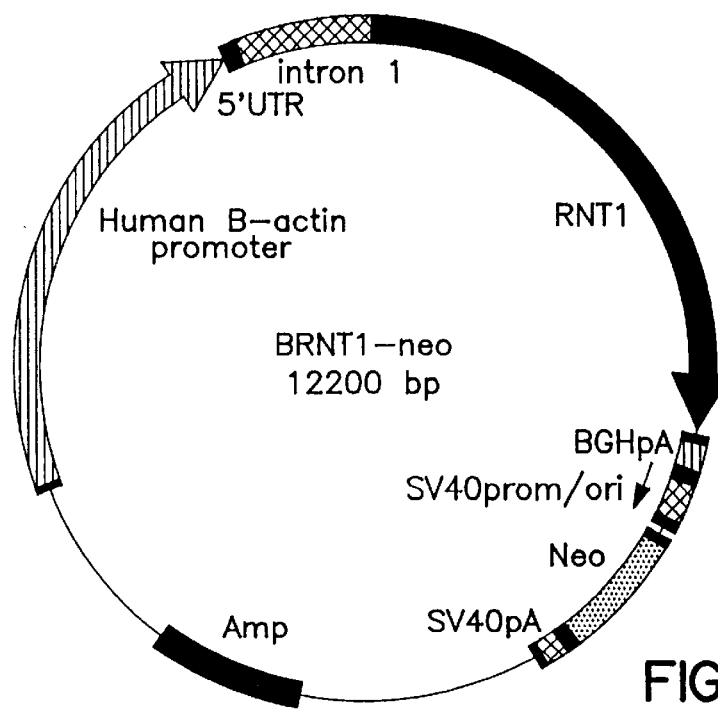
FIG. 8 shows the human RENT1 in a mammalian recombinant expression vector construct BRENT1-neo.
Figure 9:
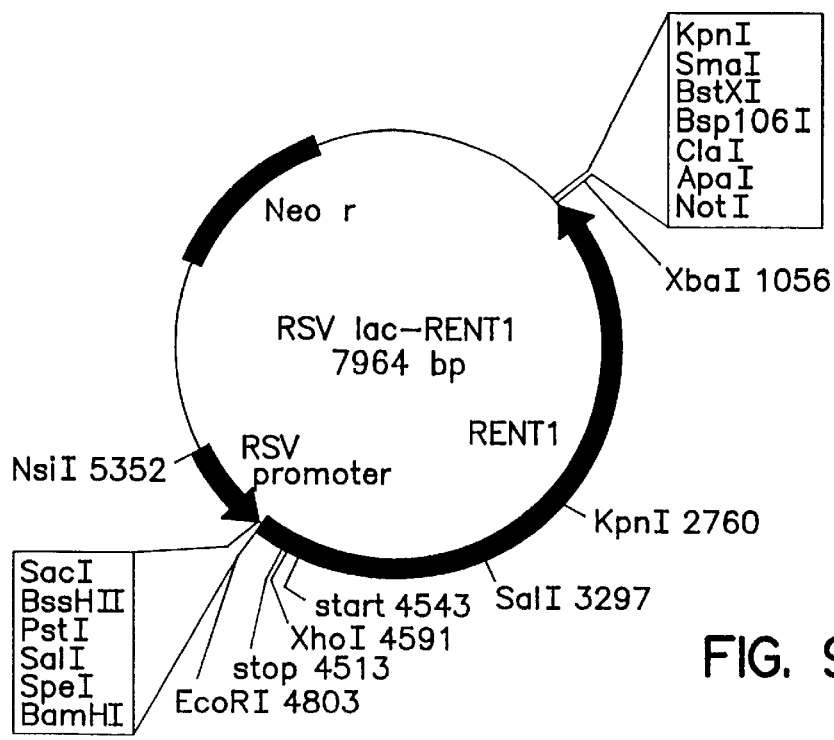
FIG. 9 shows the human RENT1 in a mammalian recombinant expression vector construct RSV▲lac-RENT1.

To construct pMET25-RENT, an XhoI fragment containing the entire RENT1 coding region was inserted into the SmaI site of p426MET25. The BamHI fragment from pBM272UPF1 was inserted into the BamHI site of p426MET25 to create pMET25-UPF1. pMET25-CHIMERA was constructed using high fidelity Taq polymerase (Pfu, Stratagene) with the addition of restriction sites for cloning as follows: The 5' region (5' UTR and sequence encoding aa 1–59) of Upf1p was amplified by PCR with UPF-Bam-S(5'-GGATCCCATCAGGAAAGAAG-3') (SEQ ID NO:16) and UPF-Sal-AS (5'-GTCGACTGAAGCTGAAGG CGAACGG-3') (SEQ ID NO:17). The 3' region of Upf1p (encoding aa 854–971 ancd 3' UTR) was amplified by UPF-Not-S (5'-GCGGCCGCGAAAGACTGAACGGCCAAT-3') (SEQ ID NO:18) and UPF-Hind-AS (5'-AAGCTTAT-CCAAAGTATATTGGACCGG-3') (SEQ ID NO:19). The central region of RENT1 (encoding aa 121–917) was amplified with RNT-SalS-1 (5'-ACGCGTCGACCACGCCTGCAGTACTGTGGAATAC-3') (SEQ ID NO:20) and RNT-NotAS-1 (5'-ATAAGAATGCGGCCGCGGCTGCTGAACGCATGA-GGCTCTCACG-3') (SEQ ID NO:21). Each PCR product was subcloned into the SmaI site of pBluescriptII/SK+ (Stratagene) and excised with the appropriate restriction enzymes and ligated into p426MET25 digested with BamHI and HindIII. pMET25-y5' was constructed by inserting the 5' UPF1 BamHI/SalI fragment into BamHI/SalI digested p426MET25. Transformants were grown in liquid culture to a similar OD600 and 4 ml aliquots of serially diluted cultures were plated on solid media lacking methionine (for promoter induction), uracil (for selection of transformants), and histidine (as a marker for the stability of his4-38 transcripts).Additional mammalian recombinant expression vector contstructs are shown in FIGS. 7, 8, and 9 and are presented for illustrative purposes for one of ordinary skill in the art to demonstrate other vector constructs can be created using the teachings supplied herein.

Example 10

Disease Diagnosis Using NMRD and Rnt1 Expression

The FBNI Genotype-specific Efficiency of NMRD Modulates Phenotypic Severity in the Marfin Syndrome A 4 bp tandem insertion was identified at nucleotide 5138 in one allele in the gene (FBN1) encoding fibrillin-1 of a patient with extremely mild Marfan syndrome (MFS) disease (Dietz, et al., 1993b). The transcript level from the mutant allele was 6% of the fraction produced by the wild-type allele. While mutations associated with equal levels of mRNA from the wild-type and mutant alleles cause classic and severe MFS disease, the phenotype in this patient is restricted to mitral valve prolapse, long-bone overgrowth, and striae distinae. This clinical presentation fails to meet the diagnosis criteria for MFS and would be more accurately characterized as the MASS phenotype. One hypothesis for the pathogenic basis for this mild phenotype suggests that a low-level of mutant transcript and protein, relative to that from the wild-type allele, results in a favorable stoichiometry for the formation of structurally normal multimers, albeit in reduced amounts, and hence mild disease. Experience with additional nonsense alleles causing MFS allowed us to test this hypothesis. It was observed that mutant alleles associated with levels of –15% or greater of mutant transcript, relative to that from the wild-type allele, were associated with severe MSF disease, while those associated with <6% were associated with distinctly milder phenotypes of MSF. As observed in the disease osteogenesis imperfecta, perhaps some critical threshold of mutant transcript and monomer, possibly between 6 and 16% of wild-type levels, is necessary for the expression of classic MFS.

Fibrillin-1 metabolism was examined in cell lines harboring nonsense alleles (Aoyama, et al., 1993; 1994). Fibroblasts from patients with defined FBNI mutations were grown in the presence of radiolabeled cysteine. The cultures were then "chased" with unlabeled media for specific time intervals prior to the determination of radiolabeled fibrillin content in the cellular compartment and in the extracellular matrix. Interestingly, all mutations associated with ≧15% mutant transcript levels showed 50% fibrillin-1 synthesis, relative to control lines, but severely impaired matrix utilization of synthesized protein, presumed to be product from the wild-type allele. In contrast, the mutation associated with a 6% mutant transcript level also showed approximately 50% synthesis, but all of this protein was effectively incorporated into the matrix.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

---

What is claimed:

1. A substantially pure rent1 polypeptide consisting of the amino acid sequence of SEQ ID NO:2 or SEQ ID NO:4.

2. The polypeptide of claim 1 consisting of the amino acid sequence of SEQ ID NO:2.

3. The polypeptide of claim 1 consisting of the amino acid sequence of SEQ ID NO:4.

4. A substantially pure rent1 polypeptide comprising the amino acid sequence of SEQ ID NO:2 or a variant of SEQ ID NO:2 consisting of conservative amino acid substitutions of SEQ ID NO:2.

* * * * *

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
        (A) LENGTH: 3760 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO:1:

```
GAATTCCCGG GTCGACCCAC GCGTCCGAGC GGCTGGCGGC TTCGAGGGGA GCTGAGGCGC      60

GGAGGGGCTC GGCGGCAGCG GCGGCGGCTC GGCACTGTTA CCTCTCGGTC CGGCTGGCGC     120

CGGGGCGGGC GGTTTGGTCC TTTCCGGGCG CGCGGGGGCG ACAGCGGCAG CGACCCGAGG     180

CCTGCGGCCT AGGCCTCAGC GCGGCGGCGG GCTCGAGTGC AGCGCGGAAC CGGCCCGAGG     240

GCCCTACCCG GAGGCACCAT GAGCGTGGAG GCGTACGGGC CCAGCTCGCA GACTCTCACT     300
```

```
TTCCTGGACA CGGAGGAGGC CGAGCTGCTT GGCGCCGACA CACAGGGCTC CGAGTTCGAG    360

TTCACCGACT TTACTCTTCC TAGCCAGACG CAGACGCCCC CCGGCGGCCC CGGCGGCCCG    420

GGCGGTGGCG GCGCGGGAGG CCCGGGCGGC GCGGGCGCGG GCGCTGCGGC GGGACAGCTC    480

GACGCGCAGG TTGGGCCCGA AGGCATCCTG CAGAACGGGG CTGTGGACGA CAGTGTAGCC    540

AAGACCAGCC AGTTGTTGGC TGAGTTGAAC TTCGAGGAAG ATGAAGAAGA CACCTATTAC    600

ACGAAGGACC TCCCCATACA CGCCTGCAGT TACTGTGGAA TACACGATCC TGCCTGCGTG    660

GTTTACTGTA ATACCAGCAA GAAGTGGTTC TGCAACGGAC GTGGAAATAC TTCTGGCAGC    720

CACATTGTAA ATCACCTTGT GAGGGCAAAA TGCAAAGAGG TGACCCTGCA CAAGGACGGG    780

CCCCTGGGGG AGACAGTCCT GGAGTGCTAC AACTGCGGCT GTCGCAACGT CTTCCTCCTC    840

GGCTTCATCC CGGCCAAAGC TGACTCAGTG GTGGTGCTGC TGTGCAGGCA GCCCTGTGCC    900

AGCCAGAGCA GCCTCAAGGA CATCAACTGG GACAGCTCGC AGTGGCAGCC GCTGATCCAG    960

GACCGCTGCT TCCTGTCCTG GCTGGTCAAG ATCCCCTCCG AGCAGGAGCA GCTGCGGGCA   1020

CGCCAGATCA CGGCACAGCA GATCAACAAG CTGGAGGAGC TGTGGAAGGA AAACCCTTCT   1080

GCCACGCTGG AGGACCTGGA GAAGCCGGGG GTGGACGAGG AGCCGCAGCA TGTCCTCCTG   1140

CGGTACGAGG ACGCCTACCA GTACCAGAAC ATATTCGGGC CCCTGGTCAA GCTGGAGGCC   1200

GACTACGACA AGAAGCTGAA GGAGTCCCAG ACTCAAGATA ACATCACTGT CAGGTGGGAC   1260

CTGGGCCTTA CAAGAAGAG AATCGCCTAC TTCACTTTGC CCAAGACTGA CTCTGACATG   1320

CGGCTCATGC AGGGGGATGA GATATGCCTG CGGTACAAAG GGGACCTTGC GCCCCTGTGG   1380

AAAGGGATCG GCCACGTCAT CAAGGTCCCT GATAATTATG GCGATGAGAT CGCCATTGAG   1440

CTGCGGAGCA GCGTGGGTGC ACCTGTGGAG GTGACTCACA ACTTCCAGGT GGATTTTGTG   1500

TGGAAGTCGA CCTCCTTTGA CAGGATGCAG AGCGCATTGA AAACGTTTGC CGTGGATGAG   1560

ACCTCGGTGT CTGGCTACAT CTACCACAAG CTGTTGGGCC ACGAGGTGGA GGACGTAATC   1620

ATCAAGTGCC AGCTGCCCAA GCGCTTCACG GCGCAGGCCC TCCCCGACCT CAACCACTCC   1680

CAGGTTTATG CCGTGAAGAC TGTGCTGCAA AGACCACTGA GCCTGATCCA GGGCCCGCCA   1740

GGCACGGGGA AGACGGTGAC GTCGGCCACC ATCGTCTACC ACCTGGCCCG GCAAGACAAC   1800

GGGCCGGTGC TGGTGTGTGC TCCGAGCAAC ATCGCCGTGG ACCAGCTAAC GGAGAAGATC   1860

CACCAGACGG GGCTAAAGGT CGTGCGCCTC TGCCCCAAGA GCCGTGAGGC CATCGACTCC   1920

CCGGTGTCTT TTCTGGCCCT GCACAACCAG ATCAGGAACA TGGACAGCAT GCCTGAGCTG   1980

CAGAAGCTGC AGCAGCTGAA AGACGAGACT GGGGAGCTGT CGTCTGCCGA CGAGAAGCGG   2040

TACCGGGCCT TGAAGCGCAC CGCAGAGAGA GAGCTGCTGA TGAACGCAGA TGTCATCTGC   2100

TGCACATGTG TGGGCGCCGG TGACCCGAGG CTGGCCAAGA TGCAGTTCCG CTCCATTTTA   2160

ATCGACGAAA GCACCCAGGC CACCGAGCCG GAGTGCATGG TTCCCGTGGT CCTCGGGGCC   2220

AAGCAGCTGA TCCTTGTAGG CGACCACTGC CAGCTGGGCC CAGTGGTGAT GTGCAAGAAG   2280

GCGGCCAAGG CCGGGCTGTC ACAGTCGCTC TTCGAGCGCC TGGTGGTGCT GGGCATCCGG   2340

CCCATCCGCC TGCAGGTCCA GTACCGGATG CACCCTGCAC TCAGCGCCTT CCCATCCAAC   2400

ATCTTCTACG AGGGCTCCCT CCAGAATGGT GTCACTGCAG CGGATCGTGT GAAGAAGGGA   2460

TTTGACTTCC AGTGGCCCCA ACCCGATAAA CCGATGTTCT TCTACGTGAC CCAGGGCCAA   2520

GAGGAGATTG CCAGCTCGGG CACCTCCTAC CTGAACAGGA CCGAGGCTGC GAACGTGGAG   2580

AAGATCACCA CGAAGTTGCT GAAGGCAGGC GCCAAGCCGG ACCAGATTGG CATCATCACG   2640
```

-continued

```
CCCTACGAGG GCCAGCGCTC CTACCTGGTG CAGTACATGC AGTTCAGCGG CTCCCTGCAC    2700

ACCAAGCTCT ACCAGGAGGT GGAGATCGCC AGTGTGGACG CCTTTCAGGG ACGCGAGAAG    2760

GACTTCATCA TCCTGTCCTG TGTGCGGGCC AACGAGCACC AAGGCATTGG CTTTTTAAAT    2820

GACCCCAGGC GTCTGAACGT GGCCCTGACC AGAGCAAGGT ATGGCGTCAT CATTGTGGGC    2880

AACCCGAAGG CACTATCAAA GCAGCCGCTC TGGAACCACC TGCTGATCTT CTATAAGGAG    2940

CAGAAGGTGC TGGTGGAGGG GCCGCTCAAC AACCTGCGTG AGAGCCTCAT GCAGTTCAGC    3000

AAGCCACGGA AGCTGGTCAA CACTATCAAC CCGGGAGCCC GCTTCATGAC CACAGCCATG    3060

TATGATGCCC GGGAGGCCAT CATCCCAGGC TCCGTCTATG ATCGGAGCAG CCAGGGCCGG    3120

CCTTCCAGCA TGTACTTCCA GACCCATGAC CAGATTGGCA TGATCAGTGC CGGCCCTAGC    3180

CACGTGGCTG CCATGAACAT TCCCATCCCC TTCAACCTGG TCATGCCACC CATGCCACCG    3240

CCTGGCTATT TTGGACAAGC CAACGGGCCT GCTGCAGGGC GAGGCACCCC GAAAGGCAAG    3300

ACTGGTCGTG GGGACGCCA AAGAACCGC TTTGGGCTTC CTGGACCCAG CCAGACTAAC    3360

CTCCCCAACA GCCAAGCCAG CCAGGATGTG GCGTCACAGC CCTTCTCTCA GGGCGCCCTG    3420

ACGCAGGGCT ACATCTCCAT GAGCCAGCCT TCCCAGATGA GCCAGCCCGG CCTCTCCCAG    3480

CCGGAGCTGT CCCAGGACAG TTACCTTGGT GACGAGTTTA AATCACAAAT CGACGTGGCG    3540

CTCTCACAGG ACTCCACGTA CCAGGGAGAG CGGGCTTACC AGCATGGCGG GGTGACGGGG    3600

CTGTCCCAGT ATTAAAAGGT GGCGGCGGAA GAGCTAAGCA ACGTGGCTTA GTCCATCAGC    3660

ATCTTATTCT GGGTAATAAA AAATAAAAAT AAACGGATAC CTGTTTTCCA CTGCTAAAAA    3720

AAAAAAAAAA AAAGAATTCC CGGGTCGACC CACGCGTCCG                         3760
```

(2) INFORMATION FOR SEQ ID NO:2:

(i) SEQUENCE CHARACTERISTICS:
        (A) LENGTH: 1118 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Val Glu Ala Tyr Gly Pro Ser Ser Gln Thr Leu Thr Phe Leu
  1               5                  10                  15

Asp Thr Glu Glu Ala Glu Leu Leu Gly Ala Asp Thr Gln Gly Ser Glu
             20                  25                  30

Phe Glu Phe Thr Asp Phe Thr Leu Pro Ser Gln Thr Gln Thr Pro Pro
         35                  40                  45

Gly Gly Pro Gly Gly Pro Gly Gly Gly Ala Gly Gly Pro Gly Gly
     50                  55                  60

Ala Gly Ala Gly Ala Ala Ala Gly Gln Leu Asp Ala Gln Val Gly Pro
 65                  70                  75                  80

Glu Gly Ile Leu Gln Asn Gly Ala Val Asp Asp Ser Val Ala Lys Thr
             85                  90                  95

Ser Gln Leu Leu Ala Glu Leu Asn Phe Glu Glu Asp Glu Glu Asp Thr
            100                 105                 110

Tyr Tyr Thr Lys Asp Leu Pro Ile His Ala Cys Ser Tyr Cys Gly Ile
        115                 120                 125

His Asp Pro Ala Cys Val Val Tyr Cys Asn Thr Ser Lys Lys Trp Phe
    130                 135                 140

Cys Asn Gly Arg Gly Asn Thr Ser Gly Ser His Ile Val Asn His Leu
145                 150                 155                 160
```

```
Val Arg Ala Lys Cys Lys Glu Val Thr Leu His Lys Asp Gly Pro Leu
                165                 170                 175

Gly Glu Thr Val Leu Glu Cys Tyr Asn Cys Gly Cys Arg Asn Val Phe
            180                 185                 190

Leu Leu Gly Phe Ile Pro Ala Lys Ala Asp Ser Val Val Val Leu Leu
        195                 200                 205

Cys Arg Gln Pro Cys Ala Ser Gln Ser Ser Leu Lys Asp Ile Asn Trp
    210                 215                 220

Asp Ser Ser Gln Trp Gln Pro Leu Ile Gln Asp Arg Cys Phe Leu Ser
225                 230                 235                 240

Trp Leu Val Lys Ile Pro Ser Glu Gln Glu Gln Leu Arg Ala Arg Gln
            245                 250                 255

Ile Thr Ala Gln Gln Ile Asn Lys Leu Glu Glu Leu Trp Lys Glu Asn
        260                 265                 270

Pro Ser Ala Thr Leu Glu Asp Leu Glu Lys Pro Gly Val Asp Glu Glu
    275                 280                 285

Pro Gln His Val Leu Leu Arg Tyr Glu Asp Ala Tyr Gln Tyr Gln Asn
290                 295                 300

Ile Phe Gly Pro Leu Val Lys Leu Glu Ala Asp Tyr Asp Lys Lys Leu
305                 310                 315                 320

Lys Glu Ser Gln Thr Gln Asp Asn Ile Thr Val Arg Trp Asp Leu Gly
            325                 330                 335

Leu Asn Lys Lys Arg Ile Ala Tyr Phe Thr Leu Pro Lys Thr Asp Ser
            340                 345                 350

Asp Met Arg Leu Met Gln Gly Asp Glu Ile Cys Leu Arg Tyr Lys Gly
        355                 360                 365

Asp Leu Ala Pro Leu Trp Lys Gly Ile Gly His Val Ile Lys Val Pro
    370                 375                 380

Asp Asn Tyr Gly Asp Glu Ile Ala Ile Glu Leu Arg Ser Ser Val Gly
385                 390                 395                 400

Ala Pro Val Glu Val Thr His Asn Phe Gln Val Asp Phe Val Trp Lys
            405                 410                 415

Ser Thr Ser Phe Asp Arg Met Gln Ser Ala Leu Lys Thr Phe Ala Val
            420                 425                 430

Asp Glu Thr Ser Val Ser Gly Tyr Ile Tyr His Lys Leu Leu Gly His
        435                 440                 445

Glu Val Glu Asp Val Ile Ile Lys Cys Gln Leu Pro Lys Arg Phe Thr
    450                 455                 460

Ala Gln Ala Leu Pro Asp Leu Asn His Ser Gln Val Tyr Ala Val Lys
465                 470                 475                 480

Thr Val Leu Gln Arg Pro Leu Ser Leu Ile Gln Gly Pro Pro Gly Thr
            485                 490                 495

Gly Lys Thr Val Thr Ser Ala Thr Ile Val Tyr His Leu Ala Arg Gln
            500                 505                 510

Asp Asn Gly Pro Val Leu Val Cys Ala Pro Ser Asn Ile Ala Val Asp
        515                 520                 525

Gln Leu Thr Glu Lys Ile His Gln Thr Gly Leu Lys Val Val Arg Leu
    530                 535                 540

Cys Pro Lys Ser Arg Glu Ala Ile Asp Ser Pro Val Ser Phe Leu Ala
545                 550                 555                 560

Leu His Asn Gln Ile Arg Asn Met Asp Ser Met Pro Glu Leu Gln Lys
            565                 570                 575
```

-continued

```
Leu Gln Gln Leu Lys Asp Glu Thr Gly Glu Leu Ser Ser Ala Asp Glu
                580                 585                 590

Lys Arg Tyr Arg Ala Leu Lys Arg Thr Ala Glu Arg Glu Leu Leu Met
            595                 600                 605

Asn Ala Asp Val Ile Cys Cys Thr Cys Val Gly Ala Gly Asp Pro Arg
610                 615                 620

Leu Ala Lys Met Gln Phe Arg Ser Ile Leu Ile Asp Glu Ser Thr Gln
625                 630                 635                 640

Ala Thr Glu Pro Glu Cys Met Val Pro Val Leu Gly Ala Lys Gln
                645                 650                 655

Leu Ile Leu Val Gly Asp His Cys Gln Leu Gly Pro Val Val Met Cys
                660                 665                 670

Lys Lys Ala Ala Lys Ala Gly Leu Ser Gln Ser Leu Phe Glu Arg Leu
            675                 680                 685

Val Val Leu Gly Ile Arg Pro Ile Arg Leu Gln Val Gln Tyr Arg Met
690                 695                 700

His Pro Ala Leu Ser Ala Phe Pro Ser Asn Ile Phe Tyr Glu Gly Ser
705                 710                 715                 720

Leu Gln Asn Gly Val Thr Ala Ala Asp Arg Val Lys Lys Gly Phe Asp
                725                 730                 735

Phe Gln Trp Pro Gln Pro Asp Lys Pro Met Phe Phe Tyr Val Thr Gln
                740                 745                 750

Gly Gln Glu Glu Ile Ala Ser Ser Gly Thr Ser Tyr Leu Asn Arg Thr
            755                 760                 765

Glu Ala Ala Asn Val Glu Lys Ile Thr Thr Lys Leu Leu Lys Ala Gly
770                 775                 780

Ala Lys Pro Asp Gln Ile Gly Ile Ile Thr Pro Tyr Glu Gly Gln Arg
785                 790                 795                 800

Ser Tyr Leu Val Gln Tyr Met Gln Phe Ser Gly Ser Leu His Thr Lys
                805                 810                 815

Leu Tyr Gln Glu Val Glu Ile Ala Ser Val Asp Ala Phe Gln Gly Arg
            820                 825                 830

Glu Lys Asp Phe Ile Ile Leu Ser Cys Val Arg Ala Asn Glu His Gln
            835                 840                 845

Gly Ile Gly Phe Leu Asn Asp Pro Arg Arg Leu Asn Val Ala Leu Thr
850                 855                 860

Arg Ala Arg Tyr Gly Val Ile Val Gly Asn Pro Lys Ala Leu Ser
865                 870                 875                 880

Lys Gln Pro Leu Trp Asn His Leu Leu Ile Phe Tyr Lys Glu Gln Lys
                885                 890                 895

Val Leu Val Glu Gly Pro Leu Asn Asn Leu Arg Glu Ser Leu Met Gln
            900                 905                 910

Phe Ser Lys Pro Arg Lys Leu Val Asn Thr Ile Asn Pro Gly Ala Arg
            915                 920                 925

Phe Met Thr Thr Ala Met Tyr Asp Ala Arg Glu Ala Ile Ile Pro Gly
            930                 935                 940

Ser Val Tyr Asp Arg Ser Ser Gln Gly Arg Pro Ser Ser Met Tyr Phe
945                 950                 955                 960

Gln Thr His Asp Gln Ile Gly Met Ile Ser Ala Gly Pro Ser His Val
                965                 970                 975

Ala Ala Met Asn Ile Pro Ile Pro Phe Asn Leu Val Met Pro Pro Met
                980                 985                 990

Pro Pro Pro Gly Tyr Phe Gly Gln Ala Asn Gly Pro Ala Ala Gly Arg
```

-continued

```
              995                 1000                1005
Gly Thr Pro Lys Gly Lys Thr Gly Arg Gly Gly Arg Gln Lys Asn Arg
    1010                1015                1020

Phe Gly Leu Pro Gly Pro Ser Gln Thr Asn Leu Pro Asn Ser Gln Ala
1025                1030                1035                 104

Ser Gln Asp Val Ala Ser Gln Pro Phe Ser Gln Gly Ala Leu Thr Gln
                1045                1050                1055

Gly Tyr Ile Ser Met Ser Gln Pro Ser Gln Met Ser Gln Pro Gly Leu
                1060                1065                1070

Ser Gln Pro Glu Leu Ser Gln Asp Ser Tyr Leu Gly Asp Glu Phe Lys
            1075                1080                1085

Ser Gln Ile Asp Val Ala Leu Ser Gln Asp Ser Thr Tyr Gln Gly Glu
            1090                1095                1100

Arg Ala Tyr Gln His Gly Gly Val Thr Gly Leu Ser Gln Tyr
1105                1110                1115
```

(2) INFORMATION FOR SEQ ID NO:3:

(i) SEQUENCE CHARACTERISTICS:
  (A) LENGTH: 13146 base pairs
  (B) TYPE: nucleic acid
  (C) STRANDEDNESS: single
  (D) TOPOLOGY: linear (ii) MOLECULE TYPE: genomic DNA (xi) SEQUENCE DESCRIPTION: SEQ ID NO:3:

```
ATGGCATACT GAGTGGCCCT TGTTGCCAGC CAGCATTGAC TCTTTAATCC TTTTGCTCAG    60

TAGAGGAGCA CGGGATTCAG TAGCATAGAC CTCAGGAGTG GGGCCTCTGG GTGCCCTTGG   120

TGGCCTGCAC TGGTGATACT GTGTTCTCTC TAGGTTGGAC CAGAGGGCAT CTTGCAAAAT   180

GGGGCTGTGG ATGACAGTGT GGCCAAGACC AGCCAGCTGC TAGCTGAGCT GAACTTCGAG   240

GAAGATGAAG AGGACACATA CTACACTAAG GACCTCCCAG TCCACGCCTG CAGGTATGCT   300

GCAGGGCTCC AGGACCAAGA GGTGGCCTGC TTCAGAGTAC CGGTTCCTTG TTCAGAACCC   360

AGAGCACAGT ACCTAACACC CCAGATTCAT AGGGTTCTTG TGGGTCCCCT GCCATAGCCA   420

CTCAAGCAAG GACCCCTGAA GGAGCCAAGG CAGGGCATGG ATCCTGACTA AATCAGCTCC   480

ATCAGGGCCA CATGAGGGCA CTGGAGGCTT AAAGAGTTGG AATGTCCTTG TTGTGGAATA   540

CCCAGCTCAG CTAACTTCAC ACCCACCCAC CCACACACAC ACCCAGCAAG GCCAGAGCTT   600

GTCTTTACTA GGGTTTTGTA GCCATCTGCC GCCCTCTACA GGGCTGTTTT GGCCTCTCCT   660

CTCCACACCT ATTGCTTTCC GTTATAATGG CTCTCTCCTG GTTGACAAGT GTTTTCTTTT   720

TCTTTTTTTT TTTTTTTTAA AGATTTATTT ATTTATTATA TGTAAGTACA CTGTAGCTGT   780

CTTCAGACAC ACCAGAAGAG GGAGTCAGAT CTCGTGATCA GATGGTTGTG AGCCACCATG   840

TGGTTGCTGG GATTTGAACT CCTGACCTTC GGAAGAGCAG TTGGGTGCTC TTACCCACTG   900

AGCCATCTCA CCAGCCCGAC AAGTGTTTTC GAGGATAAAA CCAGAGCTAC AGGCAGGCTG   960

ATCTGGGAGC CCTAGTCGTC CTTTCCACCA GGAATAGACG AGAGAGCCCA GTGAGAGCGT  1020

TTTCTGGTTT GACACCTCAT GGCCCCAGCC TGCCGGTGCA CAACAGAGCT ATGGAGACCC  1080

AGTGATTCAG GGGCCTCCCT TAGCCTGGGT TGGGCCTGAG CATTCTCTGG TTGCAGAGTA  1140

CCTGCCTTCT GGAGTCAGGT GCTCCCACAA CCTTGTTAGA AACTTGCAGG CTGAAGGGAA  1200

GGGGCCAGGA TTGCCTTGGG CCTGTGCCAC TCAGGCATCT GTGTTGCCCT CACACTAACC  1260

AAACCTGAAA GCTGCAGGCC AGTACTGACT GTTGATGTTT GGGCTTTTCC AGTTACTGTG  1320
```

```
GAATCCATGA TCCTGCCTGC GTGGTTTACT GTAATACCAG CAAGAAGTGG TTCTGCAATG  1380

GCCGAGGAAA TACTTCTGGC AGGTAGCTGA CAGCCATGCA TGTGTGTTTA ATCAGCAACA  1440

CTAGGGCTGC TGTGAGTTAC GGTGTTGTTG GAGCAAAGCT GGAATGAGAT GGTGCTGGTG  1500

AACCTGGGCT CCCCCTTTGA CTGGTGTAAC TTGAAACAGA TGGTGGCGTG TGAACGCTTC  1560

GACATGTTTA TCCTTGATTG ATTCTCTGCC TCGCTCATTA TGTGAGGAGT TTGGCTTAAT  1620

TCTGTTCTCA GGCTGTGCCT GCCTCTCATG AAATGAGGCT GGCATGGCCT GCCTGTCCTT  1680

GTTCCTGGGA GGTTGAGGGC ATCCAGCTGA GCCAGTTGAC TTGATTGTCT CTGGAACCAA  1740

TGGTTCAAGA TCCTAAGTCA TTAGGAACAA CTAGACTCAT CCCTATATCA TGCTGGCTCT  1800

CCATGCAAGT GTCAGGAAAC ACTGTTGGAG AGAAACAACT GAGCCAGGTG TGCCTGTTTC  1860

CCACTGCCAC CAGGGGTGTG GCTTGTTTCT GAGGACATTC TGTAAAAAGA ATGCCACAGA  1920

AGGTTGTAGG TACCAGGTCT ACAGTGAGGC AGGGATTATC ATCTTTAAAA GATCTTAAAG  1980

TCACTTTCAG GGACCAAGAC ATCCCATTCT CAGAAGGAGG AGTAAGACCT ACAAAGCTAA  2040

GAATGGCTGG ATGGTCACTA CAGTGGGGGT TTCATGGGAT CATACAGAAA GACAACTAAG  2100

ACAGTCAGGA AGAACTGGCA GAGCCTGTGG GCCCTGAGGT GGCCAGCCAA TGTGGGCCAC  2160

TATTGGGGTA GGCCATGTCC TCATATGTGA CGGGGAAGGG ATGGGAGCTA TGGTCCTTAG  2220

GGCAGCTCCT TGCTATAGAG ACCAGGAGGT GACCTGTTTG TTTAAATAGG CATGGAAAAA  2280

GAGGACCTGG AAGGAGCCAT TTTTTGCTGA GCATGGCTGC CAGAGGTTAA GTTAGCACCA  2340

TGTGCTGGGG CTAGAGAAAG AGGAAATGGA GGGGTTGTGT GAGTCAGTGA ACAAGCGAGC  2400

GGGGCTGAGG CTCCCTGGGC ACCTGTGCCC CTGAGGTGTG ACCATCTGGT CTGTGCTGAC  2460

AGACCATGAG CAGTACTGGA CATTTTGCAT GGGGTAGCCG ACCTGGAGGT GCCGAGAAGC  2520

CAAGCTTGGG GTGTTAACTG CGATGGTTTC CTGGTCTCAG CCACATTGTG AATCACCTCG  2580

TGAGGGCAAA ATGCAAGGAA GTGACGCTGC ACAAGGACGG GCCTCTGGGC GAGACCGTGC  2640

TGGAGTGCTA CAACTGTGGC TGCCGCAACG TCTTCCTGCT GGGCTTCATC CCTGCGAAGG  2700

CCGACTCTGT GGTGGTGCTG TTGTGCAGGT GAGCTGCCTG CAGCAGGGCT GGACTGGAGA  2760

GGACAATGTC TGCTGGGACC AAGTTCTGTG TGTATTCTGG TCAAATTAGA AAATGAAGTC  2820

TGGCCTGATG TGGTAGTGTA CACTTTTAAC TTCAGCCCTG GGGAGGCAAA GGCAGAAGTT  2880

TCTCTGAGTT CAAGGCCAGC CTGGTCTACA AAGAGAGGCC AAGGCCAGCC AGGGCTACCC  2940

AGTTAGAACC TGTCTGAAAA ACTGAAAGAA GGAAAGTGAC AGGTCTGCTG TGAACTGAGG  3000

CCAGAGCTGG GCGTGCAGAT GCTGCTGCTG CCTTCTGGCT AGTTTGAGGC CTCCTGGGCC  3060

AGGTCCCAAC CCTCTCTCCT GCCCCACACC TGCACAGGCA GCCCTGTGCC AGCCAGAGCA  3120

GCCTGAAGGA CATCAACTGG GACAGCTCAC AGTGGCAGCC CCTAATCCAG GACCGGTGCT  3180

TTCTGTCATG GCTGGTCAAG ATTCCCTCTG AGCAGGAGCA GCTGCGAGCA CGGCAGATCA  3240

CGGCACAGCA GATCAACAAG CTGGAAGAGC TCTGGAAGGT GAGCCACTCA TAGACAAAAG  3300

AAAAGTAACG TGGCAAGCCT CACACTGGGC AGGAGATATT GGGGGTGGGG GTGGGGACAT  3360

GACCTAGGGC TCTGCAGGGG ACATAGTGGA TGGTCTGAGT AATTGGGTTA GGCTGTTATG  3420

AGATTCCTAC TCCAAGGAGC ACCTGTCCTT ATCCCTAATG ACAAGTCAGG GTTCCAGATT  3480

AGGTTGGAGT TCTGTTCTGG CTAGCTTTAG ACTCTGACCT TGTTTTCCAA ATGTGACTAG  3540

GGGTGTCAGT TGAGCACCCT CTAACCAGGA ATCCCAAGTA GTATTGGATA GAAACCTTCT  3600

AAGCTTGTCC AGCTTAGTCT CTTTGCACTT GGGTGGTCAA GTTCCAGTTA TCTCAGTATG  3660
```

```
CCCAGGTTCT CTGTTCTCTG TCTCAGTGAG GCTCACAGAG GGCAGTTGGT CCCAGAGGAG  3720

GCATGTTGCT ACAGGATATG AGAGAGGGAC TTGGCTCACT GGGAGAATCA TGAGACTCTG  3780

ACAGCCGAAT CTGGGGCTCC AGATGGGCCT GAGTATTGTG CTGGGCCGTG GGGGTGCTGT  3840

TGCCAGGTTT ATTGGGGTTA GAATGGTGTT GAGTATGCCA GGGCCATCAG AACAGTAGGC  3900

TCAGCGCAGG CCCCGGCACA GTGGCCACTC TCCACCTACG AGGGTTTGTG CTGAGAGGCC  3960

TTGGCTTGCT TCTGAGCTCT TGATCACTGG CTGCCAGGAC GAACACAGCA CTATTCTTGG  4020

CCATAGGAAA ATCCTTCAGC CACTCTGGAG GACCTGGAGA AGCCAGGCGT AGACGAGGAG  4080

CCACAGCACG TGCTCCTGCG TTACGAGGAT GCTTACCAGT ACCAGAACAT CTTCGGGCCA  4140

CTGGTCAAGC TGGAGGCTGA CTATGACAAG AAGTTGAAGG AGTCACAGGT GATGTGGCAC  4200

AACAGACCAG GCCTCTAGCA AAACATCTCC CGAGTCAGGG GCTCTTCCTG GCCTTGAGCC  4260

TGGATGAAAC CAGGCATGCA GATGAGAAAA CCCTTGTGTC TGGTTCACAG CTTTGTCTGC  4320

AGCTCCAAGA ACATTTCTGG GATATGGGAC CCATGCCACC AATTCCCCAA AGTGCCTTCC  4380

CTCCCTACAG AGCCTGGCGT GTGGGGTCTC CTGAGGCTCT CTACAAAGCT TGCTGCTGGG  4440

ACTGGCTTAG GCAGTGGGTG TTGGGGGGTC CTGGTTGCTT CTTTCCCAGA TGCTGGAGTT  4500

CCTGGCCGTG GATGCTGTGC TCTGCACCCC AAAGGCAGCA CAGCACAGAC ATGGCCTTCC  4560

TAGAGGCTCT GACCTGTGGG AAGCCCAGCC CGTGAATGAG TGTGGGGCTA ACCCGGCCCA  4620

TGTTTCTCAT GTGTTCAGAC TCAAGATAAC ATCACGGTCA GGTGGGACCT GGGCCTTAAC  4680

AAGAAGAGAA TCGCCTTCTT CACTTTGCCC AAGACTGACT CTGGTAATGA GGATTTAGTC  4740

ATAATTTGGT TAAGAGGTGA TTTTAAGTTT TAAAATATTT GTGACCATAA GTAGAATAAA  4800

ATTCCTAGTC CCCCATATCA TGTCCCTTAT GTGAACTCTG CATGGTGGAG GCCACGCCCT  4860

CTTGAAAGTG CTAACTCTGC TACTCCTTCC TGCAAGACAT GCGGCTCATG CAGGGTGATG  4920

AGATCTGTCT GCGGTACAAA GGGGATCTGG CGCCCCTGTG GAAGGGGATT GGCCACGTCA  4980

TCAAGGTTCC TGATAGTATC CTTTGTCATA TCTGCTAGGA GGATGGGTTC TGTAACAGGA  5040

CCCCTGGCTG TCCCCAGGGC TTTAATATGT ACAACTTCTT CCTCTTAATA TACAATTTCT  5100

TCTCTCTTTC CACTTTGTGA GACATACACA CCGTGACATG GTAGTGAGTG CGCGTGCGAG  5160

CATGCACATG TGTGAGTGAA ACAGCCTGGA ATCTGTCTGC AGCAGTTCCT TTGCCTGATA  5220

GGCAAGGAGA GCTGGTCTAG TGATGAAGTC AGGGGCTCTG TAGAAGGTGA CTTTGAACAG  5280

GAAACTGACT TAACTCAGTT GCCAGATTAT GGTGATGAGA TTGCTATTGA GCTCCGCAGC  5340

AGCGTGGGTG CCCCTGTGGA AGTGACCCAC AACTTCCAAG TGGATTTTGT GTGGAAGTCA  5400

ACCTCTTTTG ATAGGTTTGT GAGGGCCATA CCCTTGGGGG CCACCTCCAC CTTTGGTACC  5460

TGTGGCTCGT GTGGGTTTTA CACTGGCTGT TTTTATAGGA TGCAGAGTGC ACTGAAGACC  5520

TTCGCTGTGG ACGAGACCTC TGTGTCAGGG TATATTTACC ACAAGCTGCT GGGCCACGAG  5580

GTGGAGGATG TGGTCATCAA GTGCCAGCTG CCAAAGCGCT TCACAGCTCA GGGGCTCCCT  5640

GACCTCAACC ACTCTCAGGT GCCATTAGGC CCCTAGGGCC AGGGTCTGTA GGGGCTGTGC  5700

CTTTGCAGCT TTGCTGATGC TCCGTCCTTG CAGGTGTATG CTGTGAAGAC CGTGCTGCAG  5760

AGACCACTCA GCCTCATCCA GGGCCCTCCA GGCACAGGCA AGACTGTGAC ATCAGCCACT  5820

ATTGTCTACC ACCTTGCTCG GCAGGGCAAT GGGTAGGTAG TAGCAAGAGC CTTGTGGGTG  5880

GGAGGTAGTA ATGTCTTGTG TGGCCTTGTG GTCTGTTATA GCTCTGCCGG GGCCACACAG  5940

AAAATATATA CAGCGTTACA ATACAGGCAC CTTTTGTGTT CTACAACCCT CTGGCCTGCC  6000

TCATGTGGAT GACAGGGTGA GGTCACCGTT GAGCTGATGG TGGCTAGGCA GGTGACAGGA  6060
```

```
GGCTTTGCTT GTTTTGCCTT GGCTGTGCAG CTTTTCCCTG GGCCTTGCTG AGCTGCTCTG    6120

GGTGATGCTG ACAGCCTATT CCACTCTCTG CAGGCCTGTA CTGGTTTGTG CTCCAAGTAA    6180

CATCGCTGTG GACCAGCTCA CAGAGAAGAT CCACCAGACA GGACTGAAGG TCGTACGCCT    6240

CTGTGCCAAG AGCCGTGAGG CCATTGACTC CCCAGTGTCC TTCCTGGCTT TGCACAACCA    6300

GATCAGGAAC ATGGACAGGT GAGTATCTCC AGCTTCGGGC TCAGTACAGG CTGCGCCCTG    6360

CTGCTGGCGC TGACTCCCAC CACATTTTCT GTAGCATGCC TGAGCTGCAG AAGCTGCAGC    6420

AGCTAAAGGA TGAGACAGGC GAGCTGTCAT CTGCAGATGA GAAGCGGTAC CGGGCGCTTA    6480

AGCGCACAGC TGAGAGAGAA CTTCTCATGG TGAGCTCAGT GCCAGCCCAG GAGCCTTTGG    6540

GCTGTTCCTT GTGGGCAGAG GATCTGGAGA GACTTGTCTG TTCGAGTCAG AAGCCTGGTA    6600

GCATGTCTGT ACCTTTGCTT TTGAAGACTT GGAGGGACCT CATCTTCCTG ATCTGTGCCA    6660

TAGTCAGGAA CATAGCTGCC ACTCCTGTCA GTCTCCAGTC TAACAAACCA GTCCATCAAA    6720

GCTGGAGTCT CAGCCTTGGG GTAGTACCAC CAGCTCAGTA CTGTCCCAGA GATTATTGGC    6780

AGACACAGCT GTGTCAATGC TGGGGAGTGT GCTCCAGAAG CTGTACCAT TTGAAAGTTG    6840

ACGCTCATGG TCCCTGGGAT GTTCACACTT GGGCTGCAGG AGAAGTGGCT AGTTTACTTG    6900

TTGGGGAATT GTCTGTGGAG AGCCAGTCTG GGGCAACACA GTAAGACCCT GTCAGAACAA    6960

CTTGTGCGGG CGCACTTCAA GAGTGCTGGG TGGGTGTAGA ACAGGGTATT CCAGGTCCCA    7020

CCCTAAGCCA TCTAGCTGTG GTGAGGTAGG CACATGTGCC CTGATGTCTG TGCCTTCCCC    7080

AGAATGCAGA TGTCATATGC TGCACATGTG TGGGTGCTGG TGACCCGAGG CTGGCCAAGA    7140

TGCAGTTCCG TTCCATCCTC ATTGACGAGA GCACCCAGGC CACTGAGCCT GAGTGCATGG    7200

TGCCTGTAGT CCTTGGGGCC AAGCAGGTGG GTACCTGTCA CTCATGTGGC CCTTGATAGT    7260

GGTGCTGGGT GACACAAGAC CTGCTAGAGG TCTTTGAAGG GGGCTGAGTC CCATGTGTTC    7320

CACAGGCCCG CGCCTCCTGG GGTGTTGGCA GCCTGTACTG AGCAGCTCCC CCTACCCCCC    7380

TGGGGTACTC GTTCTGTTGC TTTTAGATGG TGGAGGTGAC CCCTGTCCCT GTGGTAGGCA    7440

CTTAGGAACA TGGAGGGGTT AACTTGAGGG ACTTCTTGCT GCAGCTAATC CTCGTCGGTG    7500

ACCACTGCCA GCTGGGCCCA GTGGTGATGT GCAAGAAGGC AGCCAAGGCC GGACTGTCAC    7560

AATCGCTCTT CGAGCGCTTG GTGGTGCTGG GCATCCGGCC CATCCGCCTG CAGGTGCAAT    7620

ACCGCATGCA CCCTGCACTC AGCGCCTTTC CGTCCAACAT CTTCTACGAG GGCTCATTGC    7680

AGAATGGCGT CACTGCAGGT AACAGTTGCA GCACTGTGAA GGGCATAGGG AAGGGCCATG    7740

AGGACGCAAC CCAACTGTTA TACCCTATGC CCTTCATGGT GCTGCTCACC CCAGCTTCTC    7800

AGACACAGTG CTGCTGGAGT GTGTGGTGGC TCCACAGTGG TCGTCATACC TTTCACCATG    7860

GCCAGGTCAT GCACTGGCTC TGCTCCCATG GCTGTTGCTT TATGCTGAAC AGTCCCAGGC    7920

TAGGCACCCC ATGCTTAGAA ATGAACCAAC CACCCCGACA ACAGGAATTC CCAGCCTTTT    7980

CCTTGTGATG GTGGTTGGCT GAGATGTCAC CCTATCACAA GTTTAAGTGA GACCAGGCAG    8040

GTAGATTATG AGAGCTTGTC TTCTGAGGTC AGCAGCTGAT GACACCTCTT ACCTGCAGCA    8100

ATTTGAGGCT CTGTGAACAG GGAATTTAAG GACACTAGGG TCACCTTTGA ATGTAGTTCT    8160

GGCCCTGTCC TAAGAGTATT TATGGCAGTG ACCTCTTCAG GGTCTTTGCA CTGTATCTGT    8220

TGGTACAACC TAGAGGATCT GGAGCAGTAG ACAGAGTGAC ACTGTGGTGT CAAGTGAGCC    8280

ATAAGTATAC TGTCACACAC CCTTGAAAGC TATTTGCTTT CATGGGAGGT TGGTACAGAA    8340

ACCAACTGGG CCTTACTGTC CTCCACGAAG CCTGAGTGAA GTGGAATGAA AGGTTGCTAT    8400
```

```
CTGACTTGCT TTGCAACATA AATGTGTTTT TCACCAAACT GTTAAAACAT CTAGGCATGG   8460

CTCTCAGCTT TAATCCCAGG ACTTGTGAAG CAGACAGGCA GGCTCTCTGG GAGGTCAGGG   8520

CCATAGTGAA ACCCTCTCTC AAACACACAA ACACGGCTTC AGCACAGTGG CTTAGGCATG   8580

GATTTGAATG TCTGCCTTTG ATGAGCTGTG ACGGGAAGG AGCCTGCTCA GAGCTGCTGT    8640

GTCTATGTGG CCTCCCATGT GGATCCAGGC AGCCATATTT GGGGACACCA CCTCTCTGCT   8700

GGCTAGGTCC TGCCATGATC TTCTCTTCCC TATGTGATTG TCCGAGTGTG GGAGGCTCTT   8760

GGGTGTTTCC TGGGCTCTGC TGCACTTGGT CACCACTCAG CACAGGAAGT GTCCTCGTGT   8820

ACTCAGTAGG CAGCCATGTC TTGAATAGTG TTGACCCAGG CCCTTGGCTG CCCACAGTGT   8880

GGTTGTACTT GATTGAGCCC CTGAGCTTCT CAGTGGGTGA CACCTTCTGT CTTTCCTTAT   8940

CAGCGGATCG TGTCAAAAAA GGCTTTGACT TCCAGTGGCC ACAACCTGAC AAGCCTATGT   9000

TCTTCTACGT GACGCAGGGC CAGGAGGAGA TTGCCAGCTC TGGCACATCC TACCTCAACA   9060

GGTGTGCAGC TGCGTCTCTG GTATGGAGCC ATTCTCACTC ACCCTCGGCT CCAACCCGAG   9120

ACCCACAGCA TCTTACTCCT TGGGTTGCTC TGCTTGTTAA CAGCATGTGA GGGAAGACGC   9180

AAACAGGCTC TTGTTTCTCC TGGGGCCTCA AAATGACAGG GGCGGGCAAC TATCATGTGG   9240

CCTCCTGTAA CCCCTTTGGT TACTGGAGGT CTGCCAGGCT GGGGAACCTG TGAGGAGCCT   9300

TTTCACTGAC AGCCAGATGT TCTCAGGACG GAGGCAGCCA ATGTGGAGAA GATAACTACG   9360

AAGCTGTTGA AGGCAGGTGC AAAGCCTGAC CAGATCGGCA TCATCACCCC CTACGAGGGC   9420

CAGCGCTCTT ACTTGGTGCA GTACATGCAG TTCAGCGGCT CCCTGCACAC AAAGCTCTAC   9480

CAGGTACCCC ATACCCAGCA GTTAGGAGAG AGCGCATGAG CACACGTCAT GACACACAGG   9540

TCAGCCTTGG GCTACTGACC TGGCTGGAGG CAAAAGTAGA AAGAGTGTGG TGCTGTGTCA   9600

GCACTTCAGT GACATGACCA GGTGGGTCTT CATGAATTTG AGGTGGTCAG CCTTGATTGA   9660

GAGCTTCAAG GCAGCCAGGG CTGTTCAGTA AGGCTTTGTC TCAAAGAAAG AGCAGCCCAC   9720

GGCTAGACAG GAAGGGGCAG GACAGCTGGG CCCACCTGAG GGCATGGTA CTTGTGACAG    9780

ATGCAGAGCT GTGGTTGGTT ATACCATGGA GCCTACTCAG CATTTGCTTC ATTGGGCCTG   9840

TGGTATCTCT ATTATTGGGG ACTCTTGTAG CATCTGGCTA TAATGATGCA GCTAAAGGAA   9900

GAGACAGGAG AACGAGGGGC CGGGATATGG CTGACAGGAC ACTTGTCTCA TTCAGGAAGT   9960

GGAGATTGCC AGTGTGGACG CCTTCCAGGG CCGGGAGAAG GACTTCATCA TTCTGTCCTG  10020

CGTGCGCGCC AATGAACATC AGGGCATTGG GTTCCTAAAC GACCCCCGGC GTCTGAATGT  10080

GGCTCTCACC AGAGCAAGGT AGGCCGCTGC CCATCACTAC CATCCACCCT CCAGCCAAAA  10140

CAAGAAGCCC CCCCCCCTGT GATTCATTTT ACTCATATCT GTCCTGGGAG TACATGTGCA  10200

TGCTGGCACC CCATCTTGAG AACTGGGCAC TATGGCCTAC CTGCTGCCTT ACTGCTTCAA  10260

GAACTCAACT ACAAGATCCT ATAGGACACA GATTTAGCTC ATGATCAAGA GAGGCATTTA  10320

GAGAGCTGCG AATCACACCC AGAGCTCTCA CTGCTGCTTA AGTGCTACCT CATGTCTTAG  10380

CATCCTGCTC TTCACATTCA AGGTGCTAAC CCTAGACAGT GGAGTTCAGT AGGTGTGGCC  10440

ATGGGCTCAG CATTTTGATT GCCCTGCAGA TATGCGTGA TCATTGTGGG TAACCCAAAG    10500

GCCCTGTCGA AGCAGCCCCT GTGGAATCAC CTGCTGAGCT ACTACAAGGA ACAGAAGGCG  10560

CTAGTGGAAG GGCCGCTCAA CAACCTACGT GAGAGCCTCA TGCAGTTCAG CAAGCCTCGC  10620

AAACTTGTCA ACACTGTCAA CCCGGTGGGC CTAGGGGCTG GCCTGGGACC TGGGAAAGCT  10680

GGGAGCTCTT AGCCTCTGCT GCTGTTGACT GACACATTCC TCACTCTTAT GCCACCCTGC  10740

AGGGTGCCCG CTTCATGACT ACTGCCATGT ACGATGCCCG TGAGGCCATC ATCCCCGGGT  10800
```

```
CTGTCTATGA CCGCAGCAGC CAGGGTGAGT CTTCCTGGCC AGAACCCATG TGTTTATCTT    10860

CCCACGTCCC ACTCCGAACC TGTTGCCCCA TGGGTGGCCT CCGTCTGGAA CTTGTCCAGT    10920

AGCTTCTGTA GCTTCTCCAA CCAGGTCCCC AAGAGCTGTT CTGGCCTCAG CTAGTGGTTT    10980

GGGCCATGAT CCCTTTAGAA CTGCTAAGGC CACCTGTCTG CCTGAGTGCT GCTGCCCTTG    11040

TATCCTGCAA CAAACCCGTG TCTACCTCAG CTAGGCTGGC CTCTGCTTTC TGGAAGCTTC    11100

CAAGTTTGTC TAGAAAGTTC CATCGTGGCC AGATCTCACC AACCCTTCTG CCATTTCTTA    11160

CCCTCTACCA GCACTCTGCA TGTCAAGACA CACTCGACCT CCCGACTTGT CTGGCTGGCC    11220

CAGCAGCTAG TTCATGGCAG CCAGTGTCCA CTGGAGCCCT GCATCTGACT CAAATGTTTT    11280

GCAGGCCGGC CCTCGAACAT GTACTTCCAG ACCCATGACC AGATCAGTAT GATCAGCGCA    11340

GGCCCCAGCC ACGTGGCTGC CATGAACATC CCTATTCCCT TCAACTTGGT CATGCCTCCC    11400

ATGCCGCCAC CTGGCTACTT CGGACAGGCC AACGGGCCGG CAGCTGGTAA GCGGTTTTAT    11460

CTCTACTGCC CAGGCTCTCC TCCTAGCTTT AGGTAGACCT TGCCATATTT CACTGCTGTC    11520

TTTCAGGTCG GGCACCCCA AAAACCAAGA CTGGCCGTGG GGGCCGCCAG AAGAACCGCT    11580

TTGGGCTTCC TGGGCCCAGC CAGACCACCC TTCCCAACAG CCAGGCCAGC CAGGACGTGG    11640

CCTCCCAGCC CTTTTCACAG GGTGCCCTCA CACAGGGTTA CGTGTCCATG AGCCAGCCCT    11700

CTCAGATGAG CCAGCCTGGC CTCTCCCAGC CAGAACTGTC CCAGGTGGGC TGCATCCTAC    11760

AGCAGAGAAA AGGGGTGGA GGGGTGAGGG GACACATGAG ACCATGATGC TGCCTTTCTG    11820

AAGGGTGAAT GAACTCTACT GCTATGGATC TGAACCTGTC ACCCTGCTAC TCTGGCTGCA    11880

GTATGGGGTT TCTTCCCATC CTCGGGTCTG CGGACTGGGT GGCTGTGGGC TACTAGCTTT    11940

CCTGGCCATG TTCACACTAC TTTTGCCTTT CAGGACAGCT ACCTCGGTGA TGAGTTTAAA    12000

TCACAGATTG ACGTGGCACT CTCACAAGAC TCCACATACC AGGGAGAGCG GCATACCAG    12060

CACGGCGGGG TCACCGGGCT GTCCCAGTAC TAGAAGGCAA GTGCCCTGGT GGGTTCAGCT    12120

CTCTGCACAC GTGTGCAAAC AGGGTCTTCC CAGACAGACT GGGCAAGTAG ATATGGTGTG    12180

TTGGCAGGTC CTGCCTCTAC TGGCCCTGAC ACCTCTAACC CTGTCCCTGA TCACAGGTAG    12240

CGGAGGAAGA GCTAAGCTAT GTGGCTTAGT CTATCAGCAT CTTATTCTGG GTAATAAAAA    12300

ATAAAAATAA ATGGATACCT GTTTTCCACT GCTAAAACTG AAGCACCACT GTGTGAGCAG    12360

CCGAGGAGAG GAGAGGAAAG AGGAGCGAGA GCGAGCAGAG AGCGGCCAGG GAGGACGACA    12420

GAGCGGAGCG CCGAGGAGCG GGCGCCCCCT GTGGGCGGCG AGAGGAGAGA GGCCCGCACC    12480

GCTGCGAGGC CGGCCCAGCG CCGTGCCCGC CAGAGGGAGA GGCCTCGCCA GGACCGGCCC    12540

CGCTGGTCTT TTTCTTTGTT TCTCGTGATT GAGGGGCTAC GTTTTAGCAG GACGAACTTC    12600

GCGTTTCTGT GCCCAAGCGG GCGGCCAGGA GCATCAGTGC GCGGTCCCAG CGCTAAGGGG    12660

TTTCATTTAA AGAAAATACG GTGTTTGGGG TTTTTCTGGT TTTCCTTTTT TTTTCTTTT    12720

TTTTGGTTTT TTTTTTGTTT GTTTGGTTTT TTTTTTTTTT TTTTTTTTTC TTTTTGGTTT    12780

TCCTTTCCTC CCCCCTACCC CCTTCAAAGA TTCTTTCAAA GGAGTATGGG AAGTACTTGG    12840

ATCGGTTTGT CTCTAGAGAC CTGACTGTTA AACCTGAGAG ATGCGAGAAG CTTCCGGGAA    12900

AGGCAGCGCT GAGAAGCCTG AGCCCCGCAG CCTGGGATCA CCGCCTGCAC CACAGCCGGA    12960

GGATTTGTTT TGGAGTTTGA GCTTCAGAGG CCACAGGCGA ATCGTGAGCA CGGCCTGCGG    13020

GTTCTTCCCC ATCGAGGGGT GGAGGCCTCA TTGTTTGGGC GCCCTGCCCC GGACCCCACC    13080

TCCCCGCGGA GCCACCCAAC CCTACCCAGG AAACCTGGCC AACGAAATGG AATTTAATTT    13140
```

-continued

TAGCAA                                                                    13146

(2) INFORMATION FOR SEQ ID NO:4:

(i) SEQUENCE CHARACTERISTICS:
        (A) LENGTH: 1043 amino acids
        (B) TYPE: amino acid
        (D) TOPOLOGY: linear (ii) MOLECULE TYPE: protein (xi) SEQUENCE DESCRIPTION: SEQ ID NO:4:

Val Gly Pro Glu Gly Ile Leu Gln Asn Gly Ala Val Asp Asp Ser Val
  1               5                  10                  15

Ala Lys Thr Ser Gln Leu Leu Ala Glu Leu Asn Phe Glu Glu Asp Glu
             20                  25                  30

Glu Asp Thr Tyr Tyr Thr Lys Asp Leu Pro Val His Ala Cys Ser Tyr
         35                  40                  45

Cys Gly Ile His Asp Pro Ala Cys Val Val Tyr Cys Asn Thr Ser Lys
     50                  55                  60

Lys Trp Phe Cys Asn Gly Arg Gly Asn Thr Ser Gly Ser His Ile Val
 65                  70                  75                  80

Asn His Leu Val Arg Ala Lys Cys Lys Glu Val Thr Leu His Lys Asp
                 85                  90                  95

Gly Pro Leu Gly Glu Thr Val Leu Glu Cys Tyr Asn Cys Gly Cys Arg
            100                 105                 110

Asn Val Phe Leu Leu Gly Phe Ile Pro Ala Lys Ala Asp Ser Val Val
        115                 120                 125

Val Leu Leu Cys Arg Gln Pro Cys Ala Ser Gln Ser Ser Leu Lys Asp
130                 135                 140

Ile Asn Trp Asp Ser Ser Gln Trp Gln Pro Leu Ile Gln Asp Arg Cys
145                 150                 155                 160

Phe Leu Ser Trp Leu Val Lys Ile Pro Ser Glu Gln Glu Gln Leu Arg
                165                 170                 175

Ala Arg Gln Ile Thr Ala Gln Gln Ile Asn Lys Leu Glu Glu Leu Trp
            180                 185                 190

Lys Glu Asn Pro Ser Ala Thr Leu Glu Asp Leu Glu Lys Pro Gly Val
        195                 200                 205

Asp Glu Glu Pro Gln His Val Leu Leu Arg Tyr Glu Asp Ala Tyr Gln
210                 215                 220

Tyr Gln Asn Ile Phe Gly Pro Leu Val Lys Leu Glu Ala Asp Tyr Asp
225                 230                 235                 240

Lys Lys Leu Lys Glu Ser Gln Thr Gln Asp Asn Ile Thr Val Arg Trp
                245                 250                 255

Asp Leu Gly Leu Asn Lys Lys Arg Ile Ala Phe Phe Thr Leu Pro Lys
            260                 265                 270

Thr Asp Ser Asp Met Arg Leu Met Gln Gly Asp Glu Ile Cys Leu Arg
        275                 280                 285

Tyr Lys Gly Asp Leu Ala Pro Leu Trp Lys Gly Ile Gly His Val Ile
290                 295                 300

Lys Val Pro Asp Asn Tyr Gly Asp Glu Ile Ala Ile Glu Leu Arg Ser
305                 310                 315                 320

Ser Val Gly Ala Pro Val Glu Val Thr His Asn Phe Gln Val Asp Phe
                325                 330                 335

Val Trp Lys Ser Thr Ser Phe Asp Arg Met Gln Ser Ala Leu Lys Thr
            340                 345                 350

```
Phe Ala Val Asp Glu Thr Ser Val Ser Gly Tyr Ile Tyr His Lys Leu
        355                 360                 365
Leu Gly His Glu Val Glu Asp Val Val Ile Lys Cys Gln Leu Pro Lys
        370                 375                 380
Arg Phe Thr Ala Gln Gly Leu Pro Asp Leu Asn His Ser Gln Val Tyr
385                 390                 395                 400
Ala Val Lys Thr Val Leu Gln Arg Pro Leu Ser Leu Ile Gln Gly Pro
                405                 410                 415
Pro Gly Thr Gly Lys Thr Val Thr Ser Ala Thr Ile Val Tyr His Leu
                420                 425                 430
Ala Arg Gln Gly Asn Gly Pro Val Leu Val Cys Ala Pro Ser Asn Ile
        435                 440                 445
Ala Val Asp Gln Leu Thr Glu Lys Ile His Gln Thr Gly Leu Lys Val
        450                 455                 460
Val Arg Leu Cys Ala Lys Ser Arg Glu Ala Ile Asp Ser Pro Val Ser
465                 470                 475                 480
Phe Leu Ala Leu His Asn Gln Ile Arg Asn Met Asp Ser Met Pro Glu
                485                 490                 495
Leu Gln Lys Leu Gln Gln Leu Lys Asp Glu Thr Gly Glu Leu Ser Ser
                500                 505                 510
Ala Asp Glu Lys Arg Tyr Arg Ala Leu Lys Arg Thr Ala Glu Arg Glu
        515                 520                 525
Leu Leu Met Asn Ala Asp Val Ile Cys Cys Thr Cys Val Gly Ala Gly
        530                 535                 540
Asp Pro Arg Leu Ala Lys Met Gln Phe Arg Ser Ile Leu Ile Asp Glu
545                 550                 555                 560
Ser Thr Gln Ala Thr Glu Pro Glu Cys Met Val Pro Val Val Leu Gly
                565                 570                 575
Ala Lys Gln Leu Ile Leu Val Gly Asp His Cys Gln Leu Gly Pro Val
                580                 585                 590
Val Met Cys Lys Lys Ala Ala Lys Ala Gly Leu Ser Gln Ser Leu Phe
        595                 600                 605
Glu Arg Leu Val Val Leu Gly Ile Arg Pro Ile Arg Leu Gln Val Gln
        610                 615                 620
Tyr Arg Met His Pro Ala Leu Ser Ala Phe Pro Ser Asn Ile Phe Tyr
625                 630                 635                 640
Glu Gly Ser Leu Gln Asn Gly Val Thr Ala Ala Asp Arg Val Lys Lys
                645                 650                 655
Gly Phe Asp Phe Gln Trp Pro Gln Pro Asp Lys Pro Met Phe Phe Tyr
                660                 665                 670
Val Thr Gln Gly Gln Glu Glu Ile Ala Ser Ser Gly Thr Ser Tyr Leu
        675                 680                 685
Asn Arg Thr Glu Ala Ala Asn Val Glu Lys Ile Thr Thr Lys Leu Leu
        690                 695                 700
Lys Ala Gly Ala Lys Pro Asp Gln Ile Gly Ile Ile Thr Pro Tyr Glu
705                 710                 715                 720
Gly Gln Arg Ser Tyr Leu Val Gln Tyr Met Gln Phe Ser Gly Ser Leu
                725                 730                 735
His Thr Lys Leu Tyr Gln Glu Val Glu Ile Ala Ser Val Asp Ala Phe
                740                 745                 750
Gln Gly Arg Glu Lys Asp Phe Ile Ile Leu Ser Cys Val Arg Ala Asn
        755                 760                 765
```

-continued

Glu His Gln Gly Ile Gly Phe Leu Asn Asp Pro Arg Arg Leu Asn Val
    770             775                 780

Ala Leu Thr Arg Ala Arg Tyr Gly Val Ile Val Gly Asn Pro Lys
785             790                 795                 800

Ala Leu Ser Lys Gln Pro Leu Trp Asn His Leu Leu Ser Tyr Tyr Lys
                805                 810                 815

Glu Gln Lys Ala Leu Val Glu Gly Pro Leu Asn Asn Leu Arg Glu Ser
            820                 825                 830

Leu Met Gln Phe Ser Lys Pro Arg Lys Leu Val Asn Thr Val Asn Pro
        835                 840                 845

Val Gly Gly Ala Arg Phe Met Thr Thr Ala Met Tyr Asp Ala Arg Glu
    850                 855                 860

Ala Ile Ile Pro Gly Ser Val Tyr Asp Arg Ser Gln Gly Arg Pro
865                 870                 875                 880

Ser Asn Met Tyr Phe Gln Thr His Asp Gln Ile Ser Met Ile Ser Ala
                885                 890                 895

Gly Pro Ser His Val Ala Ala Met Asn Ile Pro Ile Pro Phe Asn Leu
                900                 905                 910

Val Met Pro Pro Met Pro Pro Pro Gly Tyr Phe Gly Gln Ala Asn Gly
            915                 920                 925

Pro Ala Ala Gly Arg Gly Thr Pro Lys Thr Lys Thr Gly Arg Gly Gly
930                 935                 940

Arg Gln Lys Asn Arg Phe Gly Leu Pro Gly Pro Ser Gln Thr Thr Leu
945                 950                 955                 960

Pro Asn Ser Gln Ala Ser Gln Asp Val Ala Ser Gln Pro Phe Ser Gln
                965                 970                 975

Gly Ala Leu Thr Gln Gly Tyr Val Ser Met Ser Gln Pro Ser Gln Met
            980                 985                 990

Ser Gln Pro Gly Leu Ser Gln Pro Glu Leu Ser Gln Asp Ser Tyr Leu
        995                 1000                1005

Gly Asp Glu Phe Lys Ser Gln Ile Asp Val Ala Leu Ser Gln Asp Ser
    1010                1015                1020

Thr Tyr Gln Gly Glu Arg Ala Tyr Gln His Gly Gly Val Thr Gly Leu
1025                1030                1035                1040

Ser Gln Tyr (2) INFORMATION FOR SEQ ID NO:5:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:5:

Gln Val Asp Phe Val Gln Lys Ser Thr Ser Phe Asp Arg Met Gln Ser
 1               5                  10                  15

Ala Leu Lys Thr Phe Ala Val
            20

(2) INFORMATION FOR SEQ ID NO:6:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:6:

Leu Ser Leu Ile Gln Gly Pro Pro Gly Thr Gly Lys Thr Val Thr Ser
  1               5                  10                  15

Ala Thr Ile Val Tyr His Leu Ala Arg Gln Asp Asn
             20                  25

(2) INFORMATION FOR SEQ ID NO:7:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (xi) SEQUENCE DESCRIPTION: SEQ ID NO:7:

His Ile Val Asn His Leu Val Arg Ala Lys Cys Lys Glu Val Thr Leu
  1               5                  10                  15

His Lys Asp Gly Pro
             20

(2) INFORMATION FOR SEQ ID NO:8:

(i) SEQUENCE CHARACTERISTICS:
            (A) LENGTH: 27 amino acids
            (B) TYPE: amino acid
            (D) TOPOLOGY: linear (ii) MOLECULE TYPE: peptide (xi) SEQUENCE DESCRIPTION: SEQ ID NO:8:

Ala Gly Gln Leu Asp Ala Gln Val Gly Pro Glu Gly Ile Leu Gln Asn
  1               5                  10                  15

Gly Ala Val Asp Phe Asp Ser Val Ala Lys Thr
             20                  25

(2) INFORMATION FOR SEQ ID NO:9:

(i) SEQUENCE CHARACTERISTICS:
            (A) LENGTH: 30 amino acids
            (B) TYPE: amino acid
            (D) TOPOLOGY: linear (ii) MOLECULE TYPE: peptide (xi) SEQUENCE DESCRIPTION: SEQ ID NO:9:

Ile Leu Ile Asp Glu Ser Thr Gln Ala Thr Glu Pro Glu Cys Met Val
  1               5                  10                  15

Pro Val Val Leu Gly Ala Lys Gln Leu Ile Leu Val Gly Asp
             20                  25                  30

(2) INFORMATION FOR SEQ ID NO:10:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (xi) SEQUENCE DESCRIPTION: SEQ ID NO:10:

Ser Met Ser Gln Pro Ser Gln Met Ser Gln Pro Gly Leu Ser Gln Pro
  1               5                  10                  15

```
Glu Leu Ser Gln
         20

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:11:

CTTTGACAGG ATGCAGAGCG C                                             21

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:12:

GGCACCATGA                                                          10

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:13:

GCCRCCATGG                                                          10

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:14:

Gly Xaa Xaa Xaa Xaa Gly Lys Ser
 1               5

(2) INFORMATION FOR SEQ ID NO:15:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:15:

Asp Xaa Xaa Gly
 1

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (xi) SEQUENCE DESCRIPTION: SEQ ID NO:16:

GGATCCCATC AGGAAAGAAG                                                  20

(2) INFORMATION FOR SEQ ID NO:17:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:17:

GTCGACTGAA GCTGAAGGCG AACGG                                            25

(2) INFORMATION FOR SEQ ID NO:18:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:18:

GCGGCCGCGA AAGACTGAAC GGCCAAT                                          27

(2) INFORMATION FOR SEQ ID NO:19:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:19:

AAGCTTATCC AAAGTATATT GGACCGG                                          27

(2) INFORMATION FOR SEQ ID NO:20:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO:20:

ACGCGTCGAC CACGCCTGCA GTACTGTGGA ATAC                                  34

(2) INFORMATION FOR SEQ ID NO:21:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (xi) SEQUENCE DESCRIPTION: SEQ ID NO:21:

ATAAGAATGC GGCCGCGGCT GCTGAACGCA TGAGGCTCTC ACG                        43

(2) INFORMATION FOR SEQ ID NO:22:

(i) SEQUENCE CHARACTERISTICS:
            (A) LENGTH: 971 amino acids
            (B) TYPE: amino acid
            (D) TOPOLOGY: linear (ii) MOLECULE TYPE: protein (xi) SEQUENCE DESCRIPTION: SEQ ID NO:22:

```
Met Val Gly Ser Gly Ser His Thr Pro Tyr Asp Ile Ser Asn Ser Pro
 1               5                  10                  15

Ser Asp Val Asn Val Gln Pro Ala Thr Gln Leu Asn Ser Thr Leu Val
            20                  25                  30

Glu Asp Asp Asp Val Asp Asn Gln Leu Phe Glu Glu Ala Gln Val Thr
        35                  40                  45

Glu Thr Gly Phe Arg Ser Pro Ser Ala Ser Asp Asn Ser Cys Ala Tyr
    50                  55                  60

Cys Gly Ile Asp Ser Ala Lys Cys Val Ile Lys Cys Asn Ser Cys Lys
65                  70                  75                  80

Lys Trp Phe Cys Asn Thr Lys Asn Gly Thr Ser Ser His Ile Val
                85                  90                  95

Asn His Leu Val Leu Ser His His Asn Val Val Ser Leu His Pro Asp
                100                 105                 110

Ser Asp Leu Gly Asp Thr Val Leu Glu Cys Tyr Asn Cys Gly Arg Lys
            115                 120                 125

Asn Val Phe Leu Leu Gly Phe Val Ser Ala Lys Ser Glu Ala Val Val
        130                 135                 140

Val Leu Leu Cys Arg Ile Pro Cys Ala Gln Thr Lys Asn Ala Asn Trp
145                 150                 155                 160

Asp Thr Asp Gln Trp Gln Pro Leu Ile Glu Asp Arg Gln Leu Leu Ser
                165                 170                 175

Trp Val Ala Glu Gln Pro Thr Glu Glu Lys Leu Lys Ala Arg Leu
            180                 185                 190

Ile Thr Pro Ser Gln Ile Ser Lys Leu Glu Ala Lys Trp Arg Ser Asn
        195                 200                 205

Lys Asp Ala Thr Ile Asn Asp Ile Asp Ala Pro Glu Gln Glu Ala
    210                 215                 220

Ile Pro Pro Leu Leu Leu Arg Tyr Gln Asp Ala Tyr Glu Tyr Gln Arg
225                 230                 235                 240

Ser Tyr Gly Pro Leu Ile Lys Leu Glu Ala Asp Tyr Asp Lys Gln Leu
                245                 250                 255

Lys Glu Ser Gln Ala Leu Glu His Ile Ser Val Ser Trp Ser Leu Ala
            260                 265                 270

Leu Asn Asn Arg His Leu Ala Ser Phe Thr Leu Ser Thr Phe Glu Ser
        275                 280                 285

Asn Glu Leu Lys Val Ala Ile Gly Asp Glu Met Ile Leu Trp Tyr Ser
    290                 295                 300

Gly Met Gln His Pro Asp Trp Glu Gly Arg Gly Tyr Ile Val Arg Leu
305                 310                 315                 320

Pro Asn Ser Phe Gln Asp Thr Phe Thr Leu Glu Leu Lys Pro Ser Lys
                325                 330                 335

Thr Pro Pro Pro Thr His Leu Thr Thr Gly Phe Thr Ala Glu Phe Ile
            340                 345                 350

Trp Lys Gly Thr Ser Tyr Asp Arg Met Gln Asp Ala Leu Lys Lys Phe
        355                 360                 365

Ala Ile Asp Lys Lys Ser Ile Ser Gly Tyr Leu Tyr Tyr Lys Ile Leu
    370                 375                 380

Gly His Gln Val Val Asp Ile Ser Phe Asp Val Pro Leu Pro Lys Glu
385                 390                 395                 400
```

-continued

```
Phe Ser Ile Pro Asn Phe Ala Gln Leu Asn Ser Ser Gln Ser Asn Ala
                405                 410                 415
Val Ser His Val Leu Gln Arg Pro Leu Ser Leu Ile Gln Gly Pro Pro
            420                 425                 430
Gly Thr Gly Lys Thr Val Thr Ser Ala Thr Ile Val Tyr His Leu Ser
        435                 440                 445
Lys Ile His Lys Asp Arg Ile Leu Val Cys Ala Pro Ser Asn Val Ala
    450                 455                 460
Val Asp His Leu Ala Ala Lys Leu Arg Asp Leu Gly Leu Lys Val Val
465                 470                 475                 480
Arg Leu Thr Ala Lys Ser Arg Glu Asp Val Glu Ser Ser Val Ser Asn
                485                 490                 495
Leu Ala Leu His Asn Leu Val Gly Arg Gly Ala Lys Gly Glu Leu Lys
            500                 505                 510
Asn Leu Leu Lys Leu Lys Asp Glu Val Gly Glu Leu Ser Ala Ser Asp
        515                 520                 525
Thr Lys Arg Phe Val Lys Leu Val Arg Lys Thr Glu Ala Glu Ile Leu
    530                 535                 540
Asn Lys Ala Asp Val Val Cys Cys Thr Cys Val Gly Ala Gly Asp Lys
545                 550                 555                 560
Arg Leu Asp Thr Lys Phe Arg Thr Val Leu Ile Asp Glu Ser Thr Gln
                565                 570                 575
Ala Ser Glu Pro Glu Cys Leu Ile Pro Ile Val Lys Gly Ala Lys Gln
            580                 585                 590
Val Ile Leu Val Gly Asp His Gln Gln Leu Gly Pro Val Ile Leu Glu
        595                 600                 605
Arg Lys Ala Ala Asp Ala Gly Leu Lys Gln Ser Leu Phe Glu Arg Leu
    610                 615                 620
Ile Ser Leu Gly His Val Pro Ile Arg Leu Glu Val Gln Tyr Arg Met
625                 630                 635                 640
Asn Pro Tyr Leu Ser Glu Phe Pro Ser Asn Met Phe Tyr Glu Gly Ser
                645                 650                 655
Leu Gln Asn Gly Val Thr Ile Glu Gln Arg Thr Val Pro Asn Ser Lys
            660                 665                 670
Phe Pro Trp Pro Ile Arg Gly Ile Pro Met Met Phe Trp Ala Asn Tyr
        675                 680                 685
Gly Arg Glu Glu Ile Ser Ala Asn Gly Thr Ser Phe Leu Asn Arg Ile
    690                 695                 700
Glu Ala Met Asn Cys Glu Arg Ile Ile Thr Lys Leu Phe Arg Asp Gly
705                 710                 715                 720
Val Lys Pro Glu Gln Ile Gly Val Ile Thr Pro Tyr Glu Gly Gln Arg
                725                 730                 735
Ala Tyr Ile Leu Gln Tyr Met Gln Met Asn Gly Ser Leu Asp Lys Asp
            740                 745                 750
Leu Tyr Ile Lys Val Glu Val Ala Ser Val Asp Ala Phe Gln Gly Arg
        755                 760                 765
Glu Lys Asp Tyr Ile Ile Leu Ser Cys Val Arg Ala Asn Glu Gln Gln
    770                 775                 780
Ala Ile Gly Phe Leu Arg Asp Pro Arg Arg Leu Asn Val Gly Leu Thr
785                 790                 795                 800
Arg Ala Lys Tyr Gly Leu Val Ile Leu Gly Asn Pro Arg Ser Leu Ala
                805                 810                 815
Arg Asn Thr Leu Trp Asn His Leu Leu Ile His Phe Arg Glu Lys Gly
```

-continued

```
                820                 825                 830
Cys Leu Val Glu Gly Thr Leu Asp Asn Leu Gln Leu Cys Thr Val Gln
            835                 840                 845
Leu Val Arg Pro Gln Pro Arg Lys Thr Glu Arg Pro Met Asn Ala Gln
        850                 855                 860
Phe Asn Val Glu Ser Glu Met Gly Asp Phe Pro Lys Phe Gln Asp Phe
865                 870                 875                 880
Asp Ala Gln Ser Met Val Ser Phe Ser Gly Gln Ile Gly Asp Phe Gly
                885                 890                 895
Asn Ala Phe Val Asp Asn Thr Glu Leu Ser Ser Tyr Ile Asn Asn Glu
            900                 905                 910
Tyr Trp Asn Phe Glu Asn Phe Lys Ser Ala Phe Ser Gln Lys Gln Asn
        915                 920                 925
Arg Asn Glu Ile Asp Asp Arg Asn Leu Tyr Gln Glu Glu Ala Ser His
    930                 935                 940
Leu Asn Ser Asn Phe Ala Arg Glu Leu Gln Arg Glu Glu Gln Lys His
945                 950                 955                 960
Glu Leu Ser Lys Asp Phe Ser Asn Leu Gly Ile
                965                 970
```

(2) INFORMATION FOR SEQ ID NO:23:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:23:

```
Pro Gly Thr Gly Lys Thr
  1               5
```

(2) INFORMATION FOR SEQ ID NO:24:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:24:

```
Cys Ala Pro Ser Asn
  1               5
```

(2) INFORMATION FOR SEQ ID NO:25:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:25:

```
Gly Xaa Xaa Xaa Xaa Gly Lys Thr
  1               5
```

(2) INFORMATION FOR SEQ ID NO:26:

(i) SEQUENCE CHARACTERISTICS:
        (A) LENGTH: 215 base pairs (B) TYPE: nucleic acid
        (C) STRANDEDNESS: single
        (D) TOPOLOGY: linear (ii) MOLECULE TYPE: genomic RNA (xi) SEQUENCE DESCRIPTION: SEQ ID NO:26:

GAUACUUACC UGGCAGGGGA GAUACCAUGA UCACGAAGGU GGUUUUCCCA GGGCGAGGCU    60

UAUCCAUUGC ACUCCGGAUG UGCUGACCCC UGCGAUUUCC CCAAAUGUGG GAAACUCGAC   120

UGCAGAAUUG UUGUAGCACU CCAGCUGAUG AGUCCGUGAG GACGAAACUG UCUCCCCCAG   180

GGGCUAGUGG GGGACUGCGU UCGCGCUUUC CCCUG                              215

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: genomic RNA (xi) SEQUENCE DESCRIPTION: SEQ ID NO:27:

UAAUUUGUGG                                                           10

(2) INFORMATION FOR SEQ ID NO:28:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:28:

Leu Glu Cys Tyr Asn Cys Lys
 1               5

(2) INFORMATION FOR SEQ ID NO:29:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:29:

Leu Glu Asn Asp Tyr Asp Lys
 1               5